US012635997B2

(12) United States Patent
Mayberg

(10) Patent No.: US 12,635,997 B2
(45) Date of Patent: May 26, 2026

(54) METHODS FOR THE USE OF TISSUE REPAIR AND SEALING DEVICES HAVING A DETACHABLE GRAFT AND CLASP ASSEMBLY

(71) Applicant: PatchClamp MedTech, Inc., Newark, DE (US)

(72) Inventor: Marc Robert Mayberg, Seattle, WA (US)

(73) Assignee: PatchClamp Medtech, Inc., Newark, DE (US)

( * ) Notice: Subject to any disclaimer, the term of this patent is extended or adjusted under 35 U.S.C. 154(b) by 141 days.

(21) Appl. No.: 18/792,363

(22) Filed: Aug. 1, 2024

(65) Prior Publication Data

US 2025/0057521 A1     Feb. 20, 2025

Related U.S. Application Data

(63) Continuation of application No. 17/530,365, filed on Nov. 18, 2021, now Pat. No. 12,226,086, which is a
(Continued)

(51) Int. Cl.
*A61B 17/00*        (2006.01)
*A61L 27/04*        (2006.01)
(Continued)

(52) U.S. Cl.
CPC ........ *A61B 17/0057* (2013.01); *A61L 27/045* (2013.01); *A61L 27/047* (2013.01);
(Continued)

(58) Field of Classification Search
CPC ...... A61B 17/0057; A61B 2017/00615; A61B 2017/00623; A61B 2017/00659;
(Continued)

(56) References Cited

U.S. PATENT DOCUMENTS 4,007,743 A     2/1977   Blake
4,917,089 A     4/1990   Sideris
(Continued)

FOREIGN PATENT DOCUMENTS

CN          106562837 B     2/2018
WO        2006135609 A2   12/2006
(Continued)

OTHER PUBLICATIONS

Alvarez-Lorenzo, "Smart Drug Release from Medical Devices," Journal of Pharmacology and Experimental Therapeutics, 2019, pp. 544-554, vol. 370 [NPL_ALVAREZ-LORENZO].
(Continued)

*Primary Examiner* — Phong Son H Dang
(74) *Attorney, Agent, or Firm* — Gary M. Myles; Myles Intellectual Property Law

(57) ABSTRACT

Provided are tissue repair and sealing devices, and methods for the use of tissue repair and sealing devices, for use in both minimally invasive surgical (MIS) procedures and open, non-MIS procedures to rapidly repair tissue fenestrations and create a pressure-resistant, watertight seal in a tissue barrier. Tissue repair and sealing devices disclosed herein comprise an integrated graft and deployable clasp assembly and an applicator assembly having a clasp retain and release member that is slidably connected to a folded, deployable clasp. The applicator assembly places a graft on a tissue inner surface and a deployable clasp on a tissue outer surface to secure the graft to the tissue inner surface to, thereby, repair a tissue fenestration and create a watertight barrier.

6 Claims, 31 Drawing Sheets

Related U.S. Application Data continuation of application No. 17/156,162, filed on Jan. 22, 2021, now Pat. No. 11,219,436.

(60) Provisional application No. 62/965,722, filed on Jan. 24, 2020.

(51) Int. Cl.

| | |
|---|---|
| *A61L 27/06* | (2006.01) |
| *A61L 27/18* | (2006.01) |
| *A61L 27/22* | (2006.01) |
| *A61L 27/24* | (2006.01) |
| *A61L 27/36* | (2006.01) |
| *A61L 27/54* | (2006.01) |
| *A61L 31/02* | (2006.01) |
| *A61L 31/06* | (2006.01) |
| *A61L 31/14* | (2006.01) |

(52) U.S. Cl.
CPC .............. *A61L 27/06* (2013.01); *A61L 27/18* (2013.01); *A61L 27/227* (2013.01); *A61L 27/24* (2013.01); *A61L 27/3633* (2013.01); *A61L 27/3675* (2013.01); *A61L 27/54* (2013.01); *A61L 31/022* (2013.01); *A61L 31/06* (2013.01); *A61L 31/14* (2013.01); *A61B 2017/00615* (2013.01); *A61B 2017/00623* (2013.01); *A61B 2017/00659* (2013.01)

(58) Field of Classification Search
CPC ...... A61L 27/045; A61L 27/047; A61L 27/06; A61L 27/18; A61L 27/227; A61L 27/24; A61L 27/3633; A61L 27/3675; A61L 27/54; A61L 31/022; A61L 31/06; A61L 31/14; A61F 2/0063
See application file for complete search history.

(56) References Cited

U.S. PATENT DOCUMENTS

| | | | | |
|---|---|---|---|---|
| 5,053,046 | A | 10/1991 | Janese | |
| 5,334,217 | A | 8/1994 | Das | |
| 5,350,399 | A | 9/1994 | Erlebacher | |
| 5,425,744 | A | 6/1995 | Fagan | |
| 5,451,235 | A | 9/1995 | Lock | |
| 5,634,944 | A | 6/1997 | Magram | |
| 6,355,050 | B1 | 3/2002 | Andreas | |
| 6,436,030 | B2 | 8/2002 | Rehil | |
| 6,508,828 | B1 | 1/2003 | Akerfeldt | |
| 6,960,224 | B2 * | 11/2005 | Marino | A61B 17/0057 606/215 |
| 7,048,714 | B2 | 5/2006 | Richter | |
| 7,169,168 | B2 | 1/2007 | Van De Moer et al. | |
| 7,445,626 | B2 | 11/2008 | Songer | |
| 7,758,909 | B2 | 7/2010 | Ding | |
| 8,007,737 | B2 | 8/2011 | Fennimore | |
| 8,029,532 | B2 | 10/2011 | Sirota | |
| 8,105,352 | B2 | 1/2012 | Egnelov | |
| 8,257,389 | B2 | 9/2012 | Chanduszko | |
| 8,349,249 | B2 | 1/2013 | Wachter | |
| 8,382,796 | B2 | 2/2013 | Blaeser | |
| 8,398,676 | B2 | 3/2013 | Roorda | |
| 8,500,776 | B2 | 8/2013 | Ebner | |
| 8,663,254 | B2 | 3/2014 | Feussner | |
| 8,753,362 | B2 | 6/2014 | Widomski | |
| 8,758,403 | B2 | 6/2014 | Chanduszko | |
| 8,814,947 | B2 | 8/2014 | Callaghan | |
| 8,815,273 | B2 | 8/2014 | Atanasoska | |
| 8,834,864 | B2 | 9/2014 | Odar | |
| 8,889,172 | B1 * | 11/2014 | Trollsas | A61L 31/148 623/1.42 |
| 8,992,761 | B2 | 3/2015 | Lin | |
| 9,149,263 | B2 | 10/2015 | Chanduszko | |
| 9,605,175 | B2 | 3/2017 | Jennings | |
| 9,801,983 | B2 | 10/2017 | Gemborys | |
| 9,808,230 | B2 | 11/2017 | Brown | |
| 9,861,346 | B2 | 1/2018 | Callaghan | |
| 9,943,296 | B2 | 4/2018 | Rao | |
| 9,949,728 | B2 | 4/2018 | Cahill | |
| 10,004,586 | B2 | 6/2018 | Derwin | |
| 10,159,769 | B2 | 12/2018 | Gemborys | |
| 10,182,802 | B2 | 1/2019 | Nobles | |
| 10,188,381 | B2 | 1/2019 | Kurd | |
| 10,285,687 | B2 | 5/2019 | Nobles | |
| 10,314,912 | B2 | 6/2019 | Jennings | |
| 10,426,467 | B2 | 10/2019 | Miller | |
| 10,433,826 | B2 | 10/2019 | Grant | |
| 10,512,458 | B2 | 12/2019 | Nobles | |
| 2002/0068950 | A1 | 6/2002 | Corcoran | |
| 2002/0169475 | A1 | 11/2002 | Gainor | |
| 2002/0183787 | A1 | 12/2002 | Wahr | |
| 2003/0175410 | A1 | 9/2003 | Campbell | |
| 2004/0143277 | A1 | 7/2004 | Marino | |
| 2004/0143291 | A1 | 7/2004 | Corcoran | |
| 2004/0143294 | A1 | 7/2004 | Corcoran | |
| 2004/0225324 | A1 | 11/2004 | Marino | |
| 2005/0021152 | A1 | 1/2005 | Ogle | |
| 2005/0065546 | A1 | 3/2005 | Corcoran | |
| 2005/0065547 | A1 | 3/2005 | Marino | |
| 2005/0065548 | A1 | 3/2005 | Marino | |
| 2005/0070989 | A1 | 3/2005 | Lye | |
| 2005/0113868 | A1 | 5/2005 | Devellian | |
| 2005/0119675 | A1 | 6/2005 | Adams | |
| 2005/0267524 | A1 * | 12/2005 | Chanduszko | A61B 17/0057 606/213 |
| 2005/0283256 | A1 | 12/2005 | Sommerich | |
| 2006/0009800 | A1 * | 1/2006 | Christianson | A61B 17/0057 606/213 |
| 2006/0217760 | A1 * | 9/2006 | Widomski | A61B 17/12122 606/213 |
| 2007/0093860 | A1 | 4/2007 | Rao | |
| 2008/0051881 | A1 | 2/2008 | Feng | |
| 2010/0057115 | A1 | 3/2010 | Rao | |
| 2010/0114140 | A1 * | 5/2010 | Chanduszko | A61B 17/3468 606/185 |
| 2010/0114159 | A1 * | 5/2010 | Roorda | A61B 17/0057 606/215 |
| 2010/0191326 | A1 * | 7/2010 | Alkhatib | A61F 2/2439 623/2.11 |
| 2010/0286768 | A1 * | 11/2010 | Alkhatib | A61F 2/2439 623/2.11 |
| 2011/0295200 | A1 | 12/2011 | Speck | |
| 2011/0301697 | A1 | 12/2011 | Hoffmann | |
| 2012/0245629 | A1 | 9/2012 | Gross | |
| 2013/0013083 | A1 | 1/2013 | Blum | |
| 2013/0030455 | A1 * | 1/2013 | Subramanian | A61B 17/0057 606/157 |
| 2013/0238088 | A1 | 9/2013 | Navia | |
| 2014/0236194 | A1 | 8/2014 | Deutsch | |
| 2014/0315847 | A1 | 10/2014 | Peck | |
| 2014/0343602 | A1 * | 11/2014 | Cox | A61B 17/12113 606/215 |
| 2015/0031131 | A1 | 1/2015 | Dahl | |
| 2015/0080914 | A1 | 3/2015 | Roundy | |
| 2015/0164489 | A1 | 6/2015 | Duggal | |
| 2015/0173794 | A1 * | 6/2015 | Kurth | A61B 17/0057 600/203 |
| 2015/0196693 | A1 | 7/2015 | Lin | |
| 2016/0007978 | A1 | 1/2016 | Obermiller | |
| 2016/0082161 | A1 | 3/2016 | Zilberman | |
| 2016/0249896 | A1 | 9/2016 | Bippart | |
| 2017/0367710 | A1 * | 12/2017 | Yang | A61B 17/12177 |

FOREIGN PATENT DOCUMENTS

| | | | |
|---|---|---|---|
| WO | 2008115849 | A2 | 9/2008 |
| WO | 2008156487 | A1 | 12/2008 |

(56)        References Cited

FOREIGN PATENT DOCUMENTS

WO        2014144188 A1        9/2014
WO         201905551 A1        3/2019

OTHER PUBLICATIONS

Bejjani, "Safety and Efficacy of the Porcine Small Intestinal Submucosa Dural Substitute: Results of a Prospective Multicenter Study and Literature Review," Journal of Neurosurgery, 2007, pp. 1028-1033, vol. 106 [NPL_BEJJANI].

Chorath, "Failure Pressures of Dural Repairs in a Porcine Ex Vivo Model: Novel Use of Titanium Clips Versus Tissue Glue," Allergy & Rhinology, 2019, pp. 1-6, vol. 10 [NPL_CHORATH].

Cosgrove, "Safety and Efficacy of a Novel Polyethylene Glycol Hydrogel Sealant for Watertight Dural Repair," Journal of Neurosurgery, 2007, pp. 52-58, vol. 106 [NPL_COSGROVE].

Dafford, "Comparison of Dural Repair Techniques," The Spine Journal, 2015, pp. 1099-1105, vol. 15(5) [NPL_DAFFORD].

Downing, "Drug-eluting Microfibrous Patches for the Local Delivery of Rolipram in Spinal Cord Repair," Journal of Controlled Release, 2012, pp. 910-917, vol. 161 [NPL_DOWNING].

Epstein, "Dural Repair with Four Spinal Sealants: Focused Review of the Manufacturers' Inserts and the Current Literature," The Spine Journal, 2010, pp. 1065-1068, vol. 10 [NPL_EPSTEIN].

Esposito, "Fibrin Sealants in Dura Sealing: A Systematic Literature Review," PLoS ONE, 2016, pp. e0151533, vol. 11(4) [NPL_ESPOSITO].

Gilding, "Biodegradable Polymers for Use in Surgery—Polyglycolic/Poly(Actic Acid) Homo- and Copolymers," Polymer, 1979, pp. 1459-1464, vol. 20(12) [NPL_GILDING].

Hutchinson, "Evaluation of Fibrin Sealants for Central Nervous System Sealing in the Mongrel Dog Durotomy Model," Neurosurgery, 2011, pp. 921-929, vol. 69(4) [NPL_HUTCHINSON].

Kinaci, "Dural Sealants for the Management of Cerebrospinal Fluid Leakage after Intradural Surgery: Current Status and Future Perspectives," Expert Review of Medical Devices, 2019, pp. 549-553, vol. 16(7) [NPL_KINACI].

Kizmazoglu, "Comparison of Dural Closure Alternatives: An Experimental Study," British Journal of Neurosurgery, 2019, pp. 655-658, vol. 33(6) [NPL_KIZMAZOGLU].

Leng, "Endoscopic, Endonasal Resection of Craniopharyngiomas: Analysis of Outcome Including Extent of Resection, Cerebrospinal Fluid Leak, Return to Preoperative Productivity, and Body Mass Index," Neurosurgery, 2012, pp. 110-124, vol. 70(1) [NPL_LENG].

Megyesi, "Suturing Technique and the Integrity of Dural Closures: An in Vitro Study," Neurosurgery, 2004, pp. 950-955, vol. 55(4) [NPL_MEGYESI].

Narotam, "Collagen Matrix Duraplasty for Cranial and Spinal Surgery: A Clinical and Imaging Study," Journal of Neurosurgery, 2007, pp. 45-51, vol. 106 [NPL_NAROTAM].

Neulen, "Evaluation of Efficacy and Biocompatibility of a Novel Semisynthetic Collagen Matrix as a Dural Onlay Graft in a Large Animal Model," Acta Neurochir, 2011, pp. 2241-2250, vol. 153 [NPL_NEULEN].

Osbun, "A Multicenter, Single-Blind, Prospective Randomized Trial to Evaluate the Safety of a Polyethylene Glycol Hydrogel (Duraseal Dural Sealant System) as a Dural Sealant in Cranial Surgery," World Neurosurgery, 2012, pp. 498-504, vol. 78(5) [NPL_OSBUN].

Preul, "Toward Optimal Tissue Sealants for Neurosurgery: Use of a Novel Hydrogel Sealant in a Canine Durotomy Repair Model," Neurosurgery, 2003, pp. 1189-1199, vol. 53(5) [NPL_PREUL].

Santos, "Bioresorbable Polymers for Tissue Engineering," Tissue Engineering, 2010, ch. 11, pp. 225-245 (Ed. Daniel Eberli) [NPL_SANTOS].

Schmalz, "Use of an Absorbable Synthetic Polymer Dural Substitute for Repair of Dural Defects: A Technical Note," Cureus, 2018, pp. e2127, vol. 10(1) [NPL_SCHMALZ].

Seo, "Evaluation of the Safety and Effectiveness of an Alternative Dural Substitute using Porcine Pericardium for Duraplasty in a Large Animal Model," Journal of Clinical Neuroscience, 2018, pp. 187-191, vol. 58 [NPL_SEO].

Sheikh, "Biodegradable Materials for Bone Repair and Tissue Engineering Applications," Materials, 2015, pp. 5744-5794, vol. 8 [NPL_SHEIKH].

Van Doormaal, "Usefulness of Sealants for Dural Closure: Evaluation in an In Vitro Model," Operative Neurosurgery, 2018, pp. 425-432, vol. 15(4) [NPL_VANDOORMAAL].

Velnar, "Soft Tissue Grafts for Dural Reconstruction after Meningioma Surgery," Bosnian Journal of Basic Medical Science, 2019, pp. 297-303, vol. 19(3) [NPL_VELNAR].

Zilberman, "Drug-Eluting Medical Implants," Handbook of Experimental Pharmacology: Drug Delivery, 2010, pp. 299-341 (Ed. Schafer-Korting, Springer-Verlag) [NPL_ZILBERMAN].

Buddeberg, "Post-dural Puncture Headache," Minerva Anestesiologica, 2019, pp. 543-553, vol. 85(5) [NPL_BUDDEBERG].

Fang, "Treatment of Cerebrospinal Fluid Leak after Spine Surgery," Chinese Journal of Traumatology , 2017, pp. 81-83, vol. 20 [NPL_FANG].

Jaffray, "Minimally Invasive Surgery," Archives of Disease in Childhood, 2005, pp. 537-542, vol. 90(5) [NPL_JAFFRAY].

Rahnemai-Azar, "Percutaneous Endoscopic Gastrostomy: Indications, Technique, Complications, and Management" World Journal of Gastroenterology, 2014, pp. 7739-7751, vol. 20(24) [NPL_RAHNEMAI-AZAR].

Severson, "Cerebrospinal Fluid Leak," StatPearls [Internet], 2020 [NPL_SEVERSON].

Sharma, "Endoscopic Repair of Cerebrospinal Fluid Rhinorrhoea," European Annals of Otorhinolaryngology, Head and Neck Diseases, 2016, pp. 187-190, vol. 133 [NPL_SHARMA].

Ji, "Synthesis of PLA-based Thermoplastic Elastomer and Study on Preparation and Properties of PLA-based Shape Memory Polymers," Materials Research Express, 2020, pp. 015315, vol. 7 [NPL_JI].

International Search Report mailed May 7, 2021 in PCT Patent Application No. PCT/US21/14796, filed Jan. 22, 2021 and published Jul. 29, 2021 as WO2021151026A1.

Written Opinion of the International Searching Authority mailed May 7, 2021 in PCT Patent Application No. PCT/US21/14796, filed Jan. 22, 2021 and published Jul. 29, 2021 as WO2021151026A1.

* cited by examiner

20

29

25

39

35

37

27

55

57

61

50

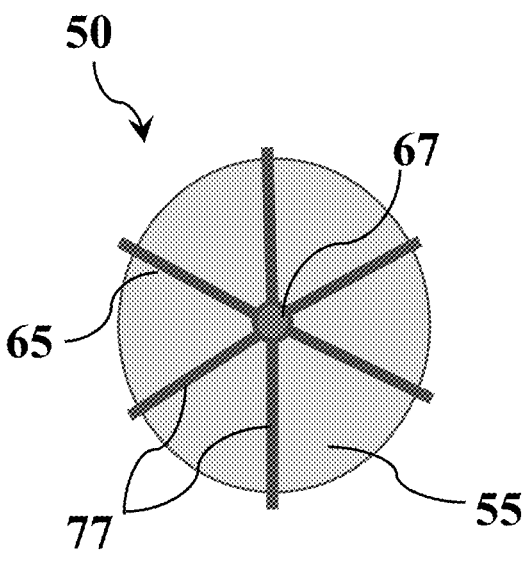
FIG. 13A
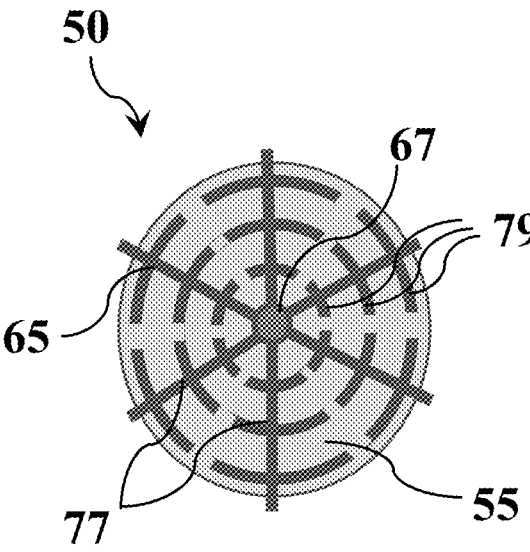
FIG. 13B
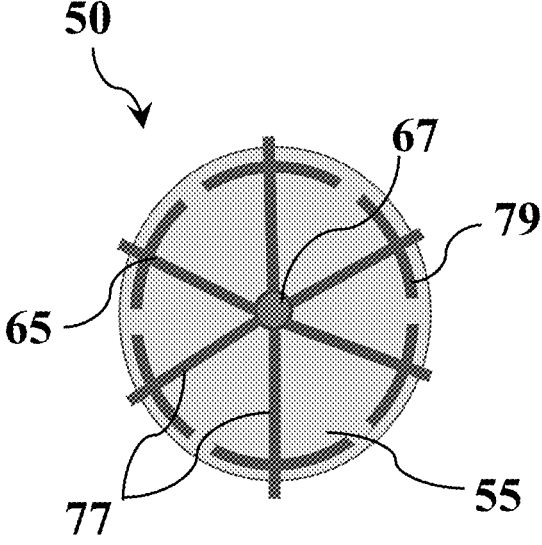
FIG. 13C
FIG. 13D

METHODS FOR THE USE OF TISSUE REPAIR AND SEALING DEVICES HAVING A DETACHABLE GRAFT AND CLASP ASSEMBLY

CROSS-REFERENCE TO RELATED APPLICATIONS

This U.S. non-provisional patent application was filed on Aug. 1, 2024 as U.S. patent application Ser. No. 18/792,363 and claims priority as a continuation from U.S. patent application Ser. No. 17/530,365, which was filed on Nov. 18, 2021 and claims priority as a continuation from U.S. patent application Ser. No. 17/156,162, which was filed on Jan. 22, 2021 and claims the benefit of U.S. Provisional Patent Application No. 62/965,722, which was filed on Jan. 24, 2020. The contents of U.S. patent application Ser. No. 17/530,365, U.S. patent application Ser. No. 17/156,162 and U.S. Provisional Patent Application No. 62/965,722 are incorporated herein by reference in their entirety.

BACKGROUND OF THE DISCLOSURE

Technical Field

The present disclosure relates, generally, to the field of medicine, in particular to surgery and surgical procedures, including both minimally invasive surgical (MIS) procedures and open surgical (non-MIS) procedures. Disclosed herein are tissue repair and scaling devices, and methods for their use, which comprise a detachable graft and clasp assembly for repairing tissue fenestrations, such as those that occur during surgical procedures or due to congenital, infectious or neoplastic processes. The tissue repair and sealing devices described herein permit the positioning of a graft on an inner tissue surface and a deployable clasp on an outer tissue surface. Devices are deployed by moving a clasp retain and release member along an applicator shaft to release a deployable clasp and, thereby, to secure a graft to an inner tissue surface; rapidly repair a tissue fenestration; and create a pressure-resistant, watertight seal.

Description of the Related Art

Advances in endoscopic, robotic, and microsurgical technology have permitted the rapid advancement of minimally invasive surgical (MIS) procedures whereby a surgical site is accessed through a small incision. For example, MIS procedures are used to access working spaces within a body cavity or body space (e.g., an abdominal cavity, a cranial sinus, an intracranial space, or a peri-spinal tissue) or a luminal pathway (e.g., a cardiovascular system; a gastrointestinal system; a cranial or spinal cerebrospinal fluid pathway; or an organ, such as a uterus, a bladder, or a kidney).

Several factors common to MIS procedures, including limited working space, restricted surgical access, poor visualization, and the friable nature of certain tissues, make it difficult to repair and seal cuts, tears, or openings in tissues that are beneath the skin (collectively tissue fenestrations). Failure to rapidly repair a tissue fenestration and create a watertight seal can result in the leakage of body fluids through the fenestrated tissue, which inhibits tissue healing, promotes infection, and leads to substantial post-surgical morbidity.

Various devices and methodologies are available in the art for closing tissue fenestrations during MIS procedures including, in various combination: (a) suturing or stapling, (b) applying a tissue adhesive, and (c) positioning and adhering a tissue graft. Existing devices and methodologies have limited practical utility, however, because they cannot rapidly repair tissue fenestrations and cannot reliably create pressure-resistant, watertight seals. As a result, healing of a fenestrated tissue is inadequate and complications often arise from the leakage of body fluids, including blood (hemorrhage, hematoma mass effect), cerebrospinal fluid (meningitis, pneumocephalus, intracranial hypotension), gastrointestinal contents (infection, fistula), and urine (fistula, infection).

Direct suturing or stapling of tissue fenestrations is time-consuming and technically difficult in the limited space and restricted access that is characteristic of MIS procedures. As a consequence, the rapid repair and creation of watertight seals is seldom achieved with the repair of tissue fenestrations produced during MIS procedures. Moreover, certain tissues that are encountered during MIS procedures are not amenable to suturing due to their friable nature, insufficient tissue to permit a complete closure, and close proximity to critical structures. And permanent metallic implants (i.e. staples) can interfere with subsequent magnetic resonance imaging.

Absorbable and non-absorbable tissue adhesives, such as fibrin glue and polyglycol gel, also have limited utility in the rapid repair of tissue fenestrations and creation of pressure-resistant, watertight seals. Tissue adhesives pose substantial technical challenges that can contribute to poor surgical results, namely: (1) the required mixing and applying of a rapidly-curing, two-component adhesive is difficult to perform in a small space; (2) buttressing of a graft with another tissue (e.g., fat) is often necessary; and (3) the bonding strength of tissue adhesives can be inadequate for the creation of a pressure-resistant, watertight seal.

Tissue patches, which include patches that are autologous (e.g., fascia and fat), heterologous (e.g., bovine or porcine tissues), or synthetic (e.g., collagen matrix), require the use of sutures to hold in place and are susceptible to infection and tissue rejection. Pedicle graft overlays to facilitate healing require a glue or buttress to ensure adherence, do not provide immediate watertight closure and are associated with elevated surgical morbidity.

Existing devices for attaching grafts to the outer surface of tissue fenestrations have limited utility in MIS procedures. Devices that are known in the art are difficult to manipulate and typically require additional procedures (e.g., harvesting a tissue for buttressing and placing drains to reduce pressure gradients). Moreover, tissue grafts attached to an outer tissue surface, are prone to failure and are particularly susceptible to pressure differentials between the inside and outside of a fenestrated tissue (e.g., a fenestrated blood vessel, dura mater, or gastrointestinal wall tissue). Because grafts positioned on an outer tissue surface often fail to repair tissue fenestrations and create watertight seals, fluids leak from a higher-pressure tissue interior (e.g., blood, cerebrospinal fluid, or gastrointestinal contents). This leads to poor healing, an elevated occurrence of infection, substantial post-surgical complications and morbidity, and prolonged hospitalization.

U.S. Pat. No. 5,634,944 ("Magram") discloses a flanged graft employing a graft material that requires suturing to an adjacent tissue, such as the dura. PCT Patent Publication No. WO 2019/055551 ("Sansur") discloses a heat-moldable resorbable bilayer sealing device that employs a patch that is molded to fit over an outer surface of a tissue fenestration and sutured in place. PCT Patent Publication No. WO 2008/115849 ("Baird") discloses a device that employs an anchoring element that is placed inside a tissue opening, a flexible membrane graft that is positioned outside of the tissue opening, and a ratchet connector to secure the anchoring element to the flexible membrane and occlude the tissue opening.

U.S. Patent Publication No. 2015/0164489 ("Duggal") discloses an expandable barrier inserted through a defect into an interior space, then expanded and positioned against the inner surface. A second barrier, which may also be expandable, is positioned against the outer surface of the defect and connected to the inner barrier through a ringed or notched bridging component.

U.S. Pat. No. 5,350,399 ("Erlebacher") discloses a sealing device for the repair of blood vessels (e.g., an arterial puncture) that employs a ratcheted connector and a saw-toothed guide to secure intraluminal and extraluminal bioresorbable occluders in place to achieve fenestration repair.

U.S. Pat. No. 7,169,168 ("Muijs Van De More") discloses a percutaneous system to seal arterial punctures in which an occluding element is passed into the lumen using a guide wire and attached with a suture-like component to secure an extraluminal element, thereby holding the occluding element against the inner surface of the puncture site.

U.S. Pat. No. 8,105,352 ("Egnelöv") discloses a device for the sealing of a puncture hole in a vessel wall, which includes an inner component that is positioned on an interior vessel wall and an outer component that is positioned on an outer vessel wall. The inner and outer components are secured by a thread-like retaining element.

U.S. Patent Publication No. 20070093840 ("Rao") discloses a device having two opposing annular plates (i.e. an inner plate that is coupled to an outer plate) that clamp the peripheral edges of a tissue defect to achieve the watertight repair of a tissue defect. The two opposing annular plates are placed independently on either side of the fenestration via a mechanical attachment that secures their position. A ratcheted plate connector must be trimmed after the plates are brought together.

Despite the availability of existing technologies for closing tissue fenestrations during surgical procedures, there remains an unmet need in the art for devices and methods that permit the rapid repair of tissue fenestrations and the reliable creation of pressure-resistant, watertight seals. The present disclosure fulfills these needs and provides further related advantages over existing technologies that are unsuitable for use in minimally invasive surgical (MIS) procedures.

SUMMARY OF THE DISCLOSURE

Provided herein are tissue repair and sealing devices that exhibit unexpected and surprising advantages over devices and technologies that are currently available in the art for repairing and scaling tissue fenestrations, including tissue fenestrations that occur during minimally invasive surgical (MIS) procedures. Disclosed herein are tissue repair and scaling devices and methods for their use in both MIS and open surgical (non-MIS) procedures to rapidly repair tissue fenestrations and reliably create watertight seals that are resistant to pressure differentials such as those that occur across the inside and outside of fenestrated tissues.

Within certain embodiments, the tissue repair and sealing devices disclosed herein comprise, in operable combination, (1) an applicator assembly comprising a clasp retain and release member having a proximal end and a distal end, wherein the clasp retain and release member is movably attached to an applicator shaft having a proximal end and a distal end, and (2) a detachable graft and clasp assembly (having a graft subassembly comprising a self-deploying graft that expands to its original shape after passage through a tissue fenestration) that is fixedly attached at or near its geometric center (a/k/a centroid) to a deployable clasp and coupler subassembly via a central coupler at/or near the geometric center of a deployable clasp.

Certain embodiments of the tissue repair and sealing devices disclosed herein employ detachable graft and clasp assemblies comprising a deployable clasp and coupler subassembly having a central coupler and a deployable clasp having a plurality of radial struts or spokes that emanate from the central coupler at or near the geometric center of the detachable graft and clasp assembly. In certain aspects of these embodiments, the detachable graft and clasp assembly attaches via the central coupler to the applicator assembly at the proximal end of the applicator shaft. In further aspects, the device is deployed by sliding the clasp retain and release member along the applicator shaft toward its distal end to, thereby, release the clasp from the retain and release member. Within still further aspects, when the device is deployed, the clasp secures the graft to the inner tissue surface and the clasp to the outer tissue surface to repair a tissue fenestration and create a pressure-resistant, watertight seal.

In operation, tissue repair and sealing devices disclosed herein permit the positioning of (1) a graft subassembly on an inner tissue surface and (2) a deployable clasp and coupler subassembly on an outer tissue surface. Prior to use, a detachable graft and clasp assembly is attached via a central coupler to an applicator assembly at the proximal end of an applicator shaft. The radial spokes or struts of a deployable clasp are folded away from the graft subassembly and inserted into the proximal end of a clasp retain and release member to hold the deployable clasp in place. Using the applicator assembly, the graft subassembly is inserted through a tissue fenestration and positioned on an inner tissue surface while the deployable clasp and coupler assembly remains outside of the fenestrated tissue. The tissue repair and sealing devices are deployed by moving the clasp retain and release member toward the distal end of the applicator shaft to release the deployable clasp, which permits the deployable clasp to unfold, apply pressure to the outer tissue surface, secure the graft subassembly to the inner tissue surface and, thereby, to rapidly repair a tissue fenestration and reliably create a pressure-resistant, watertight seal.

Additional modifications of the tissue repair and sealing devices are described herein that address specific technical problems encountered in MIS surgery. These include (1) variations in the size and shape of graft subassemblies and deployable clasp and coupler subassemblies, (2) variations in the materials used for the graft subassemblies and deployable clasp and coupler subassemblies, (3) configurations that permit the use of tissue repair and sealing devices in endoscopic or percutaneous procedures (e.g., the use of conical graft elements and flexible applicator assemblies having a channel for accommodating a guide wire), and (4) the incorporation of drug-eluting matrix materials in place of or in combination with the graft component to provide the continuous drug delivery at the site of application.

Exemplified herein are deployable devices that comprise a deployable clasp having a plurality of flexible spokes or struts that emanate radially from the coupler wherein the deployable clasp exhibits suitable biophysical properties, size, shape, and dimensions to secure a graft that is positioned on an inner tissue surface and a clasp that is positioned on an outer tissue surface and to, thereby, repair a tissue fenestration and create a pressure-resistant, watertight seal.

Within some aspects, the tissue repair and sealing devices utilize a detachable graft and clasp assembly in which one or more elements of the graft subassembly and/or the deployable clasp and coupler subassembly comprise a biopolymer that exhibits shape memory and superelasticity characteristics including, for example, a biopolymer selected from the group consisting of a polylactide (PLA), a polyglycolide (PGA), a polylactide-co-D, L lactide (PDLLA), a polylactide-co-glycolide (PLGA), a polylactide-co-caprolactone (PLCL), a polycaprolactone (PCL), a polydioxanone (PDO), and a polylactide-co-trimethylene carbonate (PL-TMC). In certain applications, the biopolymer is a bioresorbable material.

Within further aspects, the tissue repair and sealing devices disclosed herein utilize a detachable graft and clasp assembly wherein the graft comprises a material that is selected from the group consisting of an autograft, an isograft, an allograft, and a xenograft. In related aspects grafts are derived from an animal tissue selected from the group consisting of a human tissue, a bovine tissue, and a porcine tissue and include, for example, an animal tissue is selected from the group consisting dermis, pericardium, and intestine.

In related aspects, tissue repair and sealing devices utilize a detachable graft and clasp assembly wherein the graft comprises one or more synthetic material(s), including, for example, a bioresorbable material such as poly(ethylene terephthalate) and/or expanded polytetrafluoroethylene (ePTF).

In other related aspects, tissue repair and sealing devices utilize a detachable graft and clasp assembly wherein the graft comprises a dural substitute, including, for example, a dural substitute that is selected from the group consisting of Duraform® dural graft implant, Biodesign® Dural Graft, DuraGen® Matrix, Cerafix dural graft®, PRECLUDE®, Lyoplant Onlay Graft®, Neuro-Patch Dural Graft®, SEAM-DURA®, and Durepair™ M Regeneration Matrix.

In some aspects, a graft according to these embodiments can be an autograft, an isograft, an allograft, or a xenograft. In other aspects, the graft comprises a tissue, a membrane, a mesh, a matrix. In further aspects, the graft comprises a material that is an autologous, homologous, or heterologous material. In yet other aspects, the graft comprises one or more synthetic material, including one or more synthetic material selected from the group consisting of poly(ethylene terephthalate) and expanded polytetrafluoroethylene (ePTF).

In still further aspects, the graft comprises a material that is derived from an animal tissue, such as an animal tissue that is selected from the group consisting a human tissue, a bovine tissue, and a porcine tissue, including an animal tissue that is selected from the group consisting of dermis, pericardium, and intestine. Grafts according to these embodiments may comprise one or more of the following: (1) an acellular, porous extracellular matrix scaffold; (2) collagen; (3) clastin; and (4) a growth factor. In some aspects, grafts according to these embodiments comprise a mesh having a porosity that is sufficient to allow cells to enter, adhere, and undergo a cycle of remodeling.

In further aspects, grafts according to these embodiments comprise a dural substitute, such as, for example, a dural substitute that is selected from the group consisting of Duraform® dural graft implant, Biodesign® Dural Graft, DuraGen® Matrix, Cerafix dural graft®, PRECLUDER, Lyoplant Onlay Graft®, Neuro-Patch Dural Graft®, SEAM- DURA®, and Durepair™ Regeneration Matrix. In still further aspects, grafts according to these embodiments incorporate a drug-eluting matrix to provide a continuous release of drugs to fluids and tissues at the site of tissue repair and scaling.

Within yet other aspects, the tissue repair and sealing devices disclosed herein utilize a graft comprising an acellular, porous extracellular matrix scaffold of collagen, elastin, and, optionally, a growth factor. Such grafts optionally comprise a mesh having a porosity that is sufficient to allow cells to enter, adhere, and undergo a cycle of remodeling. Grafts may additionally comprise a drug eluting matrix.

Within other aspects, the tissue repair and sealing devices disclosed herein utilize a detachable graft and clasp assembly in which one or more elements of the graft subassembly and/or the deployable clasp and coupler subassembly comprise comprises a biocompatible, non-ferromagnetic, passivated metal or metal alloy wire that exhibits shape memory and superelasticity characteristics that permit the folding of said metal or metal alloy while retaining the capacity to unfold to a pre-folded state. Suitable biocompatible, non-ferromagnetic, passivated metal or metal alloy wires include wires comprising a metal or metal alloy that is selected from the group consisting of pure titanium; a titanium-based alloy; a cobalt-based alloy; a platinum-based alloy; and a molybdenum, tungsten, and tantalum alloy. Suitable metal or metal alloy having shape memory and superelasticity characteristics that are enhanced at elevated temperature include, for example, a nickel-titanium alloy (Nitinol) and a niobium-titanium alloy.

Other embodiments on the present disclosure include methods for the use of the tissue repair and sealing devices disclosed herein in open (non-MIS) or minimally invasive surgical (MIS) procedures to rapidly repair tissue fenestrations and create pressure-resistant, watertight seals. Such methods include (a) selecting a tissue repair and sealing device having a detachable graft and clasp assembly removably attached to an applicator assembly, wherein said detachable graft and clasp assembly comprises a graft subassembly having a graft that is fixedly attached to a deployable clasp and coupler subassembly having a deployable clasp with radial struts or spokes and a central coupler and wherein said applicator assembly comprises an applicator shaft, a clasp retain and release member, and an actuator rod; (b) folding the deployable clasp radial struts or spokes and inserting into the clasp retain and release member; (c) inserting the graft through a tissue fenestration and positioning the graft on an inner tissue surface; (d) positioning the deployable clasp and coupler subassembly on an outer tissue surface; and (c) deploying the tissue repair and sealing device to release the deployable clasp from the clasp retain and release member to contact the outer tissue surface and secure the graft to the inner tissue surface, repairing the tissue fenestration, and create a pressure-resistant, watertight seal.

The tissue repair and sealing devices and methods disclosed herein may be employed in the direct visual, percutaneous, and/or endoscopic repair and sealing of a wide variety of human tissues. It will be understood by those of skill in the art that the tissue repair and sealing devices and methods described and exemplified herein may be modified without deviating from the spirit and scope of the present disclosure and to, thereby, address problems specific to the nature, condition, and surgical exposure of the fenestrated tissue. Such modifications may, for example, include variations in the material composition and/or orientation of clasp to conform with unique characteristics of the fenestrated tissue. Modifications may also include (1) the addition of a component to enable the intraoperative substitution of different graft materials, (2) variations in the size and shape of the graft-clasp unit, and (3) a flexible applicator with or without a guide wire for the percutaneous or endoscopic repair and scaling of punctures or ostomies.

These and other related aspects of the present disclosure will be better understood in light of the following drawings and detailed description, which exemplify certain aspects of the various embodiments.

BRIEF DESCRIPTION OF THE DRAWINGS

Certain aspects of the present disclosure will become more evident in reference to the drawings, which are presented for illustration, not limitation.

FIG. 1 is a drawing that illustrates an exemplary tissue repair and sealing device according to one embodiment of the present disclosure.

In FIG. 2, certain aspects of the detachable graft and clasp assembly include a deployable clasp and coupler subassembly comprising a deployable clasp having a plurality of struts or spokes that (1) emanate radially from the central coupler and (2) are in contact with a surface of the graft subassembly. In the particular graft subassembly shown in FIG. 2, the struts or spokes of the deployable clasp extend beyond the outer edge of the graft subassembly to facilitate folding the deployable clasp and retaining by the clasp retain and release member on the applicator assembly.

FIG. 3 illustrates a method for the use of a tissue repair and sealing device comprising a graft subassembly and deployable clasp and coupler subassembly as illustrated in FIGS. 1A-1C and FIG. 2 to rapidly repair a tissue fenestration and create a pressure-resistant, watertight seal.

In FIG. 3B is shown a tissue repair and sealing device prior to insertion of a graft subassembly through a tissue fenestration. The tissue repair and sealing device comprises an applicator assembly attached to a detachable graft and clasp assembly in which the struts or spokes of a deployable clasp and coupler subassembly are folded away from the graft subassembly and inserted into the proximal end of the clasp retain and release member. In FIG. 3C is shown the tissue repair and sealing device of FIG. 3B after insertion of the graft subassembly through the tissue fenestration. The graft subassembly is positioned on an inner tissue surface while the deployable clasp and coupler subassembly remains outside of the fenestrated tissue prior to deploying the tissue repair and sealing device. In FIG. 3D is shown the deploying of the tissue repair and scaling device by sliding the clasp retain and release member toward the proximal end of the applicator shaft to, thereby, release the deployable clasp. In FIG. 3E is shown the separation of the detachable graft and clasp assembly from the applicator assembly and the positioning of the deployable clasp and coupler assembly against an outer tissue surface to secure the graft subassembly to the inner tissue surface and, thereby, to repair the tissue fenestration and create a pressure-resistant, watertight seal.

FIG. 5 illustrates an embodiment of the presently disclosed tissue repair and scaling device that is configured for use in surgical procedures (e.g., lumbar punctures and gastrostomies) to occlude a large-bore needle puncture or percutaneous ostomy site.

As shown in FIG. 5C, a guidewire is passed through a large-bore needle that is inserted through a tissue barrier for drainage of fluid. In an alternative aspect of this method, the guidewire may be passed through an indwelling catheter prior to its removal. After removal of the large-bore needle or indwelling catheter, the guidewire remains in place (FIG. 5D). FIG. 5E illustrates the passage of the distal (external) end of the guidewire through the central channel within the conical occluder graft, central coupler, and applicator shaft. The tissue repair and scaling device is advanced along the guidewire to the puncture site and the conical occluder graft is passed through the puncture hole and positioned against the inner surface of the punctured tissue and the tissue repair and sealing device is deployed by moving the clasp retain and release member toward the distal end of the applicator shaft to release the deployable clasp and coupler subassembly (FIG. 5F). The deployable clasp is positioned against and applies pressure to the outer tissue surface to secure the conical occlude graft, repair the puncture, and create a pressure-resistant, watertight seal. The applicator assembly is detached from the detachable graft and clasp assembly, which remains at the puncture site, and the applicator assembly is removed by sliding along the guidewire after which the guidewire is then removed (FIG. 5G).

FIG. 6 is a drawing that shows an optional aspect of the various tissue repair and sealing devices disclosed herein.

FIG. 13 is a drawing that shows various optional configurations of a detachable graft and clasp assembly that include a deployable clasp and coupler subassembly having a plurality of radial spokes or struts to permit the optimization of the deployable clasp and coupler subassembly for use in securing a graft subassembly to an inner tissue surface to rapidly repair tissue fenestrations of various size and within a variety of distinct tissues and to, thereby, reliably create a watertight seal.

FIG. 13A is a drawing that shows a detachable graft and clasp assembly comprising (1) a graft subassembly having a graft (with or without a form ring or ring stabilizing members) and (2) a deployable clasp and coupler subassembly having a central coupler and a deployable clasp having six (6) radial spokes or struts.

FIG. 13B is a drawing that shows a detachable graft and clasp assembly comprising (1) a graft subassembly having a graft (with or without a form ring or ring stabilizing members) and (2) a deployable clasp and coupler subassembly having a central coupler and a deployable clasp having twelve (12) radial spokes or struts to increase the force exerted by the deployable clasp when securing a graft to an inner tissue surface.

FIG. 13C is a drawing that shows a detachable graft and clasp assembly comprising (1) a graft subassembly having a graft (with or without a form ring or ring stabilizing members) and (2) a deployable clasp and coupler subassembly having a central coupler and a deployable clasp having six radial spokes or struts, wherein each radial spoke or strut further comprises a lateral extension to improve the stability of the deployable clasp and coupler subassembly.

FIG. 13D is a drawing that shows a detachable graft and clasp assembly comprising (1) a graft subassembly having a graft (with or without a form ring or ring stabilizing members) and (2) a deployable clasp and coupler subassembly having a central coupler and a deployable clasp having six radial spokes or struts, wherein each radial spoke or strut further comprises a plurality of from 2 to 6 lateral extensions to increase the stability of the deployable clasp and coupler subassembly.

11 coupler and a deployable clasp having six radial spokes or struts, wherein each radial spoke or strut is fabricated to have an increased thickness, to curve away from the graft subassembly, and to include one or more barbs on an end of each radial spoke or strut.

Figure 15:
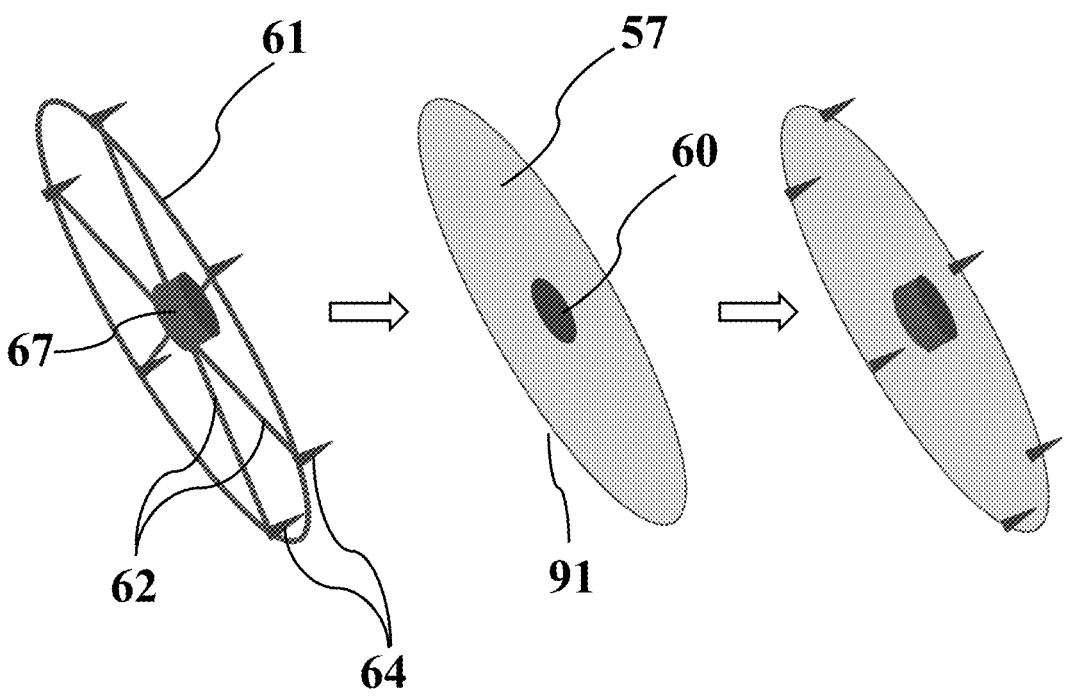

FIG. 15 is a drawing that shows the spatial arrangement of the component parts of an exemplary graft subassembly according to an alternate embodiment of the present disclosure that permits the use of autologous tissue grafts, or the substitution at the time of surgery of other non-rigid natural or synthetic graft materials in the tissue repair and sealing device. Within certain aspects of this embodiment, the graft subassembly comprises a graft having a central orifice at or near the geometric center for receiving a central coupler. The graft is attached across its inner surface to a form ring, which comprises a plurality of ring stabilizing members that emanate radially from a central coupler and a graft stabilizing prong to secure the graft subassembly.

Figure 16:
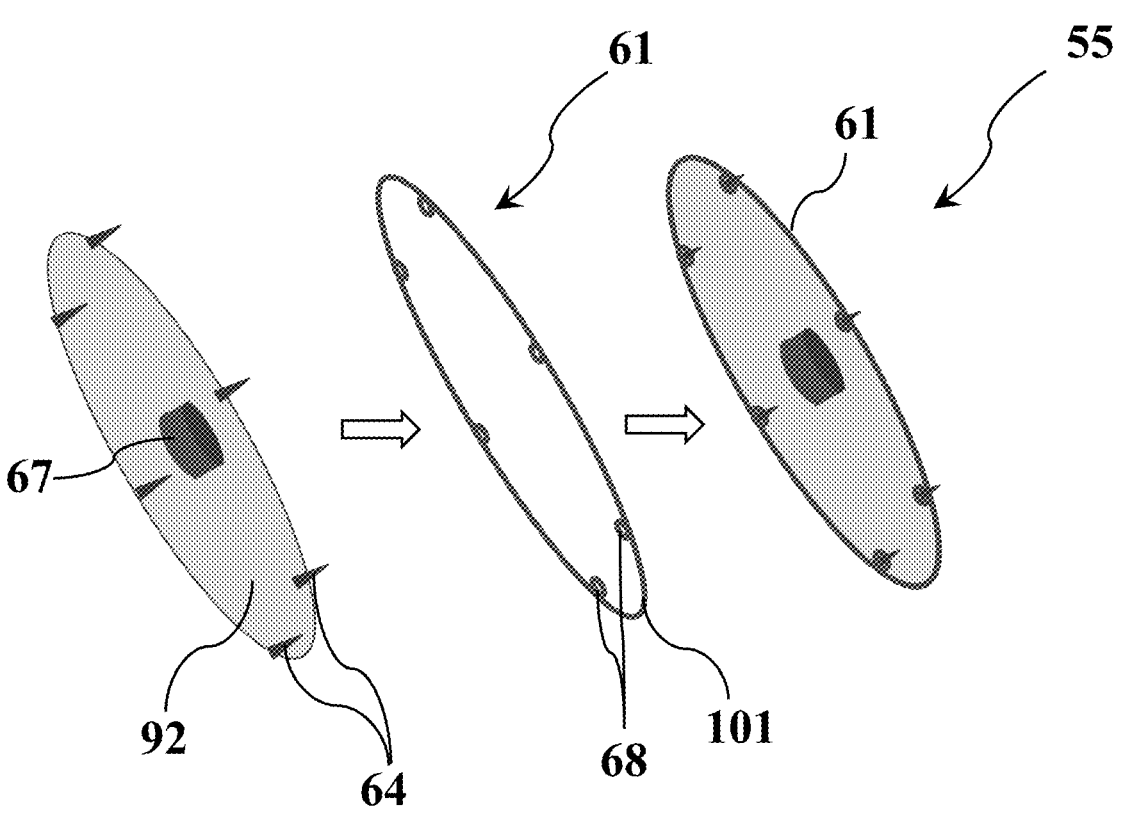

FIG. 16 is a drawing that shows the spatial arrangement of the component parts of certain aspects of an exemplary detachable graft and clasp assembly according to an alternate embodiment of the present disclosure wherein a second form ring having a plurality of graft stabilizing prong alignment rings radially distributed along its inside circumference is positioned over the outer surface of a graft such that it receives graft stabilizing prongs that protrude from form ring and that is attached to inner surface of the graft.

Figure 17:
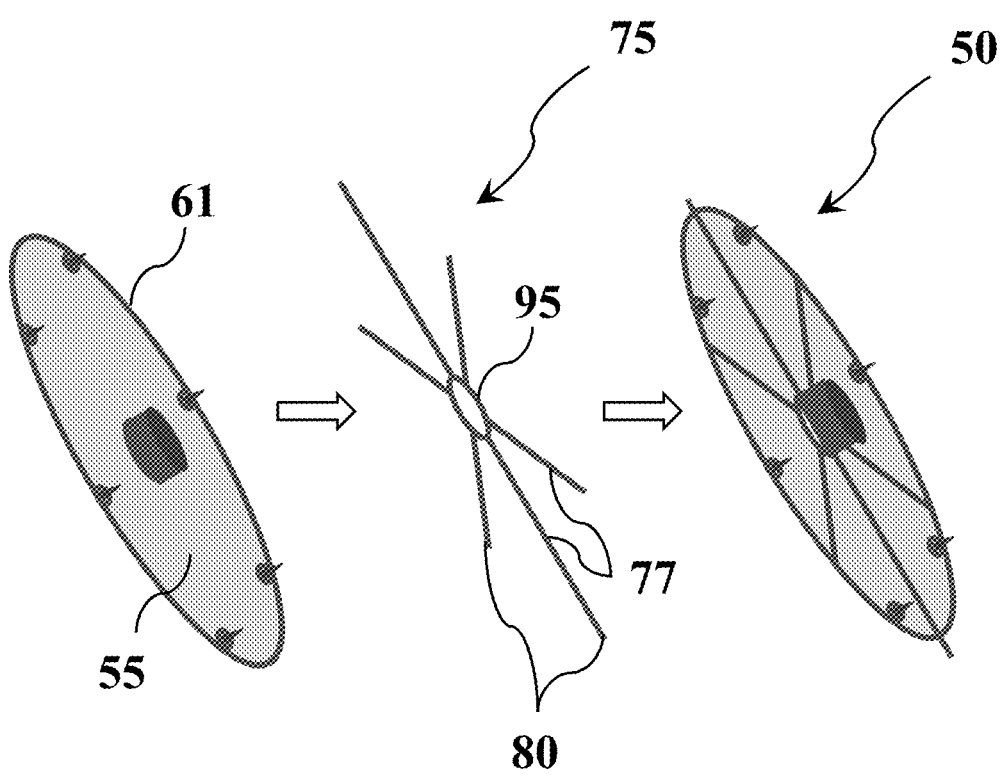

FIG. 17 is a drawing that shows the spatial arrangement of the component parts of certain aspects of an exemplary detachable graft and clasp assembly according to an alternate embodiment of the present disclosure (see, FIGS. 15 and 16) wherein the deployable clasp comprises a central coupler receiving ring and a plurality of radial spokes or struts that emanate from the central coupler receiving ring.

Figure 18:
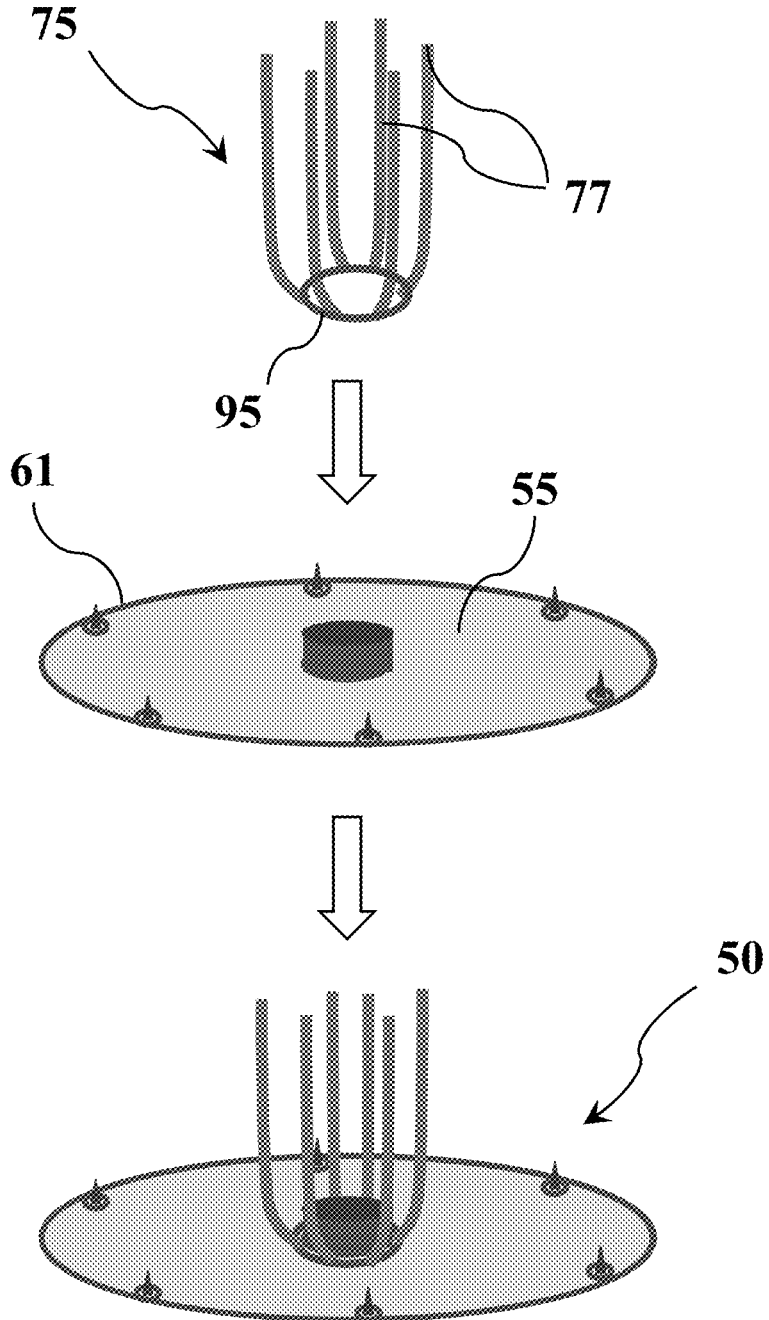

FIG. 18 is a drawing that shows the folding of radial spokes or struts that emanate from one end of a central coupler receiving member of a deployable clasp and coupler subassembly in preparation for attaching to applicator assembly and restraining with clasp retain and release member according to the embodiment presented in FIGS. 15-17.

Figure 19:
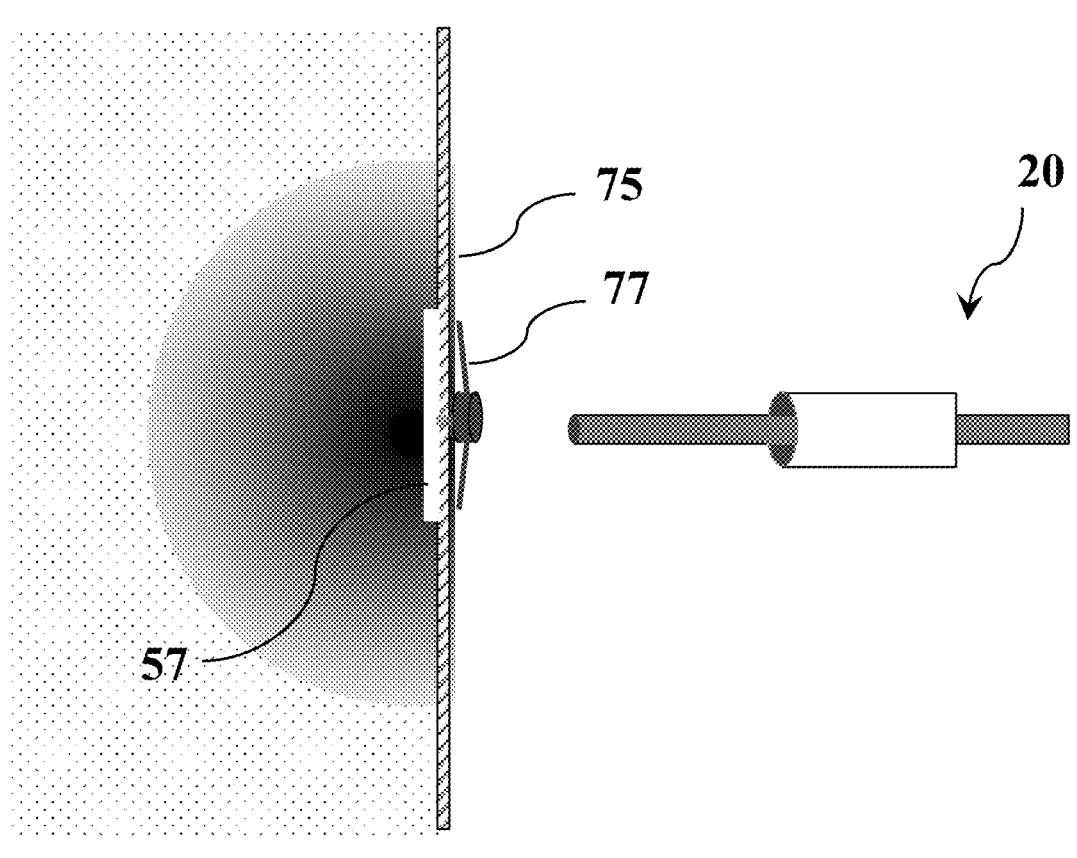

FIG. 19 is a schematic representation of an alternative embodiment of the tissue repair and sealing devices disclosed herein that is configured for providing continuous drug delivery to the fluid, tissue, or space within a body cavity, blood vessel, lumen or other structures within the body.

Figures 20A, 20B, 20C:
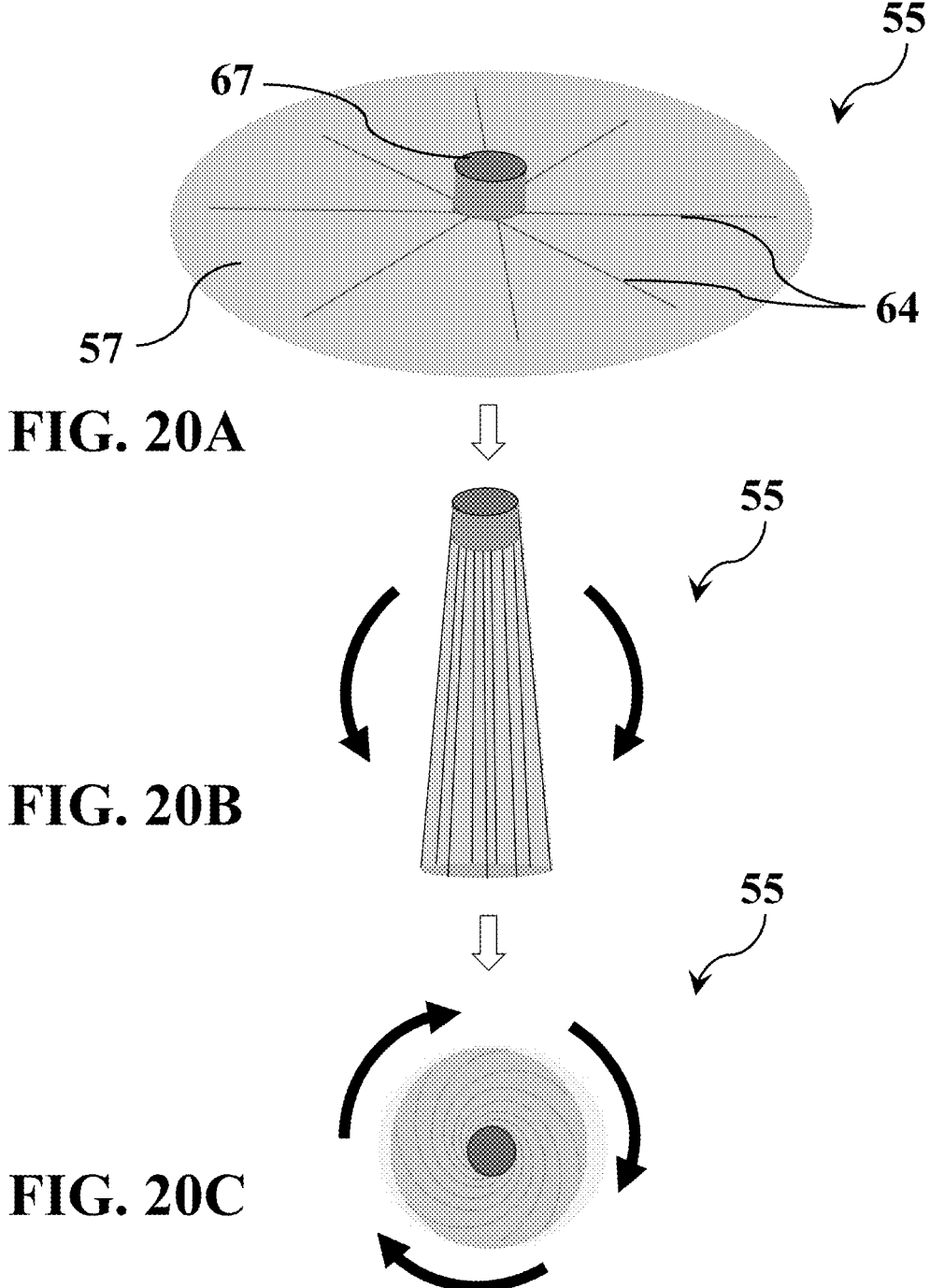

FIG. 20 illustrates an embodiment of a graft assembly in which the graft includes a plurality of biocompatible, non-ferromagnetic, passivated metal or metal alloy wires, which exhibit shape memory and superelasticity characteristics to permit the folding of the metal or metal alloy while retaining the capacity of the graft to unfold to a pre-folded state. FIG. 20A illustrates one aspect of this embodiment wherein the plurality of biocompatible, non-ferromagnetic, passivated metal or metal alloy wires emanate radially from the central coupler. As shown in FIG. 20B, the plurality of radial biocompatible, non-ferromagnetic, passivated metal or metal alloy wires permit the folding of graft away from central coupler in an umbrella or parasol configuration. As shown in FIG. 20C, the plurality of radial biocompatible, non-ferromagnetic, passivated metal or metal alloy wires also permits the further folding of the graft in a spiral configuration to reduce its diameter for insertion in a clasp retain and release member.

Figures 21A, 21B, 21C:
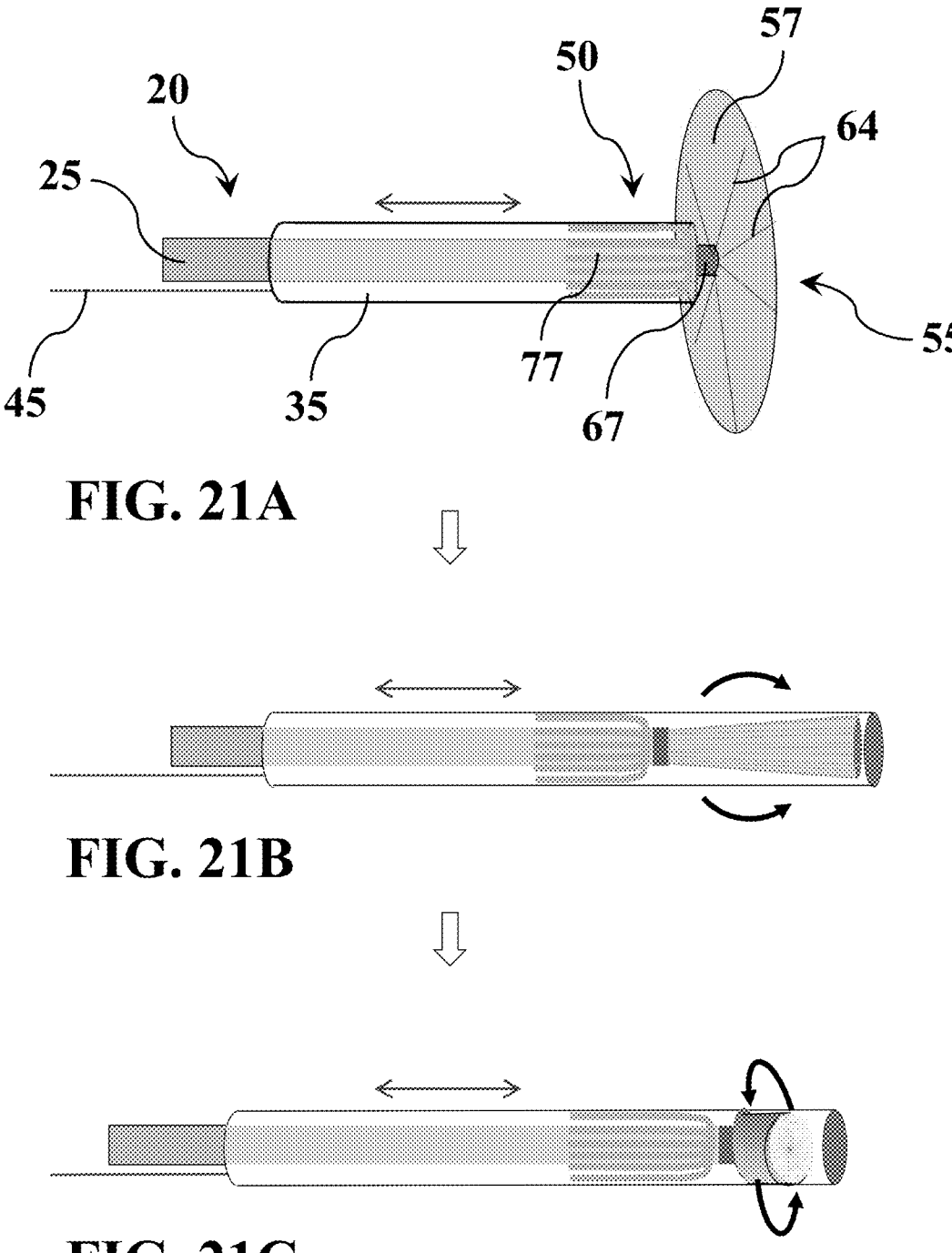

FIG. 21 illustrates a tissue repair and scaling device of the present disclosure that comprises (a) an applicator assembly having an applicator shaft, an elongated clasp retain and release member, and an actuator rod connected to (b) a detachable graft and clasp assembly having a graft subassembly and a deployable clasp and coupler subassembly (FIG. 21A). According to this embodiment detachable graft and clasp assembly utilizes a graft assembly as presented in FIG. 20 wherein the graft includes a plurality of biocompatible, non-ferromagnetic, passivated metal or metal alloy wires, which exhibit shape memory and superelasticity characteristics, to permit the folding of the metal or metal alloy while retaining the capacity to unfold to a pre-folded state. FIG. 21B illustrates the tissue repair and scaling device of FIG. 21A in which both radial struts or spokes and graft subassembly are folded and inserted into clasp retain and release member. FIG. 21C illustrates the further compacting of graft subassembly by folding in a manner that permits radial biocompatible, non-ferromagnetic, passivated metal or metal alloy wires to adopt a spiral configuration, which is advantageous for fenestration repairs tissues having limited space beneath the tissue barrier.

FIG. 22 illustrates a method for the use of a tissue repair and sealing device comprising a graft subassembly and deployable clasp and coupler subassembly as illustrated in FIGS. 20A-20C and FIGS. 21A-21C to rapidly repair a tissue fenestration and create a pressure-resistant, watertight seal. These tissue repair and sealing devices provide particular advantages in the repair of fenestrated tissues having a small tissue fenestration and/or that are friable in nature. In this embodiment, the graft subassembly is configured to include a plurality biocompatible, non-ferromagnetic, passivated metal or metal alloy wires, which exhibit shape memory and superelasticity characteristics, emanating radially from the center of the graft. Thus, the graft subassembly is configured to easily deform to fit within clasp retain and release member and to re-expand to its original shape upon entering the inside of the tissue and moving of clasp retain and release member.

Figures 22A, 22B, 22C:
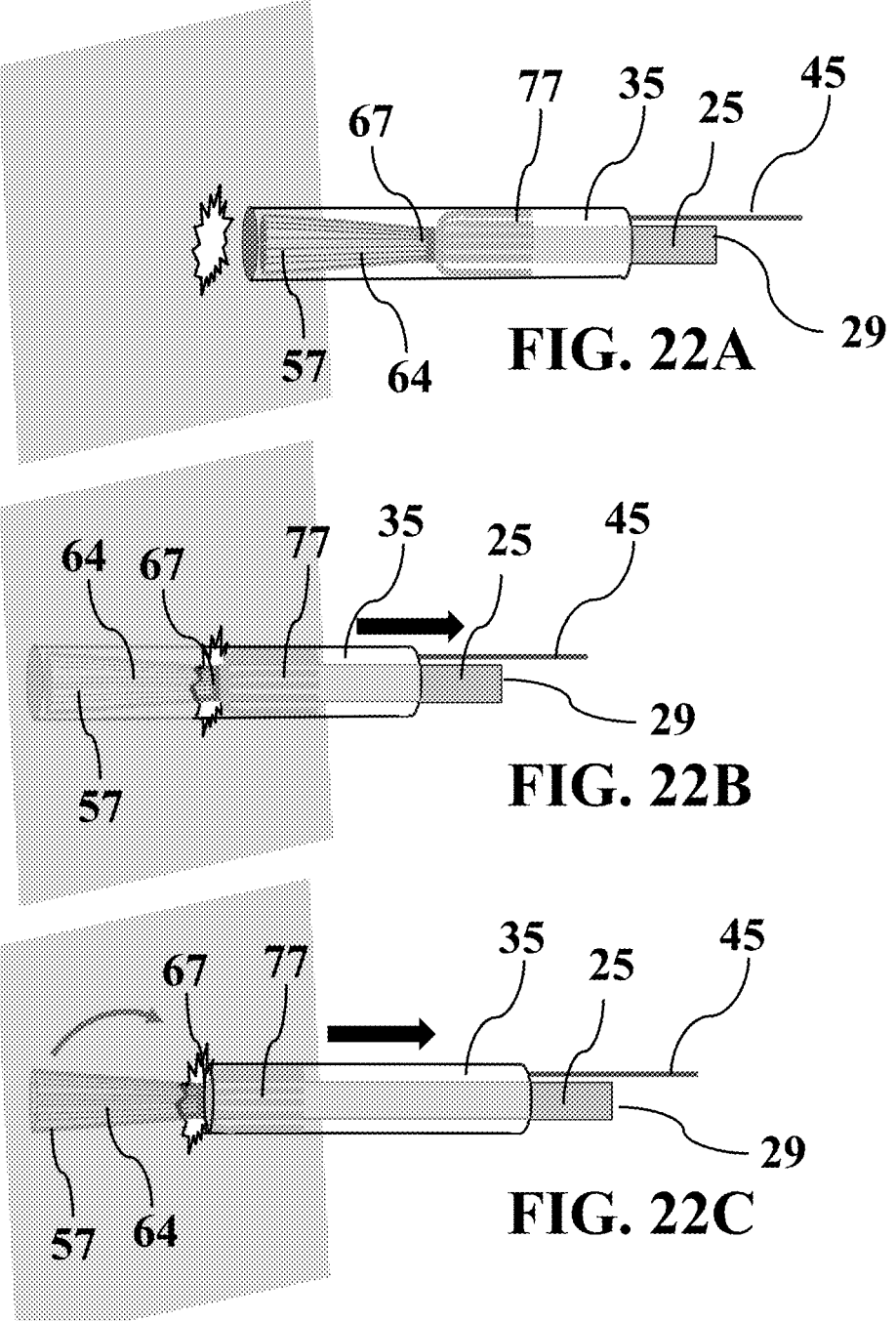

FIG. 22A illustrates an exemplary tissue repair and scaling device prior to deploying. Detachable graft and clasp assembly is attached to applicator assembly at the proximal end of an applicator shaft and the folded radial struts or spokes of a deployable clasp and coupler subassembly are retained at the proximal end of a clasp retain and release member. Prior to insertion of graft subassembly through a tissue fenestration, the radial struts or spokes of a deployable clasp and coupler subassembly are folded away from the graft subassembly and along a center of axis that passes through central coupler and inserted into the proximal end of the clasp retain and release member. In this embodiment is shown clasp retain and release member that is elongated to accommodate graft subassembly, including a graft that comprises a plurality biocompatible, non-ferromagnetic, passivated metal or metal alloy wires that emanate radially from the center of the graft and that is folded away from central coupler in an umbrella or parasol configuration and restrained by clasp retain and release member.

Figure 22D:
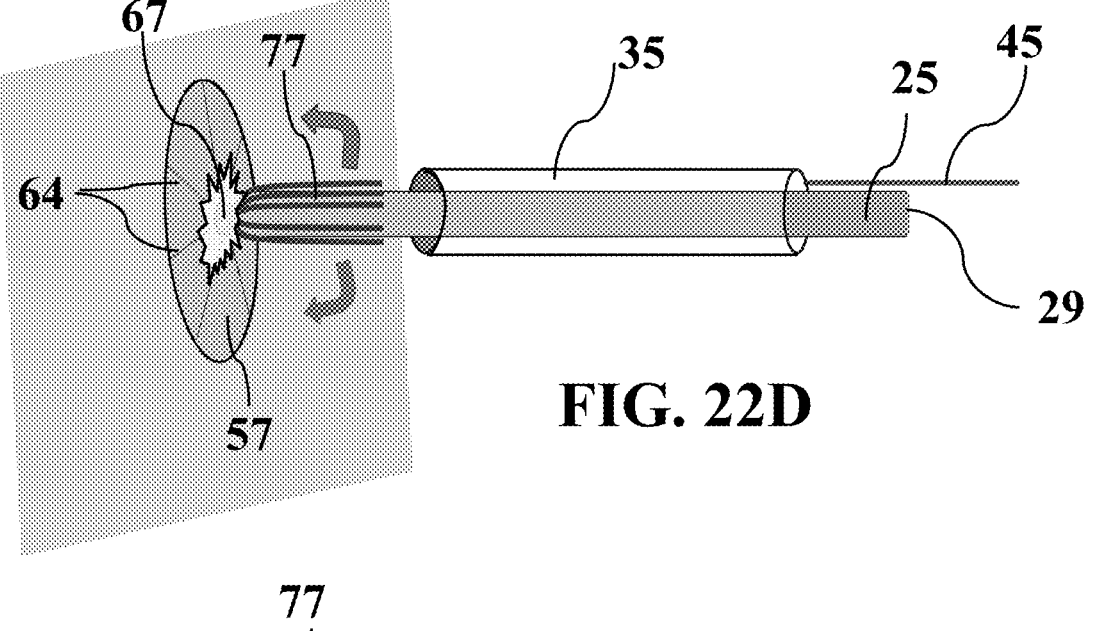
Figure 22E:
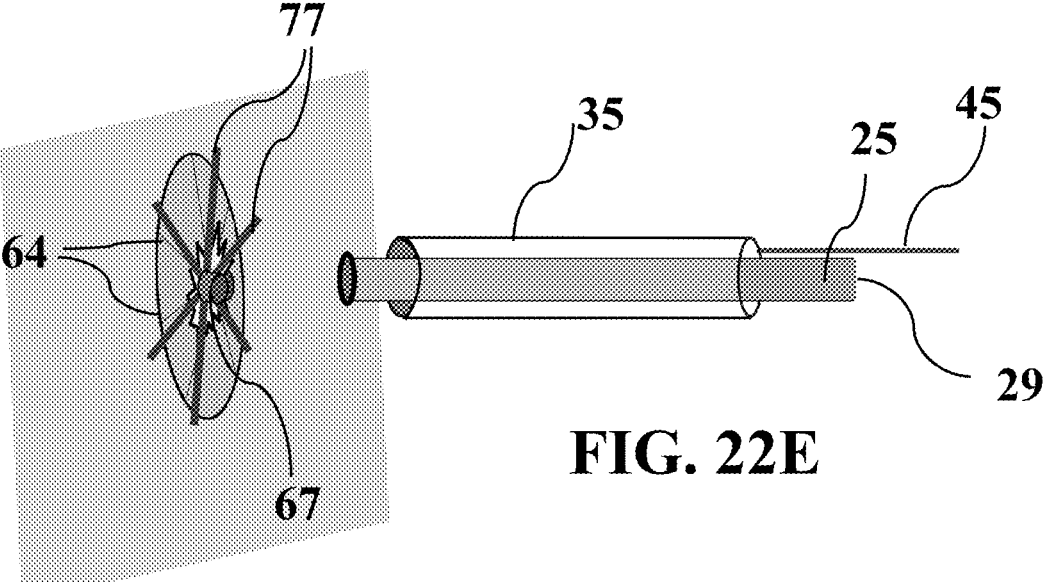

In FIG. 22B is shown the tissue repair and sealing device of FIGS. 20A-20C and FIGS. 21A-21C after passage of the proximal end of clasp retain and release member and graft subassembly though the tissue fenestration. In FIG. 22C is shown the deploying of graft subassembly by moving clasp retain and release member along applicator shaft toward its distal end and stopping when the proximal end of clasp retain and release member reaches the outside of the fenestrated tissue. Graft subassembly is then pulled back so that the graft contacts the inner surface of the fenestrated tissue while the deployable clasp and coupler subassembly remains outside of the fenestrated tissue and within clasp retain and release member. In FIG. 22D is shown the release deployable clasp and coupler subassembly from clasp retain and release member by sliding the clasp retain and release member toward the distal end of applicator shaft to, thereby, release the deployable clasp struts or spokes, which snap back to their original configuration and apply pressure against the outer surface of the fenestrated tissue, thereby securing the graft in an optimal position to seal the fenestration. In FIG. 22E is shown the separation of the detachable graft and clasp assembly from the applicator assembly and the positioning of the deployable clasp and coupler assembly against an outer tissue surface to secure the graft subassembly to the inner tissue surface and, thereby, to rapidly repair the tissue fenestration and reliably create a pressure-resistant, watertight seal.

FIG. 23 illustrates data obtained with a pressure chamber used for testing physical parameters of graft subassemblies for use in tissue repair and sealing devices according to the present disclosure, which allows for the establishment of internal fluid pressure waves that correspond to fluid in various human body compartments.

Figure 23A:
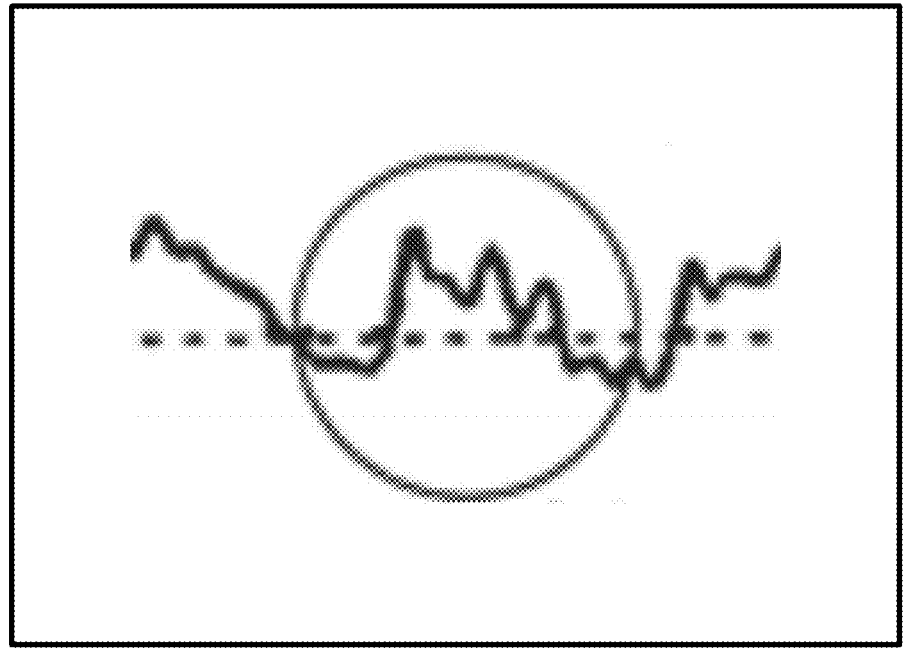
Figure 23B:
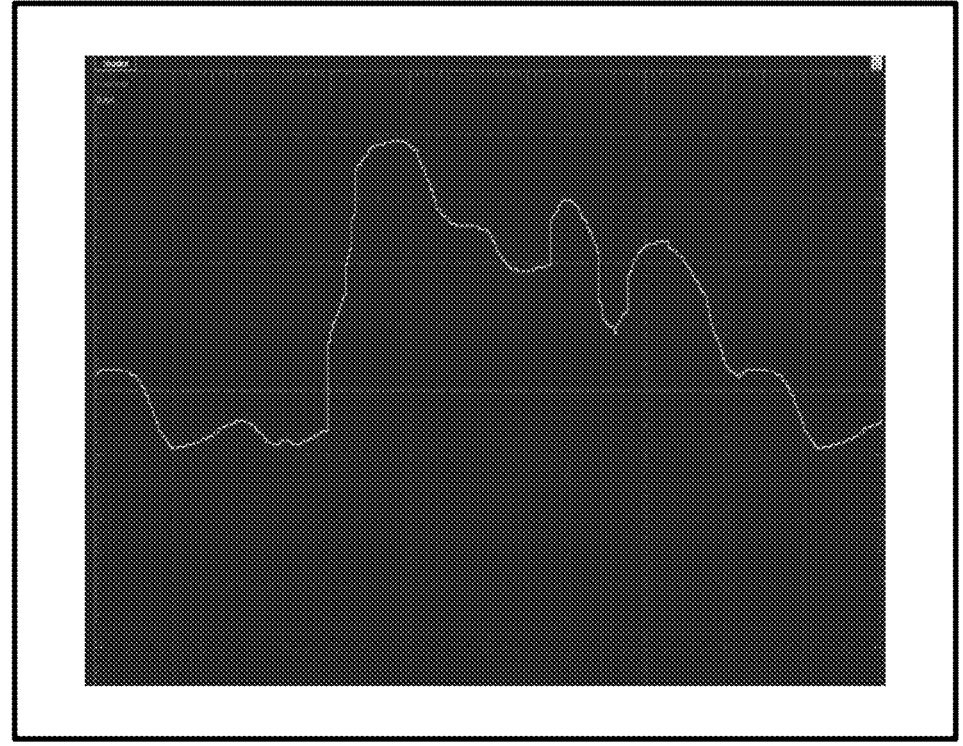

The in vitro pressure chamber enables the production of internal fluid pressure waves which correspond to fluid pressure waves in various human body compartments. In this example, porcine or ovine dura is placed in an opening and held between two acrylic places, with an embedded pressure sensor to record continuous pressures in the chamber. Waveforms are produced in the chamber fluid to reproduce the pulsatile pressure waves found in various human tissue compartments. FIG. 23A is an in vivo human CSF pressure waveform and FIG. 23B is an in vitro pressure chamber waveform.

Figure 24:
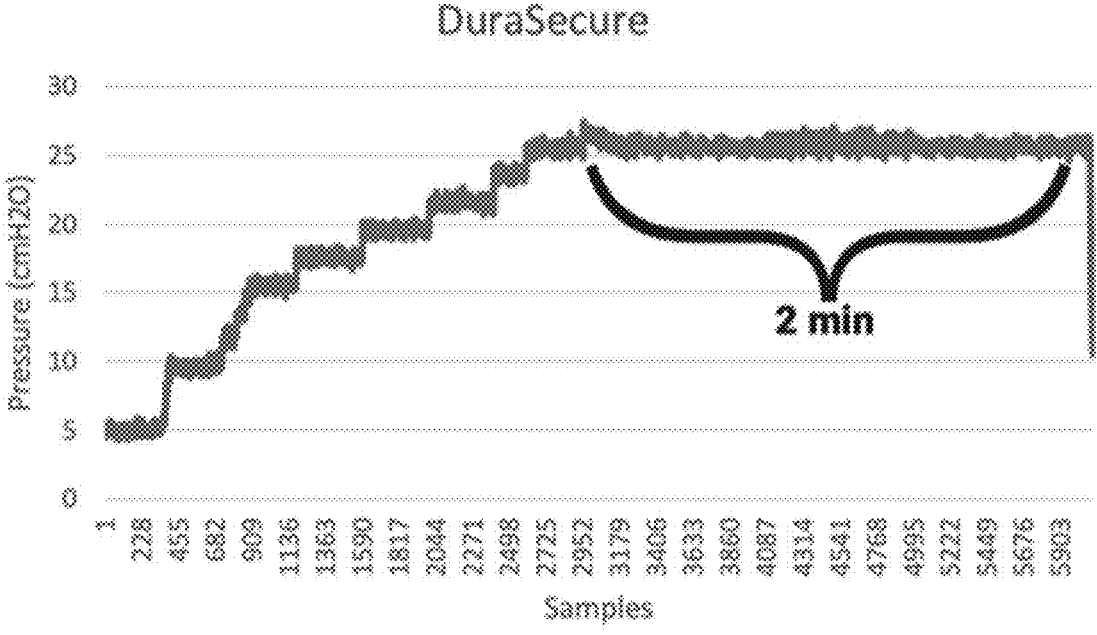

FIG. 24 is a graph of pressure-resistance data obtained with the in vitro pressure chamber presented in FIG. 23 and testing a graft subassembly comprising a DuraSecure graft material. This graph shows a typical measurement of pressure over time from the in vitro chamber to recapitulate human cerebrospinal fluid (CSF) within dura. In this case, the chamber pressure is initially brought to normal human CSF pressure (10 cm $H_2O$), then increased stepwise at increments of 2 cm $H_2O$ until pathologic elevated pressures (>20 cm $H_2O$) are achieved, then maintained for an additional 2 minutes without pressure decrement, indicative of a watertight seal. These data demonstrate that this graft subassembly maintained pressure over time with a step-wise increase from the normal in vivo pressure for human cerebrospinal fluid (i.e., 10 cm $H_2O$) and withstood an elevated pressure of 25 cm $H_2O$ for a period of two (2) minutes.

DETAILED DESCRIPTION OF THE DISCLOSURE

The present disclosure provides tissue repair and sealing devices, and methods for the use thereof in both MIS and non-MIS procedures, for rapidly repairing tissue fenestrations and reliably creating pressure-resistant, watertight seals. Within certain embodiments, tissue repair and sealing devices according to the present disclosure comprise (1) an applicator assembly having a clasp retain and release member (having a proximal end and a distal end) that is movably connected to an applicator shaft (having a proximal end and a distal end) and (2) a detachable graft and clasp assembly comprising a graft subassembly that is fixedly attached to a deployable clasp and coupler subassembly for positioning a graft subassembly on an inner tissue surface and a deployable clasp and coupler subassembly on an outer tissue surface. Deploying the tissue repair and sealing device by moving the clasp retain and release member along the applicator shaft toward its distal end releases the deployable clasp and coupler subassembly to position the clasp onto an outer tissue surface and to secure the graft onto an inner tissue surface to, thereby, achieve the rapid repair of a tissue fenestration and the reliable creation of a pressure-resistant, watertight seal.

This disclosure will be better understood in view of the following definitions, which are provided for clarification and are not intended to limit the scope of the subject matter that is disclosed herein.

Definitions

Unless specifically defined otherwise herein, each term used in this disclosure has the same meaning as it would to those having skill in the relevant art.

As used herein, the terms "minimally invasive surgery" and "MIS" are used interchageably to refer to surgical procedures that avoid the use of open, invasive surgery in favor of closed or local surgery that limit the size of incisions to lessen wound healing time, associated pain, and risk of infection as compared to traditional "non-MIS" procedures. MIS procedures, such as such as endoscopy, laparoscopy, arthroscopy, involve the use of laparoscopic devices and remote-controlled manipulation of instruments with indirect observation of the surgical field through an endoscope or similar device, such as neuroendoscopy. MIS procedures also include the use of hypodermic injection, and air-pressure injection, subdermal implants, refractive surgery, percutaneous surgery, cryosurgery, microsurgery, keyhole surgery, endovascular surgery using interventional radiology (such as angioplasty), coronary catheterization, permanent placement of spinal and brain electrodes, stereotactic surgery, the Nuss procedure, radioactivity-based medical imaging methods, such as gamma camera, positron emission tomography and SPECT (single photon emission tomography). Related procedures are image-guided surgery, and robot-assisted surgery.

As used herein, the term "tissue barrier" refers to a layer of tissue in the body that separates two body compartments. "Tissue barriers" function in vivo as both protective shields and gate keepers between different compartments (e.g., blood and tissue) and are created by specialised membrane-associated proteins, located at the lateral plasma membrane of epithelial and endothelial cells. By sealing the paracellular space, such barriers impede the free diffusion of solutes and molecules across epithelial and endothelial monolayers, thereby creating an organ-specific homeostatic milieu. Tissue barriers include tissues that comprise the meninges, dura of the nervous system, abdominal wall, muscle fascia, blood vessels, esophagus, oropharynx, stomach, small and large intestine, rectum, trachea, bronchus, heart, bladder, ureter, urethra, uterus, peritoneum, pleura, fallopian tube, sclera of the eye, synovium, tympanic membrane or the capsule of a solid organ (e.g., kidney, liver, and pancreas), fluid or space contained by the tissue barrier (blood, cerebrospinal fluid, gastrointestinal contents, pleural cavity, peritoneal cavity, vitreous humor, inner ear, fallopian tube or joint space).

As used herein, the term "meninges" refers, collectively, to the three membranes (the dura mater, arachnoid mater, and pia mater) that line the skull and vertebral canal, enclose the brain and spinal cord, and protect the central nervous system. "Meningitis" is the inflammation of the meninges, which is typically caused by an infectious agent.

As used herein, the terms "dura" and "dura mater" are used interchangeably and refer to the outermost (i.e. closest to the skull and vertebrae) of the three layers of membrane called the meninges (i.e. the meningeal layers) that are made of dense irregular connective tissue. "Dura mater" (a/k/a "pachymeninx") is derived primarily from the neural crest cell population, with postnatal contributions of the paraxial mesoderm. "Dura mater" protects the central nervous system by surrounding the brain and the spinal cord.

As used herein, the terms "arachnoid mater" and "pia mater" refer to the two inner meningeal layers that are enveloped by the "dura" or "dura mater." The "arachnoid mater" is interposed between the much thicker "dura mater" and the deeper "pia mater." The "arachnoid mater" is separated from the "pia mater" by the subarachnoid space and is responsible for retaining cerebrospinal fluid ("CSF") within the subarachnoid space ("SAS"). The "pia mater" is a thin, water permeable, fibrous tissue that permits blood vessels to pass through and nourish the brain. The "arachnoid mater" and "pia mater" are known collectively as the "leptomeninges" and have complex functions as barriers and facilitators for the movement of fluid, solutes and cells at the surface of the CNS and of fluid and solutes within the CNS parenchyma. Reviewed by Weller et al., *Acta Neuropathologica* 135:363-385 (2018). Both the "arachnoid mater" and "pia mater" derive from the neural crest.

As used herein, the term "fenestration" refers to an opening in a body tissue barrier, such as a cut, tear, puncture, defect, or other breach. A fenestration may be spontaneous (e.g., a cerebrospinal leak from a congenital defect); secondary (e.g., a tissue barrier that is compromised by a tumor or infection); planned (e.g., an incision or puncture of a blood vessel, dura mater, or outer wall of a body organ); or unplanned (e.g., inadvertent durotomy, intestinal breach, or laceration of the wall of a body organ during a surgical procedure). A fenestration in a tissue barrier usually requires repair and sealing to prevent serious complications (e.g., infection, bleeding, and wound breakdown). However, for MIS procedures, the combination of restricted working space and access vectors, limitation of vision, and the nature and consistency of the fenestrated tissue barrier, significantly limit direct repair and sealing by traditional methods (e.g., suturing or stapling).

As used herein, the terms "durotomy," "unintended durotomy," and "incidental durotomy" refer to an unintended tear of the dura mater (dural tear) that commonly occurs during MIS procedures performed on the spine (e.g., lumbar micshaftiscectomy). The complexity of spinal MIS procedures contributes to the incidence of "durotomy." Durotomy require immediate repair and watertight sealing to prevent post-surgical complications, including leakage of cerebrospinal fluid with subsequent meningitis, or the accumulation of air in the spinal canal (i.e. pneumorachis, acrorachia, or epidural emphysema), most commonly within the extradural or subarachnoid space with disruption of the surrounding dura mater.

As used herein, the term "graft" refers, generally, to tissues, membranes, meshes, matrices, and the like that exhibit suitable biophysical properties and are of the appropriate size, shape, and other dimensions for adhering to inner tissue surfaces, repairing tissue fenestrations, and creating pressure-resistant, watertight seals. "Grafts" may derive from natural sources such as animal organ tissues and tissue barriers and include tissues from a donor that exhibit a defined genetic relationship to tissues from a recipient such as, for example, autografts (tissue obtained from patient), isografts (tissue obtained from a monozygotic twin), allografts (tissue obtained from another person), or xenografts (tissue obtained from a non-human animal species). Grafts from such natural sources may be autologous, homologous, or heterologous and may incorporate one or more synthetic material.

As used herein, the term "drug eluting graft" refers to graft materials that incorporate a drug eluting matrix to provide controlled focal drug release. Han and Lelkes, Focal Controlled Drug Delivery, Advances in Delivery Science and Technology (Springer, Boston, 2014).

As used herein, the term "non-resorbable" refers to materials that are not broken down and absorbed by the body, and thus are intended for long-term, structural applications. "Non-resorbable" materials include implantable polymers, such as polyethylene and polyketones (PEEK), phase pure $\beta$ Tricalcium phosphate (TCP), and hydroxyapatite (HA).

As used herein, the term "bioresorbable" refers to materials that are broken down and absorbed by the body, and thus do not need to be removed manually. Biosorbable materials include polymers including biopolymers, and copolymers thereof, such as polylactide (PLA), polyglycolide (PGA), polylactide-co-D, L lactide (PDLLA), poly-lactide-co-glycolide (PLGA), polylactide-co-caprolactone (PLCL), polycaprolactone (PCL), polydioxanone (PDO), polylactide-co-trimethylene carbonate (PL-TMC) which can be customized to meet mechanical performance parameters, biocompatibility, and resorption rates.

As used herein, the terms "passivated metal" or "passivated metal alloy" refer to metals and metal alloys that are resistant to corrosion and exhibit enhanced biocompatibility as compared to the native metal or metal alloy. Passivation may be achieved by applying an outer layer of shield material as a microcoating on the exposed surface of the metal or metal alloy.

Words and phrases using the singular or plural number also include the plural and singular number, respectively. For example, terms such as "a" or "an" and phrases such as "at least one" and "one or more" include both the singular and the plural. Terms that are intended to be "open" (including, for example, the words "comprise," "comprising," "include," "including," "have," and "having," and the like) are to be construed in an inclusive sense as opposed to an exclusive or exhaustive sense. That is, the term "including" should be interpreted as "including but not limited to," the term "includes" should be interpreted as "includes but is not limited to," the term "having" should be interpreted as "having at least."

The use of the term "or" in the claims is used to mean "and/or" unless explicitly indicated to refer to alternatives only or the alternatives are mutually exclusive, although the disclosure supports a definition that refers to only alternatives and "and/or."

Additionally, the terms "herein," "above," and "below," and words of similar import, when used in this application, shall refer to this application as a whole and not to any particular portion of the application.

It will be further understood that where features or aspects of the disclosure are described in terms of Markush groups, the disclosure is also intended to be described in terms of any individual member or subgroup of members of the Markush group. Similarly, all ranges disclosed herein also encompass all possible sub-ranges and combinations of sub-ranges and that language such as "between," "up to," "at least," "greater than," "less than," and the like include the number recited in the range and includes each individual member.

The practice of the present disclosure will employ conventional techniques and methodologies that are in common use in the field of medicine, in particular in conjunction with minimally invasive surgical (MIS) procedures and non-minimally invasive surgical (non-MIS) procedures. Such techniques and methodologies are explained fully in treatises on surgical procedures as well as the medical, scientific, and patent literature. See, e.g., Hunter and Spight, "Atlas of Minimally Invasive Surgical Operations" (McGraw-Hill Education, Inc., 2018); Jones and Schwaltzberg, "Operative Endoscopic and Minimally Invasive Surgery" (CRC Press, 2019); and Nahai, "The Art of Aesthetic Surgery" (2nd Ed., Thieme, 2010).

All references cited herein, whether supra or infra, including, but not limited to, patents, patent applications, and patent publications, whether U.S., PCT, or non-U.S. foreign, and all technical, medical, and/or scientific publications are hereby incorporated by reference in their entirety.

Tissue Repair and Sealing Devices

Provided herein are tissue repair and sealing devices that exhibit unexpected and surprising advantages over devices and technologies that are currently available in the art for repairing and scaling tissue fenestrations, including tissue fenestrations that occur during minimally invasive surgical (MIS) procedures. In operation, the presently disclosed tissue repair and scaling devices (1) position a graft subassembly on an inner tissue surface and (2) position a deployable clasp on an outer tissue surface to secure the graft to the inner tissue surface and, thereby, to repair a tissue fenestration and create a pressure-resistant, watertight seal.

Within certain embodiments, the tissue repair and sealing devices disclosed herein comprise, in operable combination, (1) an applicator assembly comprising a clasp retain and release member having a proximal end and a distal end, wherein the clasp retain and release member is movably attached to an applicator shaft having a proximal end and a distal end, and (2) a detachable graft and clasp assembly having a graft subassembly that is fixedly attached at or near its geometric center (a/k/a centroid) to a deployable clasp and coupler subassembly via a central coupler at/or near the geometric center of a deployable clasp.

Certain embodiments of the tissue repair and sealing devices disclosed herein employ detachable graft and clasp assemblies comprising a deployable clasp and coupler subassembly having a central coupler and a deployable clasp having a plurality of radial struts or spokes that emanate from the central coupler at or near the geometric center of the detachable graft and clasp assembly. In certain aspects of these embodiments, the detachable graft and clasp assembly attaches via the central coupler to the applicator assembly at the proximal end of the applicator shaft. In further aspects, the device is deployed by sliding the clasp retain and release member along the applicator shaft toward its distal end to, thereby, release the clasp from the retain and release member. Within still further aspects, when the device is deployed, the clasp secures the graft to the inner tissue surface and the clasp to the outer tissue surface to repair a tissue fenestration and create a pressure-resistant, watertight seal.

In operation, tissue repair and sealing devices disclosed herein permit the positioning of (1) a graft subassembly on an inner tissue surface and (2) a deployable clasp and coupler subassembly on an outer tissue surface. Prior to use, a detachable graft and clasp assembly is attached via a central coupler to an applicator assembly at the proximal end of an applicator shaft. The radial spokes or struts of a deployable clasp are folded away from the graft subassembly and inserted into the proximal end of a clasp retain and release member to hold the deployable clasp in place. Using the applicator assembly, the graft subassembly is inserted through a tissue fenestration and positioned on an inner tissue surface while the deployable clasp and coupler assembly remains outside of the fenestrated tissue. The tissue repair and sealing devices are deployed by moving the clasp retain and release member toward the distal end of the applicator shaft to release the deployable clasp, which permits the deployable clasp to unfold, apply pressure to the outer tissue surface, secure the graft subassembly to the inner tissue surface and, thereby, to rapidly repair a tissue fenestration and reliably create a pressure-resistant, watertight seal.

Additional modifications of the tissue repair and sealing devices are described herein that address specific technical problems encountered in MIS surgery. These include (1) variations in the size and shape of graft subassemblies and deployable clasp and coupler subassemblies, (2) variations in the materials used for the graft subassemblies and deployable clasp and coupler subassemblies, (3) rotation of the coupling component such that the graft can be oriented such that it is not perpendicular to the applicator shaft, thereby improving line-of-sight visualization of the fenestration during insertion of the graft, (4) configurations that permit the use of tissue repair and sealing devices in endoscopic or percutaneous procedures (e.g., the use of conical graft elements and flexible applicator assemblies having a channel for accommodating a guide wire), and (5) the incorporation of drug-eluting matrix materials in place of or in combination with the graft component to provide the continuous drug delivery at the site of application.

Exemplified herein are deployable devices that comprise a deployable clasp having a plurality of flexible spokes or struts that emanate radially from the coupler wherein the deployable clasp exhibits suitable biophysical properties, size, shape, and dimensions to secure a graft that is positioned on an inner tissue surface and a clasp that is positioned on an outer tissue surface and to, thereby, repair a tissue fenestration and create a pressure-resistant, watertight seal.

Figures 1A, 1B:
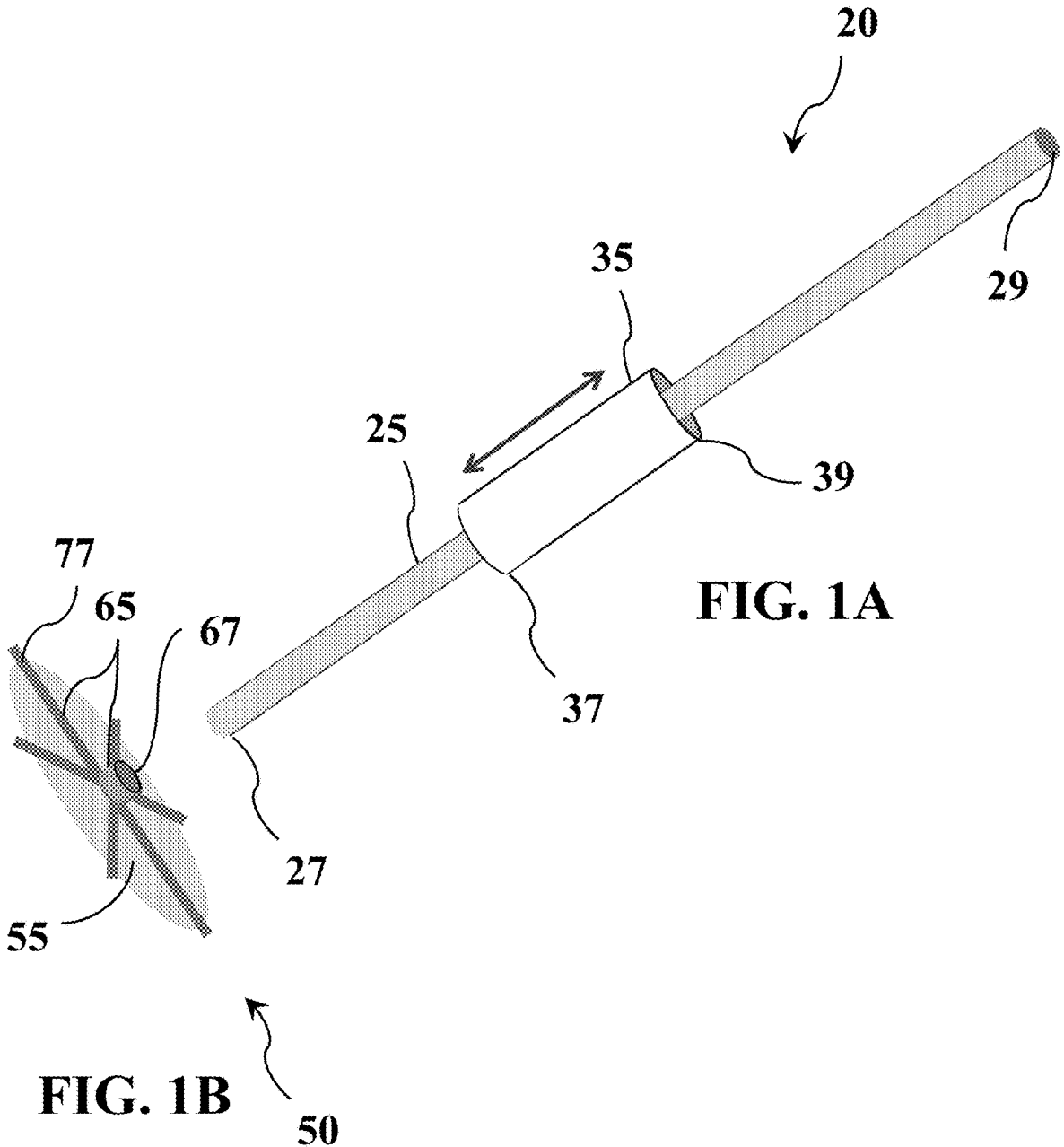
In FIG. 1A is shown an applicator assembly comprising an applicator shaft and a clasp retain and release member, wherein the clasp retain and release member is slidably connected to the applicator shaft.
In FIG. 1B is shown a detachable graft and clasp assembly comprising a graft subassembly and a deployable clasp and coupler subassembly, which comprises a central coupler for attaching the detachable graft and clasp subassembly to the applicator assembly at a proximal end of an applicator shaft.
Figure 1C:
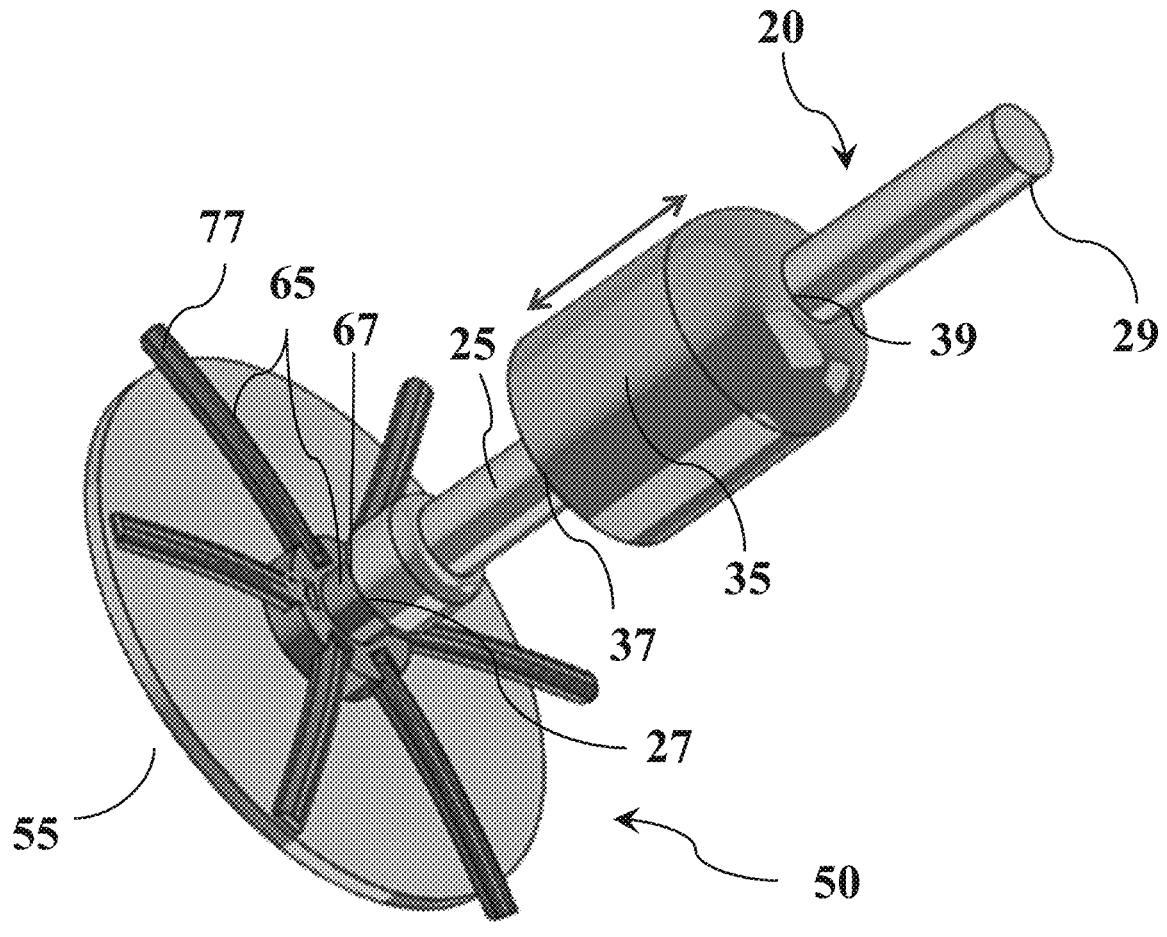
FIG. 1C is a CAD drawing showing a perspective view of an exemplary tissue repair and sealing device as described in further detail herein.

FIG. 1 illustrates an exemplary tissue repair and sealing device according to one embodiment of the present disclosure. In FIG. 1A is shown an applicator assembly 20 comprising a clasp retain and release member 35 having a proximal end 37 and a distal end 39, wherein clasp retain and release member 35 is slidably connected to applicator shaft 25 having a proximal end 27 and a distal end 29. In FIG. 1B is shown a detachable graft and clasp assembly 50 comprising graft subassembly 55 and deployable clasp and coupler subassembly 65, which comprises radial spokes or struts 77 and central coupler 67 for attaching detachable graft and clasp assembly 50 to applicator assembly 20 at the proximal end 27 of applicator shaft 25.

Detachable graft and clasp assembly 50 presented in FIG. 1 is configured for positioning graft subassembly 55 on an inner tissue surface and positioning deployable clasp and coupler subassembly 65 on an outer tissue surface. Tissue repair and sealing devices according to these embodiments are deployed by sliding clasp retain and release member 35 toward the distal end 29 of applicator shaft 25 to release deployable clasp and coupler subassembly 65 from the proximal end 37 of clasp retain and release member 35 and secure graft subassembly 55 to an inside tissue surface via deployable clasp and coupler subassembly 65 on an outside tissue surface to, thereby, repair a tissue fenestration and create a pressure-resistant, watertight seal.

In certain aspects of the embodiment presented in FIG. 1, applicator shaft 25 is a low-profile, bayonetted, and/or cylindrical applicator shaft. In other aspects of the embodiment presented in FIG. 1, clasp retain and release member 35 is a cylindrical clasp retain and release member having a proximal end 37 and a distal end 39, wherein proximal end 37 is configured for receiving and retaining deployable clasp and coupler subassembly 65 in a folded configuration (shown in FIG. 3). In further aspects of the embodiment presented in FIG. 1, graft subassembly 55 comprises an integrated graft. In still further aspects of the embodiment presented in FIG. 1, deployable clasp and coupler subassembly 65, is fabricated from one or more bioresorbable materials.

In use, a graft subassembly is selected based upon a visual assessment of the size of a tissue fenestration and the physical characteristics (e.g., friable nature) of the surrounding tissue. The graft subassembly 55 is inserted through the tissue fenestration into the space on the inside of the tissue barrier and is pulled back against the inner tissue surface. The deployable clasp and coupler subassembly 65 is released from the applicator assembly 20 by sliding the clasp retain and release member 35 toward the distal end 29 of applicator shaft 25 to contact the outer tissue surface and secure the graft subassembly 55 to the inner tissue surface and, thereby, repairing the tissue fenestration and creating a pressure-resistant, watertight seal.

Figure 2:
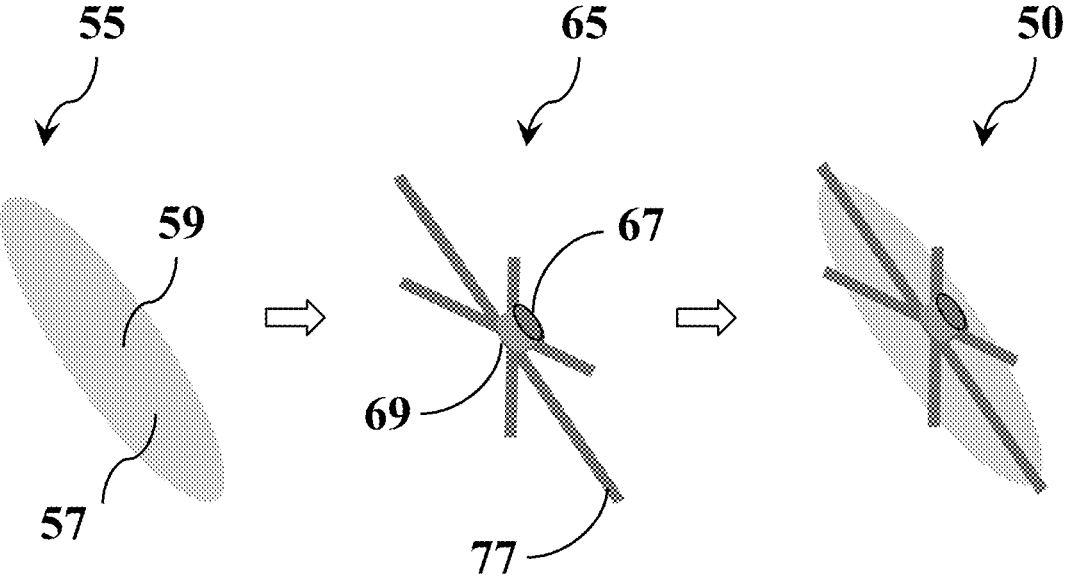
FIG. 2 is a drawing that shows the spatial arrangement of the component parts of an exemplary detachable graft and clasp assembly wherein a graft subassembly is fixedly attached at its center to a deployable clasp and coupler subassembly via a central coupler.

FIG. 2 illustrates the spatial arrangement of the component parts of an exemplary detachable graft and clasp assembly 50 wherein graft subassembly 55 is fixedly attached at its center 59 to deployable clasp and coupler subassembly 65 at a proximal side 69 of central coupler 67. In FIG. 2, certain aspects of exemplary detachable graft and clasp assembly 50 are shown, which include, without limitation, a deployable clasp and coupler subassembly 65 comprising a deployable clasp having a plurality of struts or spokes 77 that emanate radially from the proximal end 69 of central coupler 67 and that are each in contact with an inner surface of graft 57, and, optionally, which extend beyond the outer edge of graft subassembly 55.

Figure 3A:
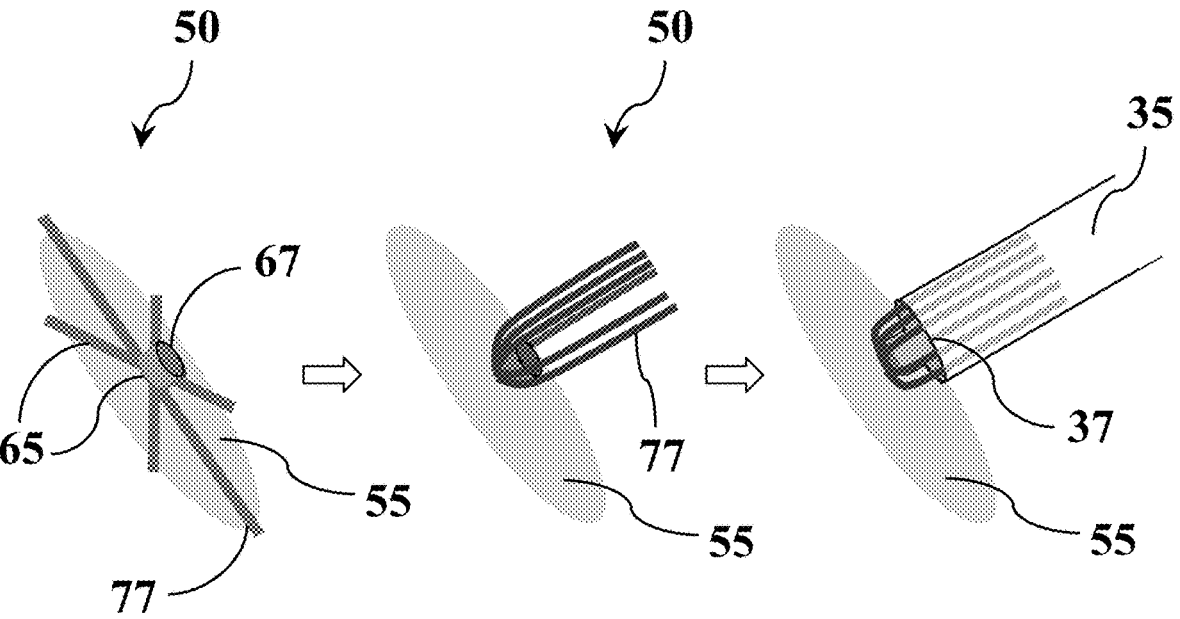
FIG. 3A is a drawing that shows the retention of a deployable clasp and coupler subassembly (according to FIGS. 1 and 2) by a clasp retain and release member of an applicator assembly. The deployable clasp and coupler subassembly is folded at each of the plurality of radial struts or spokes that emanate radially from central coupler and is inserted into the proximal end of clasp retain and release member to retain the deployable clasp in a folded configuration until the tissue repair and sealing device is deployed.

FIG. 3A illustrates the retention of radial struts or spokes 77 of deployable clasp and coupler subassembly 65 (according to FIG. 1 and FIG. 2) at the proximal end 37 of clasp retain and release member 35. Deployable clasp and coupler subassembly 65 is folded at each of the plurality of radial struts or spokes 77 that emanate radially from the distal side 71 of central coupler 67. The folded radial struts or spokes 77 of deployable clasp and coupler subassembly 65 are inserted into proximal end 37 of clasp retain and release member 35 to retain deployable clasp and coupler subassembly 65 in a folded configuration until the tissue repair and sealing device is deployed.

Figures 3B, 3C:
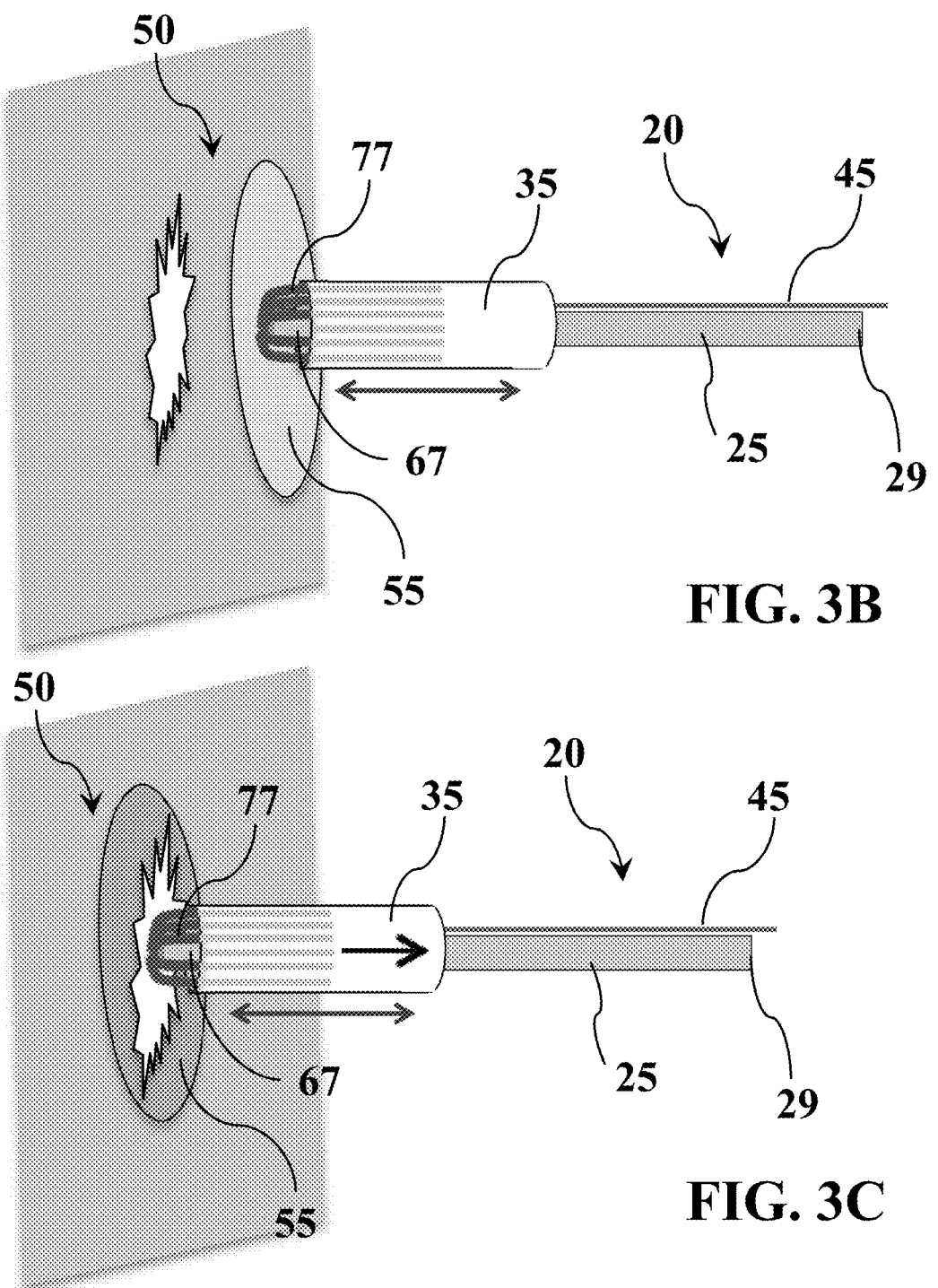
FIGS. 3B-3E are drawings that illustrate the use of a tissue repair and sealing device according to various embodiments of the present disclosure to rapidly repair a tissue fenestration and reliably create a pressure-resistant, watertight seal.

FIGS. 3B-3E illustrate the use of a tissue repair and sealing device comprising (a) applicator assembly 20 having a clasp retain and release member 35 that is movably attached to applicator shaft 25 and actuator rod 45 and (b) detachable graft and clasp assembly 50 having graft subassembly 55 fixedly attached to deployable clasp and coupler subassembly 65 having a central coupler 67 and a plurality of radial struts or spokes 77 as illustrated in FIG. 1 and FIG. 2 to rapidly repair a tissue fenestration and create a pressure-resistant, watertight seal. In FIG. 3B is shown a tissue repair and sealing device prior to insertion of a graft subassembly 55 through a tissue fenestration. The tissue repair and sealing device comprises an applicator assembly attached to a detachable graft and clasp assembly in which the struts or spokes 77 of a deployable clasp and coupler subassembly are folded away from the graft subassembly and inserted into the proximal end of the clasp retain and release member 35.

In FIG. 3C is shown the tissue repair and sealing device of FIG. 3B after insertion of the graft subassembly 55 through the tissue fenestration. The graft subassembly 55 is positioned on an inner tissue surface while the deployable clasp and coupler subassembly remains outside of the fenestrated tissue prior to deploying the tissue repair and scaling device.

Figures 3D, 3E:
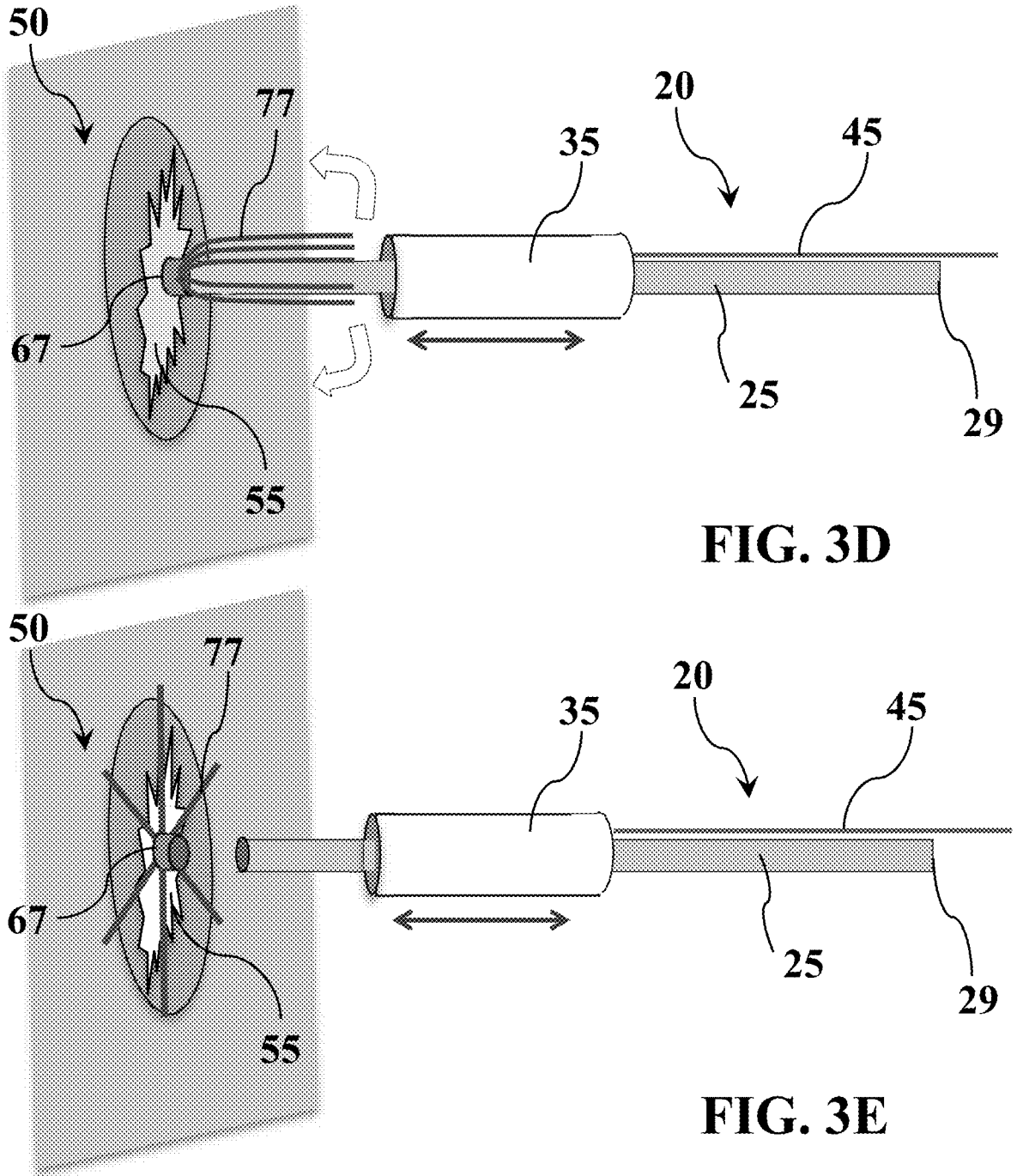

In FIG. 3D is shown the deploying of the tissue repair and scaling device by using actuator rod 45 to slide the clasp retain and release member 35 toward the distal end 29 of the applicator shaft 25 to, thereby, release the deployable clasp struts or spokes 77.

In FIG. 3E is shown the separation of the detachable graft and clasp assembly from the applicator assembly and the positioning of the deployable clasp and coupler assembly against an outer tissue surface to secure the graft subassembly to the inner tissue surface and, thereby, to repair the tissue fenestration and create a pressure-resistant, watertight seal.

Figures 4A, 4B:
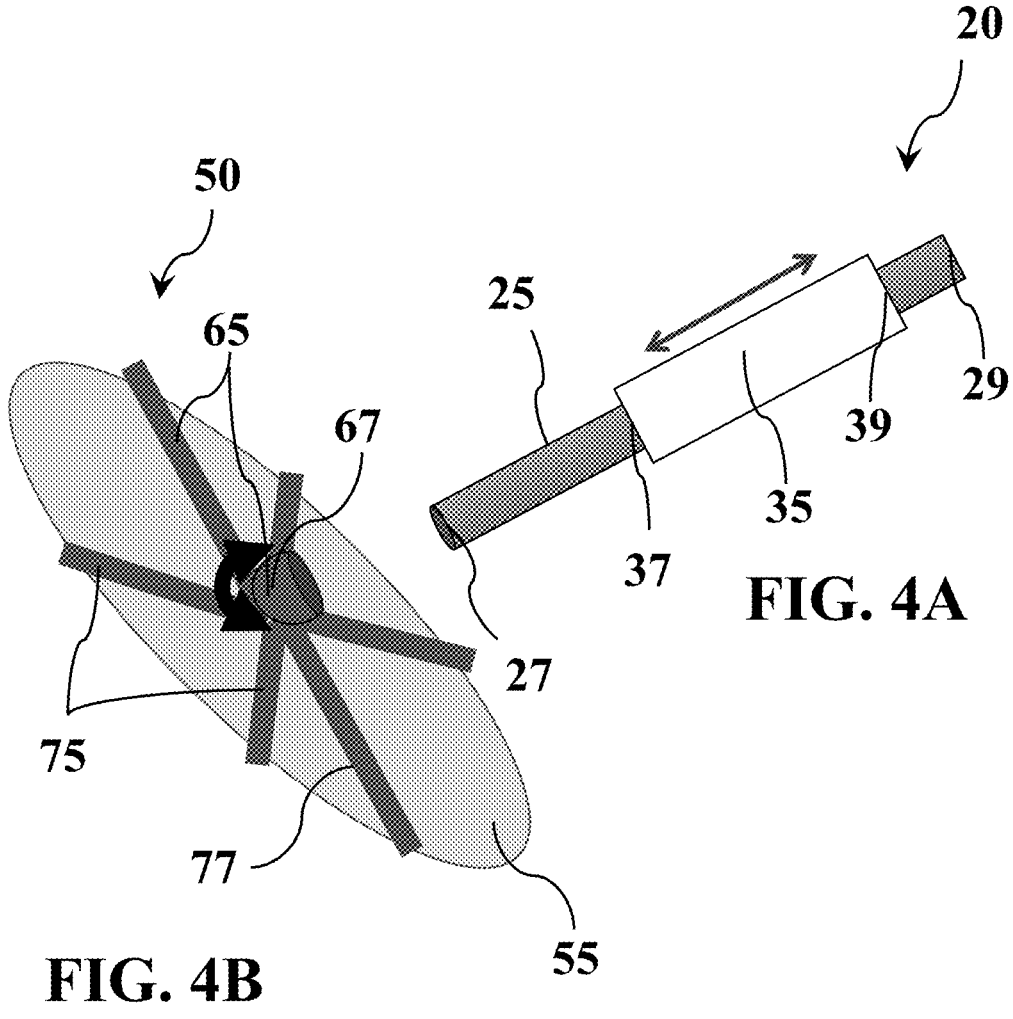
FIG. 4 is a drawing that shows an optional aspect of the various tissue repair and sealing devices disclosed herein, wherein a central coupler is configured to be rotatably attached to a deployable clasp, which permits the angular rotation of the graft. In one exemplary aspect presented in FIG. 4B, the central coupler is fabricated in a ball and socket configuration, which permits the detachable graft and clasp assembly to be oriented over a range of angles with respect to the applicator shaft FIG. 4A as may be required during an MIS procedure.

FIG. 4 illustrates an optional aspect of the various tissue repair and sealing devices disclosed herein wherein central coupler 67 is configured to be rotatably attached to deployable clasp 75 having a plurality of radial struts or spokes 77, which thereby permits its angular rotation of graft subassembly 55. In one exemplary aspect presented in FIG. 4B, central coupler 67 is fabricated in a ball and socket configuration, which permits the detachable graft and clasp assembly 50 to be oriented over a range of angles with respect to the applicator shaft 25 of applicator assembly 20 (FIG. 4A) as may be required during an MIS procedure (where access and visibility are constrained) to rotate the detachable graft and clasp assembly 50.

FIG. 5 illustrates an embodiment of the presently disclosed tissue repair and scaling device that is configured for use in surgical procedures (e.g., lumbar punctures and gastrostomies) to occlude a large-bore needle puncture or percutaneous ostomy site. In FIG. 5A is shown a tissue repair and sealing device comprising (a) an applicator assembly 20 having an applicator shaft 25 and a movably attached clasp retain and release member 35 and (b) a detachable graft and clasp assembly 50 having a graft subassembly 55 fixedly attached to a deployable clasp and coupler assembly 65, wherein the graft 57 is a conical occluder graft, wherein the applicator shaft 25 is fabricated out of a flexible material, and wherein the applicator shaft 25, central coupler 67, and graft 57 are configured with a central channel 123 to accommodate a guidewire. In certain aspects, the conical occluder graft 57 is comprised of a bioabsobable material. In FIG. 5B is shown the deployment of tissue repair and sealing device according to the embodiment presented in FIG. 5A, wherein a conical occluder graft 57 is positioned on an inner tissue surface and the radial struts or spokes 77 of a deployable clasp 75 are positioned on an outer tissue surface to apply pressure against the outer tissue surface, secure the conical occlude graft 57, and, thereby, repair a tissue fenestration (i.e., a puncture or ostomy site) and create a pressure-resistant, watertight seal.

Figures 6A, 6B:
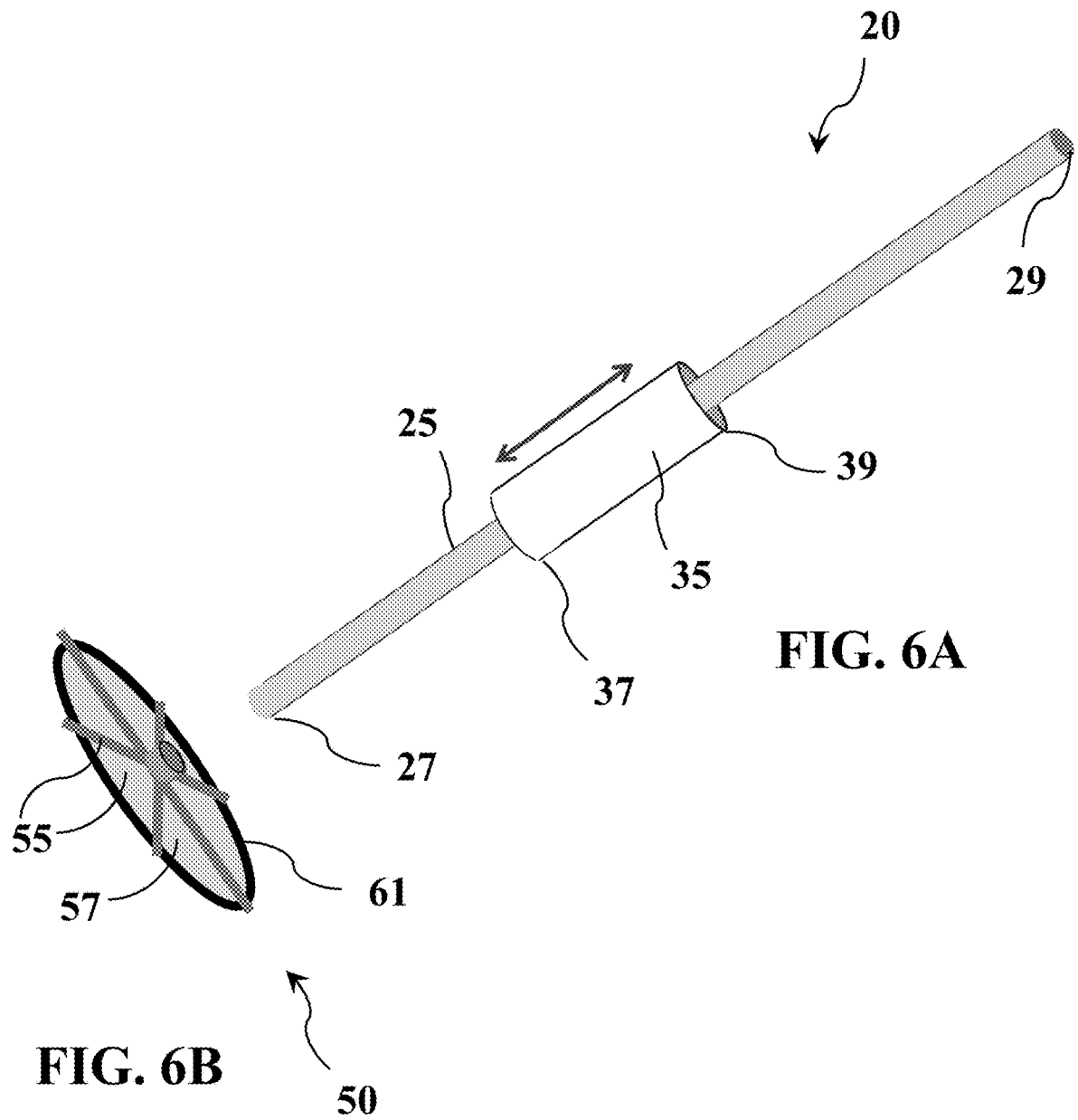
In FIG. 6A is shown an applicator assembly comprising an applicator shaft and a clasp retain and release member, wherein the clasp retain and release member is slidably connected to the applicator shaft.
FIG. 6B shows a detachable graft and clasp assembly comprises a graft subassembly that includes a form ring adhered to one surface of the graft and wherein the form ring has sufficient flexibility to permit the folding of the graft during insertion through a tissue fenestration and has sufficient rigidity to allow the graft to unfold (and assume its original shape) prior to positioning on an inner tissue surface. In some aspects of the present disclosure, which are described in further detain herein, the form ring comprises a bioresorbable material.

FIG. 6 illustrates an optional aspect of the various tissue repair and scaling devices disclosed herein wherein detachable graft and clasp assembly 50 comprises graft subassembly 55 that includes a form ring 61 that is fixedly adhered to graft 57 and wherein form ring 61 has sufficient flexibility to permit graft 57 to fold during insertion through a tissue fenestration and having sufficient rigidity to allow graft 57 to unfold once the tissue fenestration in traversed for positioning on an inner tissue surface. In some aspects of the present disclosure, form ring 61 comprises a bioresorbable material.

Figures 7A, 7B:
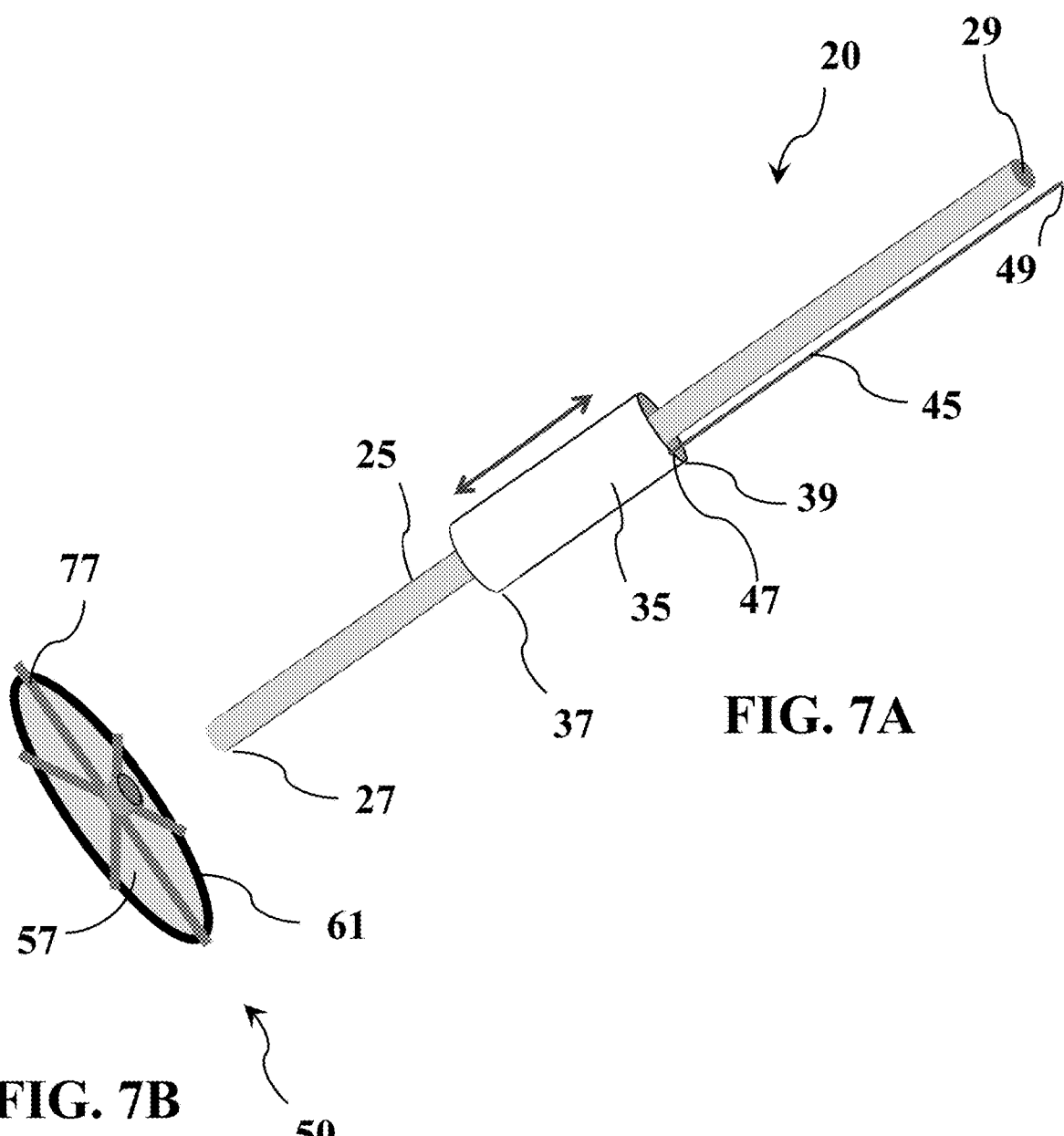
FIG. 7 is a drawing that shows an optional aspect of the tissue repair and scaling devices presented in FIGS. 1-5 wherein the applicator assembly (FIG. 7A) further comprises an actuator rod attached at one end to the clasp retain and release member and that extends past the applicator shaft to permit the release from an extended distance of the deployable clasp from the clasp retain and release member from detachable graft and clasp assembly (FIG. 7B).

FIG. 7 illustrates an optional aspect of the tissue repair and scaling devices presented herein, including FIGS. 1-4 and 6, which comprises applicator assembly 20 (FIG. 7A) and detachable graft and clasp assembly 50 (FIG. 7B), wherein applicator assembly 20 further comprises actuator rod 45 having a proximal end 47 and a distal end 49, wherein actuator rod 45 is attached at its proximal end 47 at the distal end 39 of clasp retain and release member 35. In operation, actuator rod 45, which extends past the distal end 29 of applicator shaft 25, permits the release of radial spokes or struts 77 of deployable clasp 75 (as depicted in FIG. 3) from the proximal end 37 of clasp retain and release member 35 from an extended distance from detachable graft and clasp assembly.

Figures 8A, 8B:
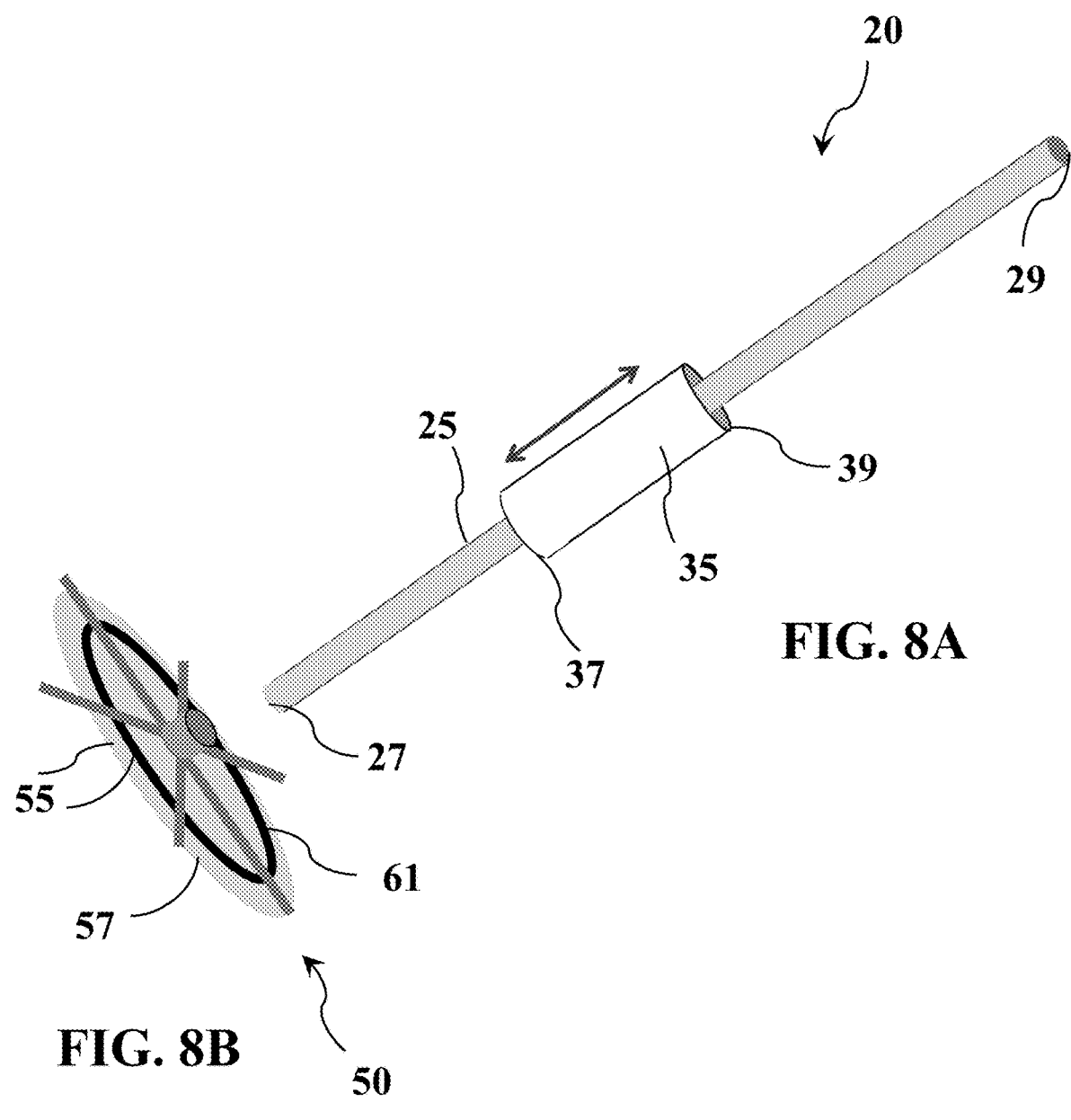
FIG. 8 is a drawing that shows an optional aspect of the tissue repair and scaling devices that are presented in FIGS. 1-4 and 6-7 comprising an applicator assembly (FIG. 8A) and a detachable graft and clasp assembly (FIG. 8B), wherein the detachable graft and clasp assembly comprises a graft subassembly that includes a form ring fixedly adhered to the graft and wherein the form ring has sufficient flexibility to permit the graft to fold during insertion through a tissue fenestration and has sufficient rigidity to allow the graft to unfold prior to positioning on an inner tissue surface (as presented in FIG. 19) and wherein the graft overhangs the form ring to improve the adherence of the graft to an inner tissue surface.

FIG. 8 illustrates an optional aspect of the tissue repair and scaling devices that are presented herein, including FIGS. 1-4 and 6-7, which comprises applicator assembly 20 (FIG. 8A) and detachable graft and clasp assembly 50 (FIG. 8B), wherein detachable graft and clasp assembly 50 comprises graft subassembly 55 that includes a form ring 61 that is fixedly adhered to graft 57, wherein form ring 61 has sufficient shape memory and superelasticity characteristics to permit graft 57 to fold during insertion through a tissue fenestration and to allow graft 57 to unfold once the tissue fenestration in traversed for positioning on an inner tissue surface (as presented in FIGS. 3B-3E) and wherein graft 57 overhangs form ring 61 to improve the adherence of graft 57 to an inner tissue surface.

Figure 9:
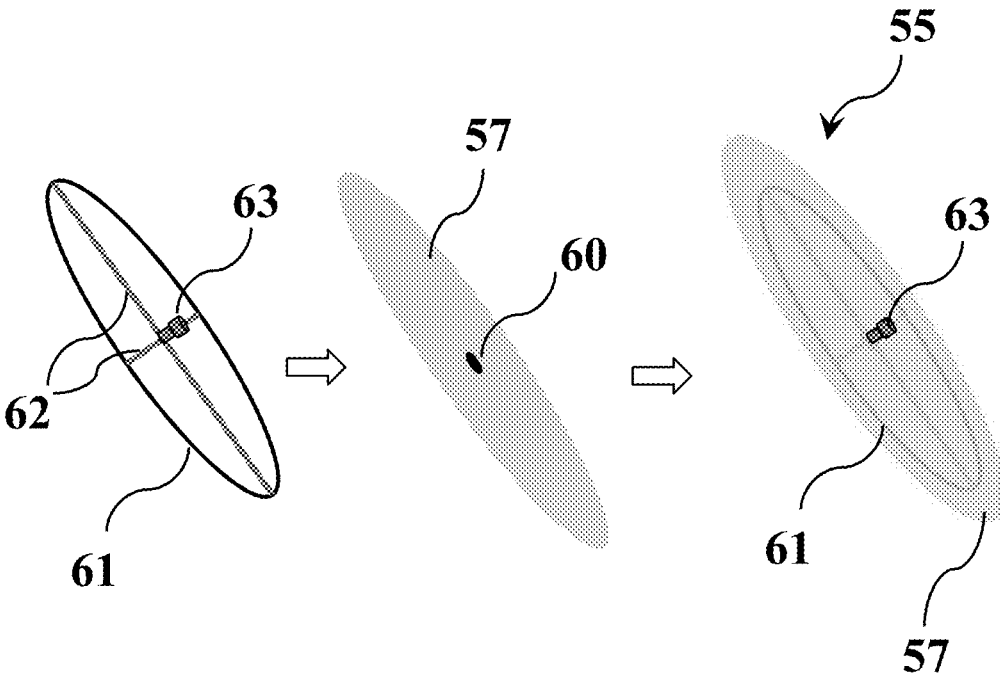
FIG. 9 is a drawing that shows the spatial arrangement of the component parts of an exemplary graft subassembly comprising a form ring fixedly adhered to the inner surface of a graft. The exemplary form ring is shown in combination with ring stabilizing members and a central coupler receiving member. The exemplary graft subassembly is shown with an orifice through which a central coupler receiving member protrudes.

FIG. 9 illustrates the spatial arrangement of the component parts of an exemplary graft subassembly 55 comprising form ring 61 fixedly adhered to inner surface 91 of graft 57. Exemplary form ring 61 is shown in combination with ring stabilizing members 62 and graft stabilizing prong 63. In the exemplary graft subassembly 55 is shown orifice 60 through which graft stabilizing prong 63 protrudes.

Figure 10:
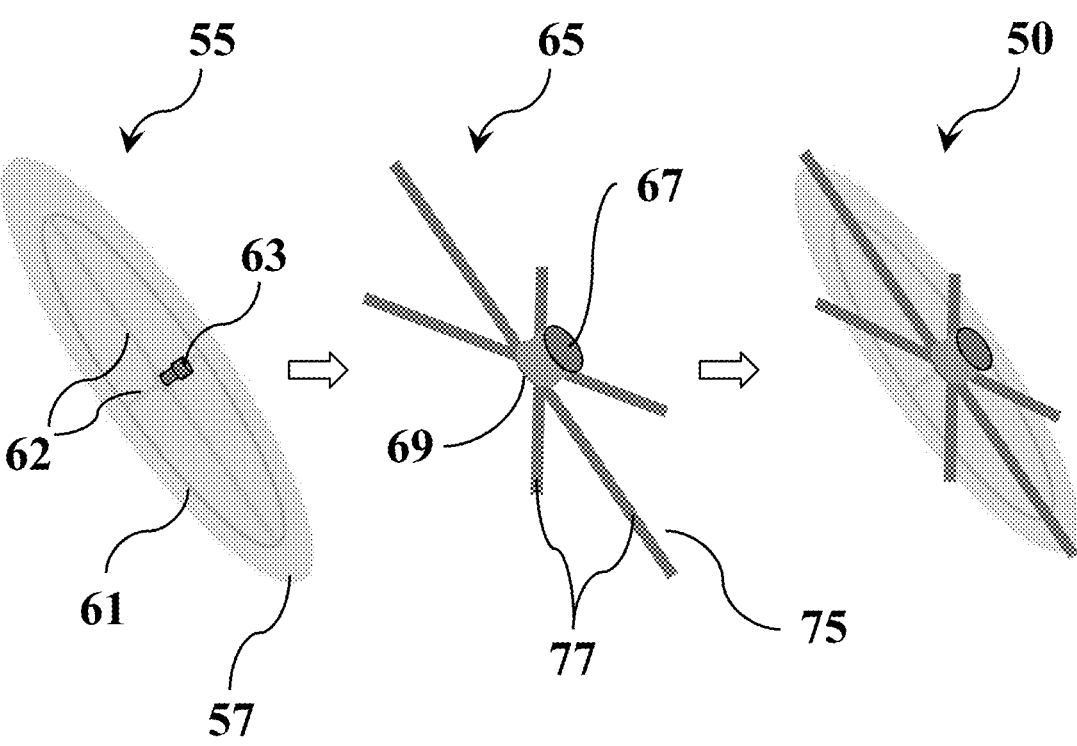
FIG. 10 is a drawing that shows the spatial arrangement of the component parts of an exemplary detachable graft and clasp assembly comprising a graft subassembly (as presented in FIG. 9) attached to a deployable clasp and coupler subassembly. The graft subassembly comprises a graft that is fixedly adhered at an inner surface to a form ring having ring stabilizing members and a central coupler receiving member. In this exemplary detachable graft and clasp assembly, the graft extends beyond the circumference of the form ring to improve its contact with and adherence to an inner tissue surface. Deployable clasp and coupler subassembly is shown with a deployable clasp having a plurality of radial spokes or struts that emanate from the central coupler. The deployable clasp and coupler subassembly is fixedly attached to central coupler to the graft subassembly via a central coupler receiving member.

FIG. 10 illustrates the spatial arrangement of the component parts of an exemplary detachable graft and clasp assembly 50 comprising graft subassembly 55 (as presented in FIG. 9) attached to deployable clasp and coupler subassembly 65. As shown in FIG. 10, graft subassembly 55 comprises graft 57 fixedly adhered at an inner surface to form ring 61, form ring stabilizing members 62, and graft stabilizing prong 63. In this exemplary detachable graft and clasp assembly 50, graft 57 extends beyond the perimeter of form ring 61 to improve its contact with and adherence to an inner tissue surface. Deployable clasp and coupler subassembly 65 is shown with a deployable clasp 75 having a plurality of radial spokes or struts 77 that emanate from the proximal side 69 of central coupler 67. Deployable clasp and coupler subassembly 65 fixedly attaches at the proximal side 69 of central coupler 67 (shown in FIG. 11) to graft subassembly 55 via graft stabilizing prong 63.

Figure 11:
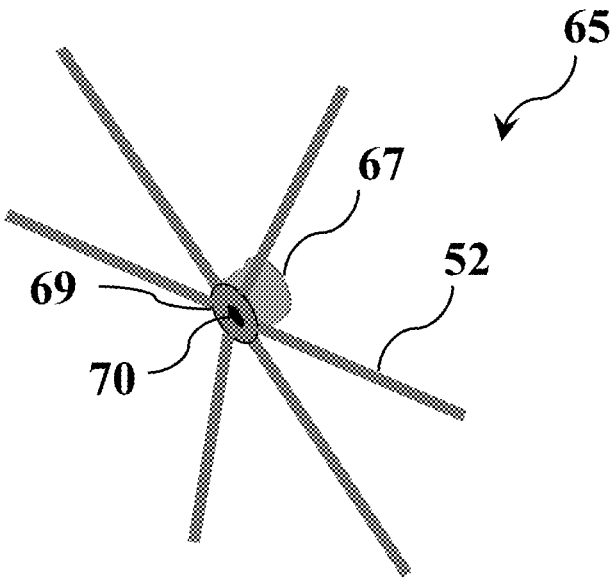
FIG. 11 is a drawing that presents a view of deployable clasp and coupler subassembly that shows a recess in the central coupler for attaching the center of the deployable clasp and coupler subassembly to the center of the graft subassembly at a central coupler receiving member as shown in FIG. 10.

FIG. 11 illustrates a view of deployable clasp and coupler subassembly 65 showing recess 70 at the proximal side 69 of central coupler 67 for attaching the center of deployable clasp and coupler subassembly 65 to the center of graft subassembly 55 at graft stabilizing prong 63 as shown in FIG. 10.

Figure 12:
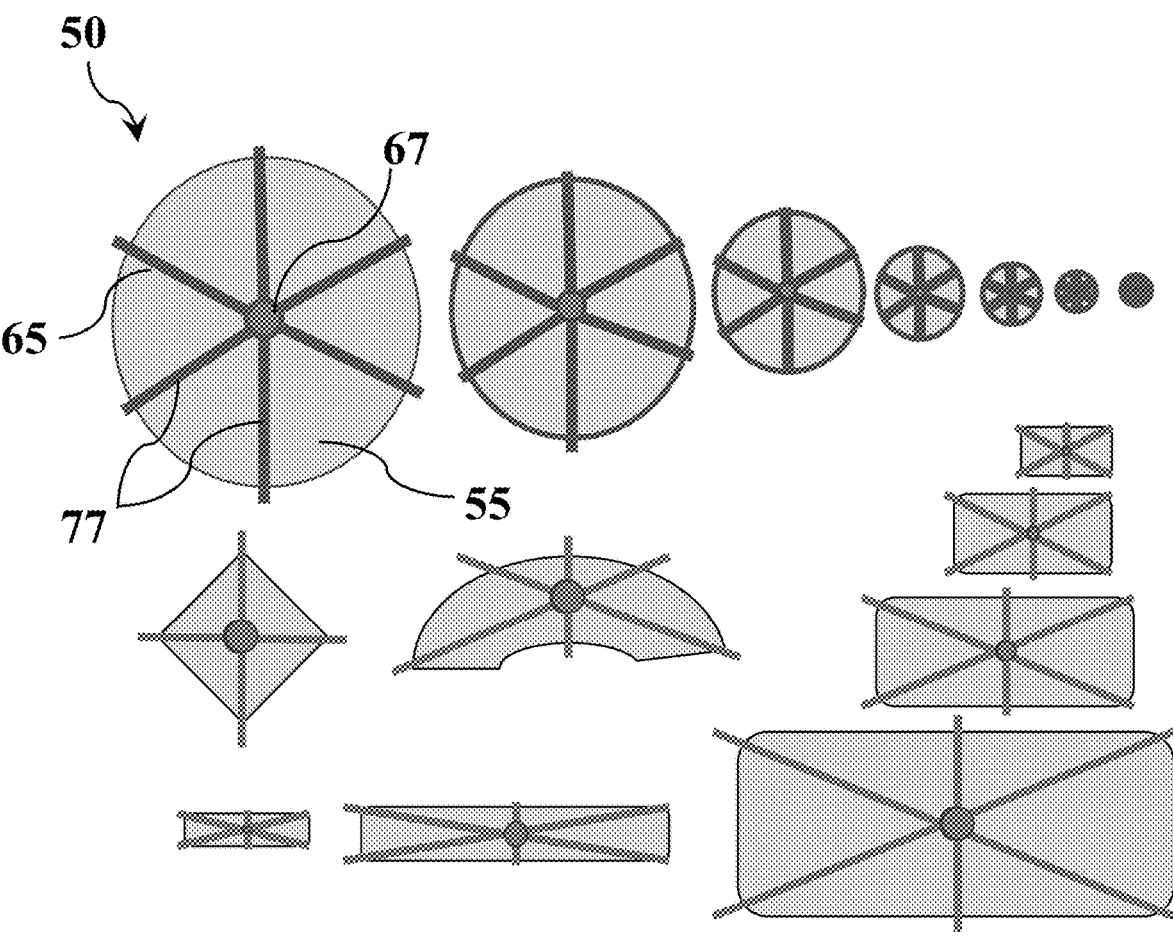
FIG. 12 is a drawing that shows representative configurations of a detachable graft and clasp assembly comprising a graft subassembly (with or without a form ring or one or more ring stabilizing members) and a deployable clasp and coupler subassembly comprising a central coupler and a deployable clasp having a plurality of radial spokes or struts emanating radially from a central coupler.

FIG. 12 illustrates representative configurations of detachable graft and clasp assembly 50 comprising graft subassembly 55 (with or without form ring 61 or ring stabilizing members 62) and deployable clasp and coupler subassembly 65 comprising a central coupler 67 and a deployable clasp 75 having a plurality of radial spokes or struts 77 emanating radially from central coupler 67. The various sizes, shapes, and materials used in the production of graft subassembly 55 and deployable clasp and coupler subassembly 65 permits the selection of a detachable graft and clasp assembly wherein the graft subassembly 55 can safely pass through a tissue fenestration, completely cover the defect on the inside tissue surface, and exhibit desirable bioresorbability, drug elution, and other biophysical properties for repairing the tissue fenestration and creating a pressure-resistant, watertight seal.

Regardless of the size, shape, and materials used in graft subassembly 55 and deployable clasp and coupler subassembly 65, detachable graft and clasp assemblies 50 are designed for interchangeably attaching to applicator assembly 20 at the proximal end 27 of applicator shaft 25 and each detachable graft and clasp assembly 50 is configured for retention by clasp retain and release member 35 of applicator assembly 20 (as depicted herein) and for release of detachable graft and clasp assembly 50 from clasp retain and release member 35 upon deploying applicator assembly 20.

It will be understood by those of skill in the art that the interchageability of detachable graft and clasp assemblies 50 permits the surgeon to rapidly assess the suitability of various graft subassembly configurations for repairing a given tissue fenestration during a surgical procedure at the time of positioning graft subassembly 55 on an inner tissue surface and deployable clasp and coupler subassembly 65 on an outer tissue surface.

FIG. 13 illustrates various optional configurations of detachable graft and clasp assembly 50, which include deployable clasp and coupler subassemblies 65 having a plurality of radial spokes or struts 77 (e.g., ranging from 6 radial spokes or struts to 12 radial spokes or struts) to permit the optimization of deployable clasp and coupler subassembly 65 for use in securing a graft subassemblies 55 to an inner tissue surface to rapidly repair tissue fenestrations of various size and within a variety of distinct tissues and to, thereby, reliably create a pressure-resistant watertight seal.

FIG. 13A illustrates detachable graft and clasp assembly 50 comprising (1) a graft subassembly 55 having a graft 57 (with or without a form ring 61 or ring stabilizing members 62) and (2) a deployable clasp and coupler subassembly 65 having a central coupler 67 and a deployable clasp 75 having six (6) radial spokes or struts 77.

FIG. 13B illustrates detachable graft and clasp assembly 50 comprising (1) a graft subassembly 55 having a graft 57 (with or without a form ring 61 or ring stabilizing members 62) and (2) a deployable clasp and coupler subassembly 65 having a central coupler 67 and a deployable clasp 75 having twelve (12) radial spokes or struts 77 to increase the force exerted by deployable clasp 75 when securing graft 57 to an inner tissue surface as can be required in a situation where there is a high pressure differential between the compartments inside versus outside of the fenestrated tissue.

FIG. 13C illustrates detachable graft and clasp assembly 50 comprising (1) a graft subassembly 55 having a graft 57 (with or without a form ring 61 or ring stabilizing members 62) and (2) a deployable clasp and coupler subassembly 65 having a central coupler 67 and a deployable clasp 75 having six radial spokes or struts 77, wherein each radial spoke or strut 77 further comprises a lateral extension 79 to improve the stability of deployable clasp and coupler subassembly 65 as may be required when a fenestrated tissue is friable at the site of attachment or exhibits multiple fenestrations.

FIG. 13D illustrates detachable graft and clasp assembly 50 comprising (1) a graft subassembly 55 having a graft 57

(with or without a form ring 61 or ring stabilizing members 62) and (2) a deployable clasp and coupler subassembly 65 having a central coupler 67 and a deployable clasp 75 having six radial spokes or struts 77, wherein each radial spoke or strut 77 further comprises a plurality of from two (2) to six (6) lateral extensions 79, which improves the stability of deployable clasp and coupler subassembly 65 as may be required when a fenestrated tissue is friable at the site of attachment or exhibits multiple fenestrations.

Figure 14:
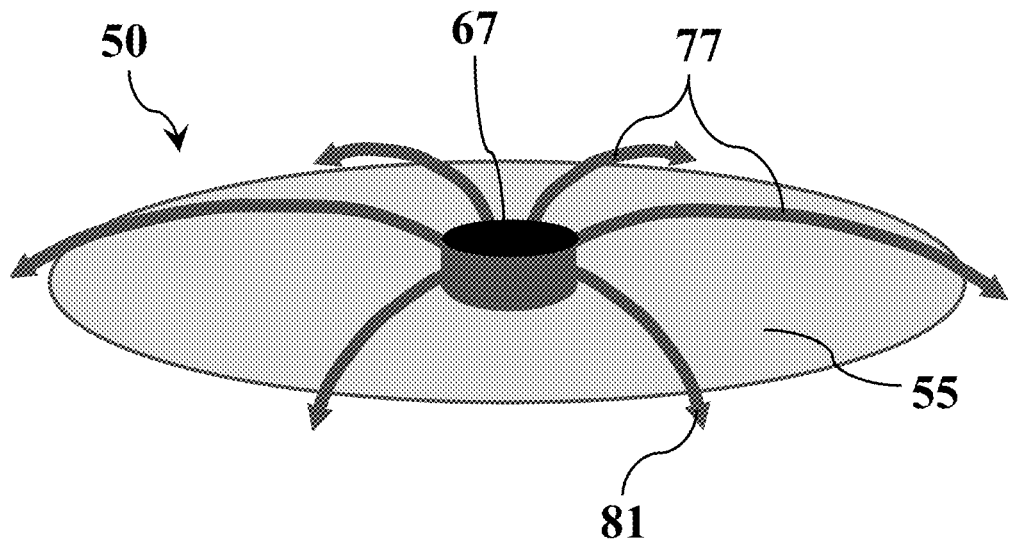
FIG. 14 is a line drawing that illustrates certain aspects of a detachable graft and clasp assembly according to certain embodiments of the tissue repair and sealing devices presented herein. Shown is a detachable graft and clasp assembly comprising (1) a graft subassembly having a graft (with or without a form ring or ring stabilizing members) and (2) a deployable clasp and coupler subassembly having a central

FIG. 14 illustrates detachable graft and clasp assembly 50 comprising (1) a graft subassembly 55 having a graft 57 (with or without a form ring 61 or ring stabilizing members 62) and (2) a deployable clasp and coupler subassembly 65 having a central coupler 67 and a deployable clasp 75 having six radial spokes or struts 77, wherein each radial spoke or strut 77 is fabricated to have increased thickness, to curve away from graft subassembly 55, and to include a barbs 81 on the distal end 80 at each radial spoke or strut 77 to improve the attachment of the construct to the underlying tissue. As illustrated in FIG. 14, detachable graft and clasp assembly 50 comprises arched spokes or struts and a dura lock channel and that may be fabricated out of PLGA or other suitable biocompatible and/or bioresormable material that exhibits one or more of the desired mechanical properties presented in Table 1. It will be appreciated by those having skill in the art that the increased thickness and curving of radial spoke or strut 77 and/or addition of barb 81 can be advantageously employed in less collatenous fenestrated tissue (e.g., bowel mucosa) where the curved struts exert greater pressure on the outer tissue surface and barbs 81 permit radial spokes or struts 77 strut tips to slightly penetrate the tissue at site of application.

FIG. 15 illustrates the spatial arrangement of the component parts of an exemplary graft subassembly 55 according to an alternate embodiment of the present disclosure that permits the use of autologous tissue grafts, or the substitution at the time of surgery of other non-rigid natural or synthetic graft materials in the tissue repair and scaling device. For non-rigid grafts, especially autologous grafts, accurate positioning of graft 57 against the inner surface of a fenestrated tissue and complete coverage of the entire opening can be difficult and graft 57 can fold or deform after passage through the fenestration.

Within certain aspects of this embodiment, graft subassembly 55 comprises a graft 57 having a central orifice 60 at or near the geometric center for receiving central coupler 67. Graft 57 is attached across its inner surface 91 to form ring 61, which comprises a plurality of ring stabilizing members 62 (1) each emanating radially from a central coupler 67 and (2) each having at its distal end a graft stabilizing prong 64. It will be understood that form ring 61 has sufficient flexibility to permit graft 57 to fold during passage through a tissue fenestration and sufficient rigidity to return graft 57 to its original flat shape for positioning on an inner tissue surface.

FIG. 16 illustrates the spatial arrangement of the component parts of certain aspects of an exemplary detachable graft and clasp assembly 50, according to an alternate embodiment of the present disclosure, wherein a second form ring 61 having a plurality of graft stabilizing prong alignment rings 68 radially distributed along its inside circumference is positioned over outer surface 92 of graft 57 such that it receives graft stabilizing prongs 64 that protrude from form ring 61 and that is attached to inner surface 91 of graft 57.

FIG. 17 illustrates the spatial arrangement of the component parts of certain aspects of an exemplary detachable graft and clasp assembly 50, according to an alternate embodiment of the present disclosure (See, FIGS. 15 and 16), wherein deployable clasp 75 comprises central coupler receiving ring 95 and a plurality of radial spokes or struts 77, each having a distal end 80, which emanate from central coupler receiving ring 95.

The detachable graft and clasp assembly 50 presented in FIGS. 15-17 will find particular utility in the presently disclosed tissue repair and sealing devices in those clinical applications wherein, during the course of a surgical procedure, it is desirable to substitute one graft 57, such as a first graft 57 comprising an autologous, homologous, heterologous or synthetic graft material, with a second graft 57, such as a second graft 57 comprising an autologous, homologous, heterologous or synthetic graft material. An autologous graft may, for example, comprise a patient tissue that is harvested contemporaneously with the surgical procedure. Thus, graft subassembly 55 may employ a graft 57 that is fabricated from tissue harvested from a patient's fascia, pericranium, mucosa or skin. Alternatively graft 57 may comprise a homologous, heterologous or synthetic graft material, which can substituted in the device by the method described for autologous grafts, according to the clinical setting.

In use, graft 57 is cut into a circular shape and fashioned with central orifice 60 to accommodate the passage of central coupler 67 through the center of graft 57. The graft is then attached at the outer circumference of its inner surface 91 to form ring 61 comprising a plurality of graft stabilizing prongs 64. A second form ring 61 comprising a plurality of graft stabilizing prong alignment rings 68 is attached to outer graft surface 92 along its circumference. A deformable clasp 75 is then placed over the second form ring 61 to secure deformable clasp 75 at central coupler receiving member 101 to central coupler 67.

FIG. 18 illustrates the folding of radial spokes or struts 77 that emanate at the proximal end from central coupler receiving member 101 of deployable clasp and coupler subassembly 65 in preparation for attaching to applicator assembly 20 and restraining with clasp retain and release member 35.

FIG. 19 is a schematic representation of an alternative embodiment of the tissue repair and sealing devices disclosed herein that is configured for providing continuous drug delivery to the fluid, tissue, or space within a body cavity, blood vessel, lumen or other structures within the body. In this embodiment, the graft 57 is either replaced with, or incorporates, a drug-eluting matrix, such as a bioresorbable drug-eluting matrix for delivery of a drug or agent to an inner tissue surface and/or for continuous release into the blood, body fluids, or tissue parenchyma in contact with the matrix.

FIG. 20 illustrates an embodiment of a graft assembly 55 in which graft 57 includes a plurality of biocompatible, non-ferromagnetic, passivated metal or metal alloy wires 64, which exhibit shape memory and superelasticity characteristics to permit the folding of the metal or metal alloy while retaining the capacity of graft 57 to unfold to a pre-folded state. FIG. 20A illustrates one aspect of this embodiment wherein the plurality of biocompatible, non-ferromagnetic, passivated metal or metal alloy wires 64 emanate radially from central coupler 67. As shown in FIG. 20B, the plurality of radial biocompatible, non-ferromagnetic, passivated metal or metal alloy wires 64 permit the folding of graft 57 away from central coupler 67 in an umbrella or parasol configuration. As shown in FIG. 20C, the plurality of radial biocompatible, non-ferromagnetic, passivated metal or metal alloy wires 64 also permits the further (or alternative)

folding of graft 57 in a spiral configuration to reduce its diameter for insertion in a clasp retain and release member 35.

FIG. 21A illustrates a tissue repair and sealing device of the present disclosure that comprises (a) an applicator assembly 20 having an applicator shaft 25, an elongated clasp retain and release member 35, and an actuator rod 45 connected to (b) a detachable graft and clasp assembly 50 having a graft subassembly 55 and a deployable clasp and coupler subassembly 65. According to this embodiment detachable graft and clasp assembly 50 utilizes a graft assembly 55 as presented in FIG. 20 wherein graft 57 includes a plurality of biocompatible, non-ferromagnetic, passivated metal or metal alloy wires 64, which exhibit shape memory and superelasticity characteristics, to permit the folding of the metal or metal alloy while retaining the capacity to unfold to a pre-folded state. FIG. 21B illustrates the tissue repair and sealing device of FIG. 21A in which both radial struts or spokes 77 and graft subassembly 55 are folded and inserted into clasp retain and release member 35. FIG. 21C illustrates the further compacting of graft subassembly 55 by folding in a manner that permits radial biocompatible, non-ferromagnetic, passivated metal or metal alloy wires 64 to adopt a spiral configuration, which is advantageous for fenestration repairs tissues having limited space beneath the tissue barrier.

1. Grafts for Use in Tissue Repair and Sealing Devices

Within certain aspects, the tissue repair and sealing devices disclosed herein comprise a graft that is either directly incorporated (i.e., "integrated") into the detachable graft and clasp assembly or is substituted at the time of surgery using the form rings as described herein. Tissue repair and sealing devices according to this disclosure may employ a fixed central coupler that maintains the detachable graft and clasp assembly in a perpendicular orientation relative to the applicator assembly or may employ an adjustable central coupler that permits movement of the detachable graft and clasp assembly relative to applicator assembly for use in enhancing the visibility of the tissue fenestration and nearby structures.

As used herein, the term "graft" refers, generally, to tissues, membranes, meshes, matrices, and the like that exhibit suitable biophysical properties and are of the appropriate size, shape, and other dimensions for adhering to inner tissue surfaces, repairing tissue fenestrations, and creating pressure-resistant, watertight seals. "Grafts" may derive from natural sources such as animal organ tissues and tissue barriers and include tissues from a donor that exhibit a defined genetic relationship to tissues from a recipient such as, for example, autografts (tissue obtained from patient), isografts (tissue obtained from a monozygotic twin), allografts (tissue obtained from another person), or xenografts (tissue obtained from a non-human animal species). Grafts from such natural sources may be autologous, homologous, or heterologous and may incorporate one or more synthetic material.

As used herein, the term "synthetic mesh" refers to a graft made from non-biologic materials including poly(ethylene terephthalate) (a/k/a Dacron®) or expanded polytetrafluoroethylene (ePTFE, Goretex®) and are described in Patera and Schoen, Biomaterials Science pp. 470-494 (Elsevier Academic Press, San DEieto, CA (2004)). "Synthetic meshes" are often permanent in nature, do not undergo bioresorption, and are associated with chronic inflammation and foreign body reactions, firmness and fibrosis, and infection. Schmatz, *Cureus* 10(1):e2127 (2018) provides a report on surgical experience with an synthetic, biosorbable graft material that has received FDA approval.

As used herein, the term "biologic mesh" refers to a graft that is derived from animal tissue, typically human or porcine dermis, and processed to an acellular, porous extracellular matrix scaffold of collagen and elastin. Often a "biological mesh" contains growth factors from the source tissue, which attract endothelial cells and fibroblasts, which release additional chemoattractants that signal the migration of other structural cells. The three-dimensional nature and porosity of "biological meshes" allow cells (mainly fibroblasts and inflammatory cells) to enter the mesh and adhere and undergo a cycle of remodeling consisting of degradation of the biologic mesh and regeneration of the collagen scaffold with host tissue. The balance of this degradation and rebuilding process, and the speed with which it occurs, influences the ultimate strength and structure of the repaired tissue. "Biologic meshes" can be crosslinked to increase graft firmness, although greater cell infiltration is typically observed with biologic meshes that are not crosslinked. Crosslinking can also prevent collagen breakdown and inhibit macrophage migration, which poses and increased risk of infection.

As used herein, the term "dural substitute" refers to a graft, either synthetic or biologic, for use in sealing dural tissue fenestrations by absorbing and integrating onto the patient's tissue to prevent CSF leaks and to allow openings in the dura to heal after surgery. "Dural substitutes" that may be advantageously employed in the tissue repair and sealing devices disclosed herein include the Duraform® dural graft implant (Natus, Medical Inc., Middleton, WI), which is a collagen-based biocompatible material with high tensile strength that is manufactured from processed bovine tendons; the Biodesign® Dural Graft and Duraplasty graft (Cook Medical, Bloomington, IN), which employ a natural extracellular matrix (ECM) derived from porcine small intestinal submucosa (SIS); DuraGen® Matrix (Integra LifeSciences, Princeton, NJ), which is a collagen matrix; Cerafix dural graft®, which is a synthetic, resorbable material; PRECLUDE Dura Substitute®, which is an inert elastomeric fluropolymer (ePTFE): Lyoplant Onlay Graft®, which is an absorbable collagen bilayer: Neuro-Patch Dural Graft®, which is microporous fleece; SEAMDURA®, which is a copolymeric film layered with PGA; and Durepair™ Regeneration Matrix (Medtronic, Minneapolis, MN), which is a non-synthetic collagen matrix derived from Type III fetal bovine tissue.

As used herein, the term "drug eluting graft" refers to graft materials that incorporate a drug eluting matrix to provide controlled focal drug release. Han and Lelkes, *Focal Controlled Drug Delivery, Advances in Delivery Science and Technology* (Springer, Boston, 2014).

As used herein, the term "non-resorbable" refers to materials that are not broken down and absorbed by the body, and thus are intended for long-term, structural applications. "non-resorbable" materials include implantable polymers, such as polyethylene and polyketones (PEEK), phase pure $\beta$ Tricalcium phosphate (TCP), and hydroxyapatite (HA).

In one embodiment, the graft material without support is flexible enough to be passed through the tissue defect, but also firm enough to retain its shape during positioning. In another embodiment, there is a thin bioresorbable form ring bonded to the outer circumference of the graft 5, which is flexible enough to deform during passage through the defect, then return to its original shape on the inner surface of the tissue. Attached to the center of the graft is a coupling component 6, allowing attachment and detachment of the applicator shaft.

In certain deployable devices according to these embodiments, the deployable clasp is fabricated from a flexible, bendable, and compressible material. Within further aspects, the flexible, bendable, and compressible material is a bioresorbable material, such as a bioresorbable material comprising one or more biopolymer, including one or more biopolymer that is selected from the group consisting of a polylactide (PLA), a polyglycolide (PGA), a polylactide-co-D, L lactide (PDLLA), a polylactide-co-glycolide (PLGA), a polylactide-co-caprolactone (PLCL), a polycaprolactone (PCL), a polydioxanone (PDO), and a polylactide-co-trimethylene carbonate (PL-TMC).

Exemplified herein are deployable devices that comprise a deployable clasp having a plurality of flexible spokes or struts that emanate radially from the coupler wherein the deployable clasp exhibits suitable biophysical properties, size, shape, and dimensions to secure a graft that is positioned on an inner tissue surface and a clasp that is positioned on an outer tissue surface to, thereby, repair a tissue fenestration and create a pressure-resistant, watertight seal.

In certain deployable devices according to these embodiments, the graft comprises a flexible, bendable, firm, and compressible material. In some aspects of these embodiments the graft exhibits shape memory and superelasticity characteristics. Grafts according to these embodiments, when used in combination with a deployable clasp, are suitably employed for the repair of tissue fenestrations and creation of pressure-resistant, watertight seals when the graft is positioned on an inner tissue surface and secured with a deployable clasp on an outer tissue surface.

In certain aspects, a graft according to these embodiments can be an autograft, an isograft, an allograft, or a xenograft. In other aspects, the graft comprises a tissue, a membrane, a mesh, a matrix. In further aspects, the graft comprises a material that is an autologous, homologous, or heterologous material. In yet other aspects, the graft comprises one or more synthetic material, including one or more synthetic materials selected from the group consisting of poly(ethylene terephthalate) and expanded polytetrafluoroethylene (ePTF). In still further aspects, the graft comprises a material that is derived from an animal tissue, such as an animal tissue that is selected from the group consisting a human tissue, a bovine tissue, and a porcine tissue or an animal tissue that is selected from the group consisting of dermis, and intestine. Grafts according to these embodiments may comprise an acellular, porous extracellular matrix scaffold of collagen, elastin, and, optionally, a growth factor. In some aspects, grafts according to these embodiments comprises a mesh having a porosity that is sufficient to allow cells to enter, adhere, and undergo a cycle of remodeling.

In other aspects, grafts according to these embodiments are fabricated out of a flexible, bendable, firm, and compressible material that is a bioresorbable material, including a bioresorbable material comprising one or more biopolymer, such as a biopolymer that is selected from the group consisting of a polylactide (PLA), a polyglycolide (PGA), a polylactide-co-D, L lactide (PDLLA), a polylactide-co-glycolide (PLGA), a polylactide-co-caprolactone (PLCL), a polycaprolactone (PCL), a polydioxanone (PDO), and a polylactide-co-trimethylene carbonate (PL-TMC).

In further aspects, grafts according to these embodiments comprise a dural substitute, such as, for example, a dural substitute that is selected from the group consisting of Duraform® dural graft implant, Biodesign® Dural Graft, DuraGen® Matrix, Cerafix dural graft®, PRECLUDER, Lyoplant Onlay Graft®, Neuro-Patch Dural Graft®, SEAM-DURA®, and Durepair™ Regeneration Matrix.

The devices and methods described herein may be applied to direct visual, percutaneous, or endoscopic repair and scaling of multiple tissues in the body. In addition, the device and methods described herein may be modified to address problems specific to the nature, condition and surgical exposure of the fenestrated tissue, including variations of the clasp material and orientation, a component to enable the intraoperative substitution of different graft materials, variations in the size and shape of the graft-clasp unit, and percutaneous or endoscopic repair and sealing of punctures or ostomies using a flexible applicator with or without guide wire.

Prior to using the repair and sealing device, the deployable clasp is folded and inserted into the slidably attached clasp retain and release member. Upon positioning of the graft on the inner tissue surface of the fenestrated tissue and the clasp on the outer tissue surface, the device is deployed by sliding the clasp retain and release member along the applicator shaft toward its distal end. When the device is deployed, the clasp struts or spokes are released from the clasp retain and release member and contact the outer tissue surface of the fenestrated tissue, thereby securing the graft and clasp in place to repair the tissue fenestration and create a watertight seal.

Additional modifications of the tissue repair and sealing device are described herein which address specific technical problems encountered in MIS surgery. These include variations in graft-clasp unit size and shape, a rotational attachment at the coupling device to enable positioning of the graft relative to the applicator to improve line of vision and access, variations in the strut materials and configuration, use of a flexible applicator and guide wire channel for use of the device in endoscopic or percutaneous procedures, and the incorporation of drug-eluting matrix materials in the graft component to provide continuous drug delivery at the site of application.

Thus, within certain embodiments, the tissue repair and sealing devices described herein incorporate a drug-eluting matrix to provide a continuous release of drugs to fluids and tissues at the site of tissue repair and scaling. In FIG. 19 is illustrated an exemplary tissue repair and scaling device in which graft 57 incorporates, or replaced with, a bioresorbable drug-eluting matrix to provide continuous drug delivery to the fluid, tissue or space within a body cavity, blood vessel, lumen or other structures within the body. By placing the drug-eluting matrix on the inner tissue surface, drugs or agents of many types can be locally and continuously released into blood, body fluids, or tissue parenchyma in contact with the matrix. The device can be either rigid or flexible as above, and passed under direct vision, by endoscope, or by a percutaneous approach using a guide wire.

The tissue repair and sealing devices may be adapted for use in securing a drug-eluting matrix, or a graft that incorporates a drug-eluting matrix, to an inner tissue surface including, without limitation, a tissue selected from dura, blood vessel, wall of esophagus, stomach or intestine, bladder wall, ureter, peritoneum, pleura, uterus, Fallopian tube, sclera of the eye, synovium, tympanic membrane or the capsule of a solid organ. Drugs that are incorporated into a drug-eluting matrix are released into the fluid or space contained by the tissue barrier (blood, cerebrospinal fluid, gastrointestinal contents, pleural cavity, peritoneal cavity, vitreous humor, inner car, Fallopian tube or joint space) and can be fashioned to disperse drugs at a pre-determined rate and concentration based upon the nature of the drug, the target tissue, and the chemical composition of the drug-eluting matrix to achieve the intended therapeutic effect.

In certain embodiments, tissue repair and sealing devices as disclosed herein may be advantageously employed to provide the continuous delivery of therapeutic agents to the bloodstream via arteries or veins for systemic distribution, to the bloodstream of arteries serving tissues distal to the implant to produce a localized effect in those downstream tissues while minimizing systemic distribution, or to fluids and/or tissues within a cavity or space. In certain applications, the drug that is released can act locally and directly upon the tissue to which the drug-eluting matrix, or graft comprising a drug-eluting matrix, is secured. Thus, the present disclosure contemplates the use of the tissue repair and sealing devices disclosed herein for use in providing the local delivery of agents to promote healing, to prevent local cellular proliferation (e.g., intimal proliferation or excess scar formation), to provide local anesthesia, to inhibit fertilization, or to treat infection with antimicrobial agents. For either embodiment, the bioresorbable nature of the repair and sealing device and drug matrix would eliminate the need for removal of the device at the conclusion of therapy.

Drug-eluting matrices and grafts have been described in the art that may be adapted for use in the presently disclosed tissue repair and scaling devices. Sec, for example, Alvarez-Lorenzo, *Journal of Pharmacology and Experimental Therapeutics* 370:544 (2019) (describing implantable smart drug release devices and materials); Concheiro, *Advanced Drug Delivery Review* 65(9):1188 (2013) (describing chemically cross-linked and grafted cyclodextrin hydrogels for use in drug-eluting medical devices); Nie, *Journal of Materials Chemistry* 7:6515 (2019) (describing integrated grafts comprising a biologically developed cartilage-bone interface of osteochondural defect repair); Zilberman, 299 (Springer-Verlag 2010) (reviewing drug-eluting medical implants, including drug-cluting matrices and grafts); Zilberman, *Journal of Controlled Release* 130(3):202 (2008) (describing antibiotic-eluting medical devices, including drug-eluting matrices and grafts); Zuckerman, *Gels* 6:9 (2020) (describing affinity-based release from cyclodextrin hydrogels); Richter, U.S. Pat. No. 7,048,714 (describing drug eluting medical devices having an expandable portion for drug release); Ding, U.S. Pat. No. 7,758,909, Lye, U.S. Patent Publication No. 2005/0070989, and Feng, U.S. Patent Publication No. 2008/0051881 (describing medical devices having a porous surface/layer for controlled drug release); Fennimore, U.S. Pat. No. 8,007,737 (describing antioxidants for the prevention of oxidation and degradation of drugs in drug-eluting medical devices); Atanasoska, U.S. Pat. No. 8,815,273 (describing drug-eluting medical devices having porous layers); Jennings, U.S. Pat. Nos. 9,605,175 and 10,314,912 (describing polymer coating compositions for use in medical devices); Gemborys, U.S. Pat. Nos. 9,801, 983 and 10,159,769 (describing medical devices for delivering bioactives to a point of treatment); Speck, U.S. Patent Publication No. 2011/0295200, Zilberman, U.S. Patent Publication No. 2016/0082161, and Hoffmann, U.S. Patent Publication No. 2011/0301697 (describing drug-eluting medical devices); Wong, PCT Patent Publication No. 2006/135609 (describing asymmetric drug-eluting hemodialysis grafts); Hanson, PCT Patent Publication No. 2008/156487 and Peck, PCT Patent Publication No. 2014/144188 (describing drug-cluting grafts for the local drug delivery to tissues). Each of these scientific and medical articles, patents, and patent publications is incorporated by reference herein in its entirety.

Drug-eluting matrices and grafts for use with the tissue repair and sealing devices disclosed herein may include one or more drugs or therapeutic agents including, for example, anti-infectives, antincoplastics, biologicals, cardiovascular agents, central nervous system agents, coagulation modifiers, gastrointestinal agents, genitourinary tract agents, hormones, immunologic agents, and metabolic agents as are well known and readily available in the art.

2. Biocompatible Materials for Use in Tissue Repair and Sealing Devices

The tissue repair and sealing device of the present disclosure comprises several biocompatible and/or bioresorbable elements configured to place a graft composed of natural or synthetic material on the inner surface of a tissue fenestration, at which time the graft is secured in place by release of a biodegradable clasp mechanism onto the outer surface of the tissue. Specifically, after passage of the graft through the tissue, and placement to completely cover the inner edges of the defect, a sliding cylindrical release mechanism on the applicator releases flexible bioresorbable clasps to deploy on the outer surface of the tissue, thereby securing the graft in place and providing an immediate watertight repair and scaling of the defect. The graft-clasp unit is applied using a detachable applicator shaft, which couples to the graft-clasp unit during graft placement, and is subsequently detached after the graft is secured.

The coupling device and clasp are composed of flexible bioaborbable material, which can be designed to apply the required tensile strength of the radial struts to secure the graft in place, and to be completely absorbed over a period of time which allows healing of the graft to the tissue.

As used herein, the term "bioresorbable" refers to materials that are broken down and absorbed by the body, and thus do not need to be removed manually. Biosorbable materials include (1) metals or their alloys, commonly magnesium-based and iron-based alloys and (2) polymers including biopolymers, and copolymers thereof, such as polylactide (PLA), polyglycolide (PGA), polylactide-co-D, L lactide (PDLLA), polylactide-co-glycolide (PLGA), polylactide-co-caprolactone (PLCL), polycaprolactone (PCL), polydioxanone (PDO), polylactide-co-trimethylene carbonate (PL-TMC) which can be customized to meet mechanical performance parameters, biocompatibility, and resorption rates.

Bioresorbable materials may be processed via traditional manufacturing methods including injection moulding, extrusion, compression moulding and machining. These polymers may also be used in novel manufacturing methods such as electrospinning, selective laser sintering, and fusion deposition modeling.

Biopolymers are available that exhibit good biocompatibility and produce degradation products that are eliminated from the body by metabolic pathways. PLA-based substrates are non-toxic and permit cells to differentiate to, for example, produce extracellular matrix components.

The mechanical properties of bioresorbable materials as well as the ability to prolong the degradation time makes polylactide (PLA) poly(lactide-co-glycolide) (PLGA,) and poly(L-lactide-co-D, L lactide) (PDLLA) particularly advantageous material options. As with suture anchors the addition of calcium phosphate helps promote bone growth, while absorbing at a slow enough rate to allow proper functionality of the implant. This controlled degradation is highly beneficial for this application as the ingrowth of bone tissue into the interference screw region allows for the native tissue fixation of the implanted tendon to occur resulting in better patient outcomes once the bioresorbable screw is completely degraded.

Poly L-lactide-co-D, L lactide (PDLLA) have good tensile strength, excellent mechanical and thermal properties. Since most of these applications do not require the implant to be placed under an elevated mechanical load, bioresorbable materials used for these treatments have focused on enhancing the biological response and ability to promote healthy bone regeneration without causing any adverse side effects upon degradation.

Poly dioxanone (PDO) polymers can be fabricated to provide materials having a desired degree of flexibility, good mechanical properties, and a fast to moderate degradation profile ranging from about 6 to about 12 months. Poly dioxanone (PDO) polymers are suitable for use in the manufacture of grafts, clasps, and central couplers according to the present disclosure, which are able to secure regenerating tissue systems in place long enough to allow for full healing after which the grafts and sutures degrade and become resorbed by the body. The degradation profile of the depends on multiple factors such as polymer crystallinity, molecular weight, sterilisation method, and in vivo environment.

Biopolymers that may be advantageously employed in the tissue repair and sealing devices disclosed herein exhibit one or more of the mechanical properties that are presented in Table 1.

TABLE 1

| Mechanical Properties of Biopolymers | | |
| --- | --- | --- |
| Mechanical Property | Lower Limit | Upper Limit |
| Young's Modulus | 1.75 GPa | 2.04 GPa |
| Specific Stiffness | 1.28 MN · m/kg | 1.54 MN · m/kg |
| Yield Strength (Elastic Limit) | 42 MPa | 55 MPa |
| Tensile Strength | 44.6 MPa | 52.1 MPa |
| Specific Strength | 30.9 kN · m/kg | 41.1 kN · m/kg |
| Elongation | 3.89% Strain | 5.6% Strain |
| Compressive Modulus | 1.75 GPa | 2.04 GPa |
| Compressive Strength | 53.6 MPa | 62.5 MPa |
| Flexural Modulus | 1.75 GPa | 2.04 GPa |
| Flexural Strength (Modulus of Rupture) | 60.9 MPa | 79.8 MPa |
| Shear Modulus | 0.625 GPa | 0.729 GPa |
| Shear Strength | 2.92 MPa | 3.4 MPa |
| Bulk Modulus | 2.93 Pa | 3.41 Pa |

Bioresorbable materials may be processed via traditional manufacturing methods including injection moulding, extrusion, compression moulding and machining. These polymers may also be used in novel manufacturing methods such as electrospinning, selective laser sintering, and fusion deposition modeling.

Biocompatable and bioresorbable materials have been described in the art that may be adapted for use in the presently disclosed tissue repair and scaling devices. Sec, for example, AZOM, *Biomaterials,* 2630 (2004) (describing the classifications and physical characteristics of biomaterials for use in medical devices); Evonik, Medical Plastics News (describing applications for bioresorbable materials in medical devices); Gilding, *Polymer* 20(12):1459 (1979) (describing biodegradable polymers, including polyglycolic acid (PGA) and polylactic acid (PLA) homo-and copolymers for use in medical devices, in particular in surgical devices); Kadam, *Medical Plastics News* 15:22 (2020) (discussing applications for medical polymers for developing efficient medical device technologies); Middleton, *Biomaterials* 21(23):2335 (2000) (discussing synthetic biodegradable polymers for use in orthopedic devices); Santos, *Tissue Engineering* 225 (Ed. Daniel Eberli, 2010) (reviewing bioresorbable polymers for use in tissue engineering); and Sheikh, *Materials* 8:5744 (2015) (reviewing biodegradable materials for use in bone repair and tissue engineering). Each of these scientific and medical articles is incorporated by reference herein in its entirety.

Within certain embodiments, the tissue repair and sealing devices disclosed herein may utilize a detachable graft and clasp assembly in which a graft subassembly and/or deployable clasp and coupler subassembly that incorporates a biocompatible, non-ferromagnetic, passivated metal or metal alloy in a graft 57, form ring 61, central couper 67, and/or deployable clasp 75 to provide or enhance the shape memory and superelasticity characteristics of those component parts the tissue repair and sealing device.

Suitable biocompatible, non-ferromagnetic, passivated metal or metal alloys for use in the tissue repair and sealing devices disclosed herein include, but are not limited to, cobalt-based alloys, pure titanium, titanium-based alloys, platinum-based alloys, molybdenum, tungsten, and tantalum alloys. Suitable passivated metal or metal alloy wires for use in detachable graft and clasp assemblies exhibit desirable shape memory and superelasticity characteristics such as those exhibited by nickel-titanium (Nitinol) and/or niobium-titanium.

Biocompatible, non-ferromagnetic, passivated metal or metal alloy have been described in the art that may be adapted for use in the presently disclosed tissue repair and sealing devices. See, for example, U.S. Pat. No. 8,349,249 ("Wachter") and U.S. Pat. No. 8,992,761 ("Lin"), which are incorporated by reference herein.

Methods for the Use of Tissue Repair and Sealing Devices

The present disclosure provides methods for the use of tissue repair and sealing devices in both MIS and non-MIS procedures to achieve the rapid repair of fenestrated tissues and the reliable creation of pressure-resistant watertight seals. The tissue repair and scaling devices disclosed herein comprise, in operable combination, (1) an applicator assembly comprising a clasp retain and release member having a proximal end and a distal end that is movably attached to an applicator shaft having a proximal end and a distal end and (2) a detachable graft and clasp assembly comprising a graft subassembly and a deployable clasp and coupler subassembly that is fixedly attached to the center of the graft.

Thus, within certain embodiments, methods for the use of tissue repair and sealing devices disclosed herein comprise: (1) selecting a detachable graft and clasp assembly, as disclosed herein, (2) attaching the detachable graft and clasp assembly to an applicator assembly comprising an applicator shaft and a clasp retain and release member, (3) folding the clasp and inserting into the clasp retain and release member (4) positioning the graft on an inner tissue surface, (5) positioning the deployable clasp on an outer tissue surface, (6) securing the graft to the inner tissue surface by releasing the deployable clasp onto the outer surface, (7) repairing a tissue fenestration, and (8) creating a pressure-resistant, watertight seal.

FIGS. 3B-3E illustrate a method for the use of a tissue repair and sealing device comprising graft subassembly and a deployable clasp and coupler subassembly as illustrated in FIG. 1 and FIG. 2 to rapidly repair a tissue fenestration and create a pressure-resistant, watertight seal.

FIG. 3B illustrates steps in preparing an exemplary tissue repair and sealing device for use in repairing and sealing a tissue fenestration. Detachable graft and clasp assembly 50 is attached to applicator assembly 20 at the proximal end 27 of applicator shaft 25 and the folded radial struts or spokes 77 of deployable clasp and coupler subassembly 65 are retained at the proximal end 37 of clasp retain and release member 35. Prior to insertion of a graft subassembly 57 through a tissue fenestration, the radial struts or spokes 77 of a deployable clasp and coupler subassembly 65 are folded away from the graft subassembly 55 and along a center of axis) that passes through central coupler 67 and inserted into the proximal end of the clasp retain and release member 35.

The graft is brought close to the defect under direct, microscopic or endoscopic vision, to determine the optimal size and shape of the graft subassembly 55 with relation to the size and shape of the fenestration. The central coupler 67 on the deployable clasp and coupler assembly 65 allows the rapid exchange and selection of detachable graft and clasp assemblies 55 by the surgeon to provide the optimal size, shape, and material for the graft to seal the tissue fenestration.

In FIG. 3C is shown the tissue repair and sealing device of FIG. 3B after insertion of the graft subassembly 57 through the tissue fenestration such that it covers the entire opening on the inside of the defect, then graft subassembly 57 is pulled back so that it contacts the inner surface of the fenestrated tissue while the deployable clasp and coupler subassembly 65 remains outside of the fenestrated tissue prior to deploying the tissue repair and sealing device. Re-expansion of the graft after passage through the fenestration may be facilitated by using a flexible, semi-rigid graft material, or by incorporating a flexible ring of bioresorbable material around the circumference of the graft (as shown in FIGS. 6-8 and FIGS. 13C-13D). Thus, graft subassembly 55 is configured to easily deforms to fit through a tissue fenestration and to re-expand to its original shape upon entering the inside of the tissue.

In FIG. 3D is shown the deploying of the tissue repair and sealing device. Once graft subassembly 55 is positioned on the inner surface and deployable clasp and coupler subassembly 65 is positioned on an outside tissue surface, the device is deployed by sliding the clasp retain and release member 35 toward the distal end 29 of applicator shaft 25 to, thereby, release the deployable clasp struts or spokes 77, which snap back to their original configuration and apply pressure against the outer surface of the fenestrated tissue, thereby securing the graft in an optimal position to seal the fenestration.

In FIG. 3E is shown the separation of the detachable graft and clasp assembly 50 from the applicator assembly 20 and the positioning of the deployable clasp and coupler assembly 65 against an outer tissue surface to secure the graft subassembly 55 to the inner tissue surface and, thereby, to rapidly repair the tissue fenestration and reliably create a pressure-resistant, watertight seal.

FIG. 5 illustrates an alternate embodiment of the tissue repair and sealing devices disclosed herein that is configured for sealing large-bore needle punctures (e.g., arterial puncture or lumbar puncture) or ostomies (surgical openings) into hollow body organs or cavities, usually associated with drainage of fluid through a needle or the placement of a tube or cannula for infusion or drainage (e.g., lumbar drain, gastrostomy tube, thoracentesis drain, abdominal paracentesis, arterial catheter, suprapubic cystostomy) that is created for infusion or drainage tubes. In this embodiment, applicator shaft 25 is fabricated out of a flexible material to enable the passage of the tissue repair and sealing device through an endoscope, or by a percutaneous route using a guide wire passed through an internal channel in the detachable graft and clasp assembly 50 and applicator shaft 25.

Figure 5A:
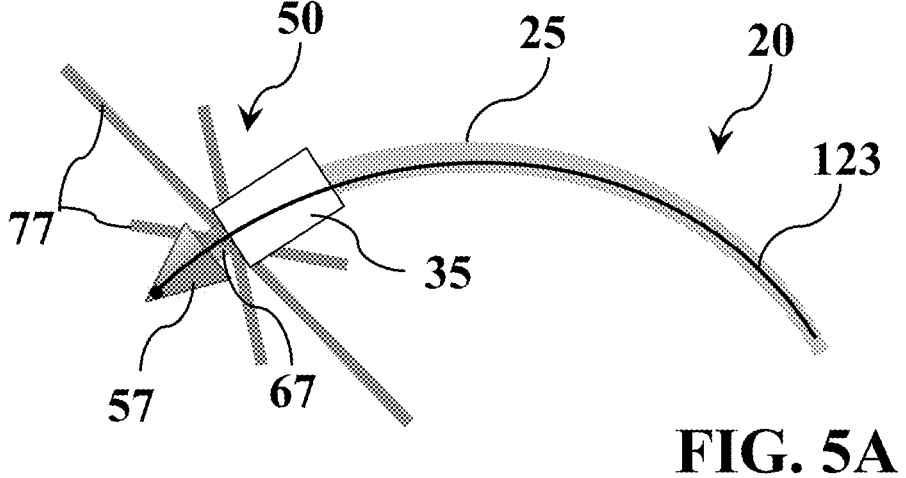
In FIG. 5A is shown a tissue repair and scaling device comprising an applicator assembly having an applicator shaft and a clasp retain and release member and a detachable graft and clasp assembly having a graft subassembly and a deployable clasp and coupler assembly, wherein the graft is a conical occluder graft, wherein the applicator shaft is fabricated out of a flexible material, and wherein the applicator shaft, central coupler, and graft are configured with a central channel to accommodate a guidewire. In certain aspects, the conical occluder graft is comprised of a bioabsobable material.
Figure 5B:
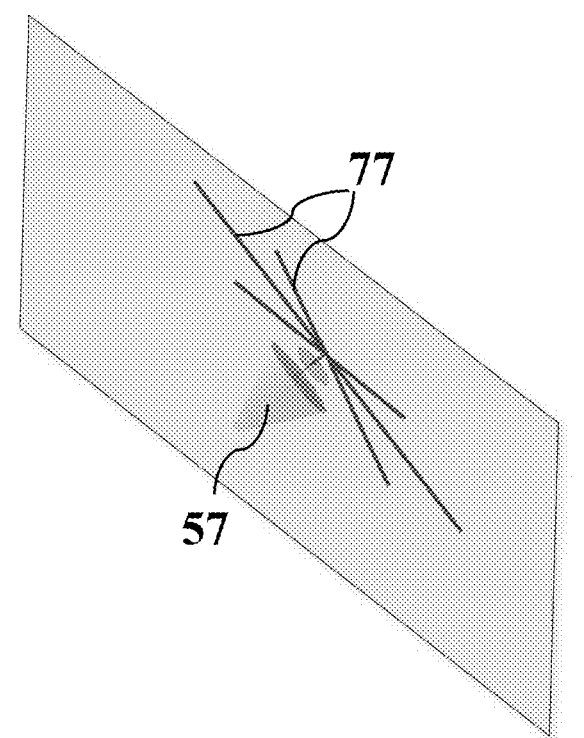
In FIG. 5B is shown the deployment of tissue repair and sealing device according to the embodiment presented in FIG. 5A, wherein a conical occluder graft is positioned on an inner tissue surface and the radial struts or spokes of a deployable clasp are positioned on an outer tissue surface to apply pressure against the outer tissue surface, secure the conical occlude graft, and, thereby, repair a tissue fenestration (i.e., a puncture or ostomy site) and create a pressure-resistant, watertight seal.

FIGS. 5C-5G show an exemplary method by which a tissue repair and scaling device as shown in FIG. 5A and FIG. 5B is used to repair a tissue fenestration, such as, for example, a large-bore needle puncture defect, including a puncture of an arterial wall, dura, stomach, or pleura. In these tissues, a puncture, with or without placement of a drain or cannula through the needle, can lead to persistent leakage through the puncture site, causing significant morbidity (e.g., hematoma formation, cerebrospinal fluid leakage, peritonitis, or pneumothorax). As shown in FIGS. 5A and 5B, occluder graft 57 has a conical shape and is deformable such that it can pass along the guide wire through a small puncture in a tissue barrier and re-expand so that the base of the deformable conical occluder graft 57 completely covers the puncture on the inner surface of the tissue. The size of the occluder graft may be selected based upon the size of the defect to be sealed and may be comprised of a bioresorbable polymer, as described herein, and may further comprise a drug eluting component to provide the delivery of a drug to the site of the tissue fenestration.

Figures 5C, 5D, 5E:
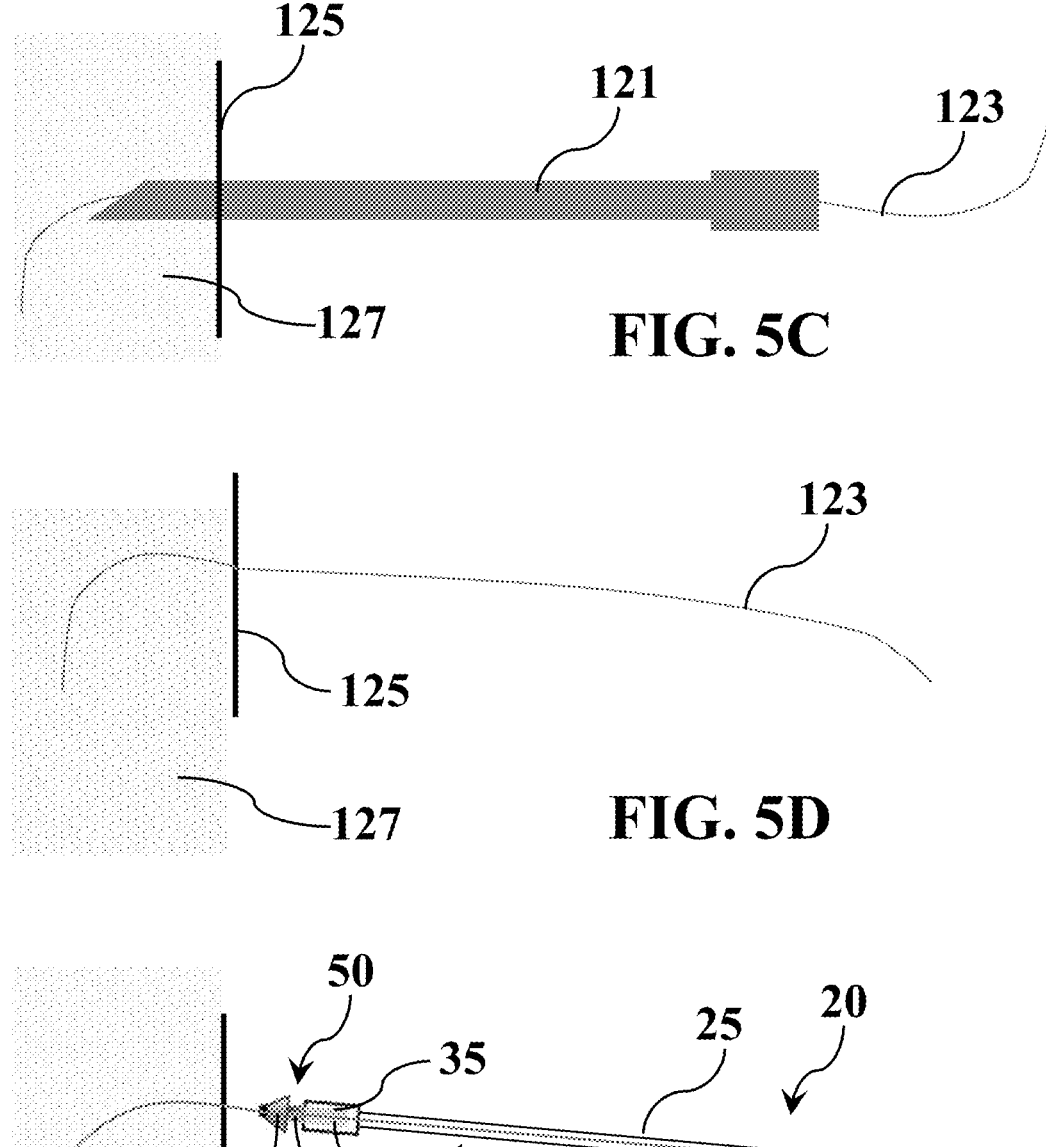
FIGS. 5C-5G show an exemplary method by which a tissue repair and scaling device as shown in FIG. 5A is used to repair a puncture site with the use of a guidewire.

FIG. 5C illustrates a large-bore needle 121 that is positioned through a tissue barrier 125 such as arterial wall, dura, stomach, or pleura, with the tip located in the lumen or cavity 127 inside the tissue barrier. A flexible guide wire 123 is then inserted into the lumen or cavity through large-bore needle 121. It will by understood that a guide wire may be positioned with a tubing or cannula that has been placed by a percutaneous approach (e.g., an arterial catheter, a lumbar spinal drain, a ventriculostomy, a pleurocentesis tube, a gastrostomy, or a suprapubic cystostomy). In an alternative aspect of this method, the guidewire may be passed through an indwelling catheter prior to its removal (not shown).

As shown in FIG. 5D, once guide 123 is inserted, large-bore needle 121 is removed leaving guide wire 123 in place and traversing the tissue fenestration. FIG. 5E illustrates the positioning of a tissue repair and sealing device by inserting the external end of guide wire 123 into the opening at the tip of conical occluder graft 57 and passing guide wire 123 through the central channel of conical occluder graft 57, central coupler 67, and flexible applicator shaft 25 of applicator assembly 20 and exiting at the distal end 29 of flexible applicator shaft 25. Prior to passing the tissue repair and scaling device along guide wire 123, the plurality of radial spokes or struts 77 are folded away from conical occluder graft 57 and inserted into the proximal end 37 of clasp retain and release member 35.

Figure 5F:
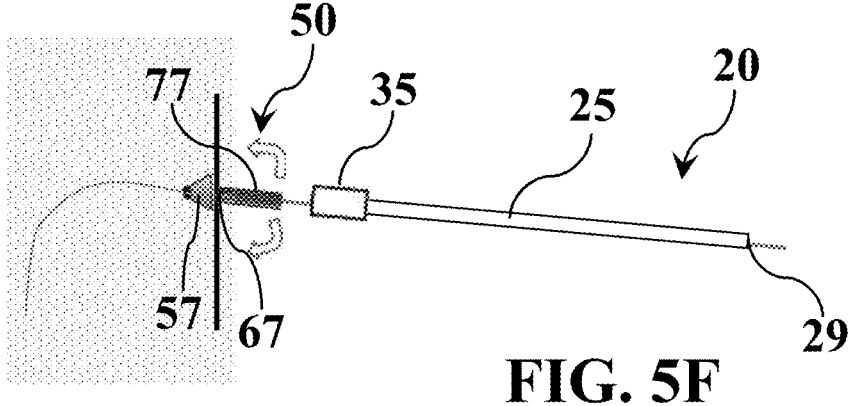
Figure 5G:
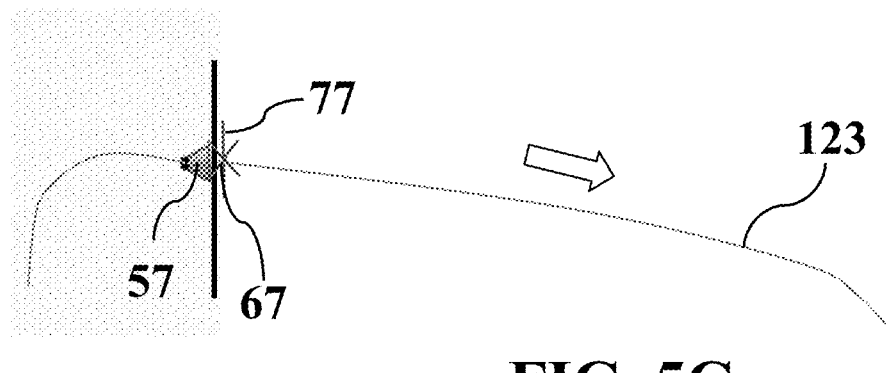

The tissue repair and sealing device is advanced along the guidewire 123 to the puncture site and the conical occluder graft 57 is passed through the puncture hole and positioned against the inner surface of the punctured tissue and the tissue repair and scaling device is deployed by moving the clasp retain and release member 35 toward the distal end 29 of the applicator shaft 25 to release the deployable clasp and coupler subassembly 65 (FIG. 5F). The plurality of radial struts or spokes 77 of deployable clasp 75 are positioned against, and apply pressure to, the outer tissue surface to secure the conical occlude graft 57, repair the puncture, and create a pressure-resistant, watertight seal. The applicator assembly 20 is detached from the detachable graft and clasp assembly 50, which remains at the puncture site, and the applicator assembly 20 is removed by sliding along the guidewire 123 after which the guidewire 123 is removed (FIG. 5G).

FIGS. 22A-22E illustrates a method for the use of a tissue repair and sealing device comprising a graft subassembly 55 and deployable clasp and coupler subassembly 65 as illustrated in FIGS. 20A-20C and FIGS. 21A-21C to rapidly repair a tissue fenestration and create a pressure-resistant, watertight seal. These tissue repair and sealing devices provide particular advantages in the repair of fenestrated tissues having a small tissue fenestration and/or that are friable in nature. In this embodiment, graft subassembly 55 is configured to include a plurality biocompatible, non-ferromagnetic, passivated metal or metal alloy wires 64, which exhibit shape memory and superelasticity characteristics, emanating radially from the center of graft 57. Thus, graft subassembly 55 is configured to easily deform to fit within clasp retain and release member 35 and to re-expand to its original shape upon entering the inside of the tissue and moving of clasp retain and release member 35.

FIG. 22A illustrates an exemplary tissue repair and sealing device prior to deploying. Detachable graft and clasp assembly 50 is attached to applicator assembly 20 at the proximal end 27 of applicator shaft 25 and the folded radial struts or spokes 77 of deployable clasp and coupler subassembly 65 are retained at the proximal end 37 of clasp retain and release member 35. Prior to insertion of graft subassembly 57 through a tissue fenestration, the radial struts or spokes 77 of a deployable clasp and coupler subassembly 65 are folded away from the graft subassembly 55 and along a center of axis that passes through central coupler 67 and inserted into the proximal end of the clasp retain and release member 35. In this embodiment is shown clasp retain and release member 35 that is elongated to accommodate graft subassembly 55, including graft 57 that comprises a plurality biocompatible, non-ferromagnetic, passivated metal or metal alloy wires 64 that emanate radially from the center of graft 57 and that is folded away from central coupler 67 in an umbrella or parasol configuration and restrained by clasp retain and release member 35.

The graft is brought close to the defect under direct, microscopic or endoscopic vision, to determine the optimal size and shape of the graft subassembly 55 with relation to the size and shape of the fenestration. The central coupler 67 on the deployable clasp and coupler assembly 65 allows the rapid exchange and selection of detachable graft and clasp assemblies 55 by the surgeon to provide the optimal size, shape, and material for the graft to seal the tissue fenestration.

In FIG. 22B is shown the tissue repair and sealing device of FIGS. 20A-20C and FIGS. 21A-21C after passage of the proximal end of clasp retain and release member 35 and graft subassembly 55 though the tissue fenestration. In FIG. 22C is shown the deploying of graft subassembly 55 by moving clasp retain and release member 35 along applicator shaft 25 toward its distal end and stopping when the proximal end of clasp retain and release member 35 reaches the outside of the fenestrated tissue at the site of the central coupler 67. In FIG. 22C, graft subassembly 55 is then pulled back so that graft 57 contacts the inner surface of the fenestrated tissue while the deployable clasp and coupler subassembly 65 remains outside of the fenestrated tissue and within clasp retain and release member 35.

In FIG. 22D is shown the release deployable clasp and coupler subassembly 65 from clasp retain and release member 35 by sliding the clasp retain and release member 35 toward the distal end 29 of applicator shaft 25 to, thereby, release the deployable clasp struts or spokes 77, which snap back to their original configuration and apply pressure against the outer surface of the fenestrated tissue, thereby securing the graft in an optimal position to seal the fenestration.

In FIG. 22E is shown the separation of the detachable graft and clasp assembly 50 from the applicator assembly 20 and the positioning of the deployable clasp and coupler assembly 65 against an outer tissue surface to secure the graft subassembly 55 to the inner tissue surface and, thereby, to rapidly repair the tissue fenestration and reliably create a pressure-resistant, watertight seal.

1. Methods for the Repair and Sealing of Fenestrations in the Dura Mater

Within certain embodiments, tissue repair and seal devices disclosed herein are configured for the repair and sealing of cerebrospinal fluid leaks due to fenestrations in the dura mater covering the brain and spine. Integrity of the dura is essential for containing cerebrospinal fluid within the central nervous system. Cerebrospinal fluid pressure is higher than that of adjacent tissues or body spaces.

This pressure differential perpetuates leakage of cerebrospinal fluid through even small fenestrations, and inhibits their spontaneous healing. Leakage of spinal fluid can lead to numerous complications, including wound infection, meningitis, cerebral herniation, intracranial bleeding, and headaches due to intracranial hypotension. Openings in the dura occur spontaneously (e.g., congenital defect, tumor, infection), purposefully (e.g. durotomy for craniotomy or spinal surgery, lumbar puncture, etc.), or inadvertently (dural laceration in spinal or endoscopic sinus surgery, trauma, etc.). Because the cerebrospinal fluid is under pressure with continued outward egress of cerebrospinal fluid through an unrepaired fenestration, as above, onlay grafts or glues tend to be displaced away from the outer surface of the dura and healing of the fenestration is impaired. Thus, spontaneous healing of dural openings not repaired at the initial surgery is poor, and subsequent measures to stop the cerebrospinal fluid leak frequently require re-hospitalization, re-operation, and/or other procedures such as harvesting additional tissue grafts or lumbar drainage catheters.

Current methods to seal dural fenestrations include one or combinations of several methods; direct suturing, placement of natural or synthetic grafts, tissue sealants, adjunctive tissue grafts to buttress the onlay graft repair, injection of epidural blood ("blood patch") or lumbar drainage. There are several commercially available dural substitutes, including human cadaveric dura, bovine and/or porcine pericardium, and various synthetic matrix formulations. These are usually applied as onlay grafts, occasionally with suturing or glue. The frequency of cerebrospinal fluid leaks due to incompletely sealed dural openings ranges considerably depending upon the nature of the procedure and the location, ranging from 1-2% in spinal surgery (higher for re-operations) to 10-15% for pituitary and certain posterior fossa operations. The future development of MIS approaches to the brain and spine are limited in large part by the difficulty in re-establishing integrity of the dura. A major limitation in the repair and sealing of planned or inadvertent dural openings for MIS procedures is the difficulty in suturing the dura. This is generally due to the inaccessibility for conventional suturing at the site of the durotomy and/or the friability of dura in certain locations. Also, the close proximity of critical neural structures (nerve roots, cranial nerves, spinal cord, brain, blood vessels) makes suturing hazardous in many settings, as passage of the needle through the dura can inadvertently damage these structures. Another application of the invention described herein for dural closure may be for open (non-MIS) procedures of the cranium and spine, wherein a planned incision in the dura is made to expose the underlying neural structures during craniotomy or laminectomy procedures. Suture closure of the dural incision is generally employed, but is time-consuming and often not watertight. Additionally, the device may utilize the fixed perpendicular orientation of the graft-clasp unit on the applicator shaft or an adjustable coupling device to enable rotation of the graft-clasp unit to facilitate visualization of the fenestration and nearby structures.

2. Methods for the Repair and Sealing of Spinal Dural Punctures

Within certain embodiments, tissue repair and seal devices disclosed herein are configured for the repair and sealing of spinal dural puncture sites for lumbar punctures and spinal drains. Such punctures can cause persistent leakage of cerebrospinal fluid into the adjacent peri-spinal tissue, causing intracranial hypotension manifest by incapacitating headaches. For example, the incidence of headache from cerebrospinal fluid leak can be as high as 80% following dural puncture for spinal anesthesia. Current methods for closure of dural puncture leaks include bed rest and or the use of an epidural blood patch. Percutaneous repair and sealing of spinal dural punctures using the tissue sealing device described herein is accomplished by passing the device with a flexible applicator shaft along a guide wire at the time of spinal drain or spinal puncture needle removal. The device is passed along the guide wire until the conical bioresorbable occluder graft passes through the puncture opening into the intradural space. The occluder graft is pulled back so that the base covers the puncture fenestration on the inner surface, after which applicator is withdrawn along the guide wire. The restraining cylinder withdraws with the applicator, releasing the grasp struts, which deploy on the outer dural surface of the puncture fenestration to secure the graft and provide an immediate watertight seal. Because the occlude graft is bioresorbable, it would not need to be removed.

3. Methods for the Repair and Sealing of Visceral Hollow Organ Fenestrations Within certain embodiments, tissue repair and seal devices disclosed herein are configured for the repair and sealing of fenestrations in the wall of visceral hollow organs, including but not limited to esophagus, stomach, small and large intestine, rectum, bladder, ureter, uterus and vagina. Such fenestrations occur both spontaneously (e.g. tumor, infection), purposefully (e.g. incision or biopsy of the organ during surgery), or inadvertently (laceration or puncture during surgery). Fenestrations in such hollow organ walls usually require repair to prevent intraperitoneal leakage of enteral contents or urine, or ingress of bacteria through uterus or vagina, which can lead to peritonitis or fistula formation. Rapid and watertight repair and sealing of such organs can be accomplished using the tissue repair and sealing device described herein at the time of the procedure, thus preventing leakage and subsequent infection or the need for re-operation. In any of these settings, the graft may consist of autologous, homologous, heterologous, or synthetic materials, either directly incorporated as an integrated graft-clasp unit, or substituted at the time of surgery using the bioresorbable graft frame and holder apparatus. Additionally, in any of these settings the device may utilize the fixed perpendicular orientation of the graft-clasp unit on the applicator shaft or an adjustable coupling device to enable rotation of the graft-clasp unit to facilitate visualization of the fenestration and nearby structures.

4. Methods for the Repair and Sealing of Punctures, Perforations or Ostomies Within certain embodiments, tissue repair and seal devices disclosed herein are configured for the repair and sealing of punctures, perforations or ostomies in abdominal hollow organs after biopsy or removal of a tube or cannula. Examples of the biopsy-related uses include perforations of esophagus, stomach, small or large intestine, or rectum occurring during trans-oral or trans-anal endoscopic biopsies, or perforations of the vagina and uterus, or bladder and ureters during trans-vaginal and trans-urethral endoscopic procedures, respectively. In another related embodiment, the tissue repair and sealing described device herein may be used for the percutaneous repair of an ostomy or needle puncture in a hollow organ wall, after removal of a drainage tube. This embodiment uses the flexible repair and sealing device advanced through and endoscope or over a guide wire, and may be used for external percutaneous tubes, drains, or cannulas removed from the esophagus, stomach, small or large intestine, rectum, or bladder (suprapubic tube). The graft component in these applications may include either flat grafts of natural or synthetic material, or conical occluder grafts. As above, the benefit of immediate sealing of the tube ostomy is the prevention of leakage of internal fluids into the peritoneum or through the skin via the percutaneous tube tract.

5. Methods for the Repair and Sealing of Body Cavity Fenestrations

Within certain embodiments, tissue repair and seal devices disclosed herein are configured for the repair and sealing of fenestrations of body cavities, including but not limited to peritoneum, pleural cavity, inner car or joint space. Drainage of the pleural cavity via thoracentesis can be complicated by pneumothorax, caused by ingress of air through the puncture site in the pleura. Similarly, percutaneous or endoscopic punctures of the peritoneum for surgical access or abdominal paracentesis (e.g. for drainage or dialysis) may subsequently leak along through the cutaneous incision. Similarly, surgical procedures of the car or joints may create fenestrations in the tympanic membrane or synovium, respectively. In these situations, the tissue repair and sealing device described herein, in either the rigid or flexible form with flat or conical graft, can immediately seal the puncture site and prevent subsequent complications. Additionally, the device may utilize the fixed perpendicular orientation of the graft-clasp unit on the applicator shaft or an adjustable coupling device to enable rotation of the graft-clasp unit to facilitate visualization of the fenestration and nearby structures.

6. Methods for the Repair and Sealing Defects in Body Facia

Within certain embodiments, tissue repair and seal devices disclosed herein are configured for the repair and sealing of fenestrations of defects in body fascia, including but not limited to abdominal wall, chest wall or muscle and ligament fascia. Defects in these fascial structures can lead to herniation of underlying tissues or wound breakdown. Repair of body fascia using the device described herein may include direct closure of the fascia in open (non-MIS) procedures using single or multiple graft-clamp components applied to the fascial edges, or in the case of a large defect, the incorporation of a free graft of natural or synthetic material, which is secured circumferentially to the defect edges using multiple graft-clasp units. In addition, the flexible or rigid tissue repair and scaling device may be used to close fenestrations in fascia via endoscope or by percutaneous approach. In any of these settings the device may utilize the fixed perpendicular orientation of the graft-clasp unit on the applicator shaft or an adjustable coupling device to enable rotation of the graft-clasp unit to facilitate visualization of the fenestration and nearby structures.

7. Methods for the Localized Delivery of Drugs and Other Agents

Within certain embodiments, tissue repair and seal devices disclosed herein are configured for the continuous, localized delivery of drugs and other agents from a drug-eluting matrix incorporated into, or replacing the graft component. Localized delivery of drugs provides several benefits; (a) the concentration of the drug is highest at the site of application, and untoward effects from systemic distribution of the drug are minimized; (b) the drug can be administered in adequate concentration to body compartments that are relatively inaccessible to the drug administered by intravenous or oral route (e.g. cerebrospinal fluid due to blood-brain barrier restriction, poorly perfused compartments such as abscess cavity); (c) continuous delivery ensures a therapeutic steady-state concentration of the drug without the peak and trough fluctuations which occur with intermittent administration; (d) patient compliance is not an issue; and (e) the drug-eluting matrix can be biodegradable and engineered to release a specific drug at a known rate and duration depending on the site of delivery. Many drug-eluting matrices are currently in clinical use, although most involve implantation of the matrix into subcutaneous or solid tissues. In the current embodiment, any category of drug or bioactive agent could be implanted and secured at any site in the body using the modified tissue repair and sealing device, depending upon the clinical setting and intended therapeutic effect.

The distribution of the drug would depend upon the site of application of the matrix. For example, a matrix placed on the inner surface of a blood vessel could provide systemic distribution for a venous implant site, or provide regional drug distribution to the downstream tissues perfused by an artery (e.g. a neoplasm or single organ). Additionally, a matrix placed on the inner surface of a tissue barrier could provide drug delivery to the fluid or cavity enclosed by the barrier (e.g. dural implant releasing drug into cerebrospinal fluid, peritoneal implant releasing drug into peritoneal cavity, or gastrointestinal implant releasing drug into the bowel). Also, the matrix placed on the inside of a barrier could release drugs to modulate the barrier itself (e.g. promoting healing, inhibiting scarring or hyperplasia, or local pain control). Finally, a matrix implant placed inside the capsule of a solid organ or tumor, in contact with the parenchyma, could provide local drug delivery to that part of the organ or tumor (e.g. kidney, pituitary, malignant or benign tumor). As above, this application of the repair and sealing device could be applied to nearly every category of drugs and every body organ and tissue type.

While various embodiments have been disclosed herein, other embodiments will be apparent to those skilled in the art. The various embodiments disclosed herein are for purposes of illustration and are not intended to be limiting, with the true scope and spirit being indicated by the claims. The present disclosure is further described with reference to the following examples, which are provided to illustrate certain embodiments and are not intended to limit the scope of the present disclosure or the subject matter claimed.

EXAMPLES

Example 1

In Vitro Models for Testing Tissue Repair and Sealing Devices

This Example provides in vitro model systems that may be adapted and employed for the testing various aspects of the tissue repair and sealing devices disclosed herein. Various physical properties and other parameters of tissue repair and sealing devices as disclosed herein may be tested in in vitro model systems, including in vitro model systems that are described in the scientific, medical, and patent literature and that may be configured for testing the repair and sealing of tissue fenestrations with the devices disclosed herein. See, Dafford, The Spine Journal 15(5):1099 (2015); Chauvet, Acta Neurochirurgica 153(12):2465 (2011); and Wang, MATEC Web of Conferences 119:01044 (2017).

Van Doormaal, *Operative Neurosurgey* 15(4):425 (2018) and Kinaci, *Expert Review of Medical Devices* 16(7):549 (2019) disclose in vitro model systems that use fresh porcine dura for testing acute burst pressures and resistance to intracranial pressure and assessing cerebrospinal fluid leakage in repaired and sealed tissue fenestrations.

Megyesi, *Neurosurgery* 55(4):950 (2004); Chauvet, *Acta Neurochir (Wien)* 153(12):2465 (2011); and Kizmazoglu, Br. J. *Neurosurgery* 33(6):655 (2019) disclose in vitro model systems that use human cadaveric dura mater attached to a cylindrical metal glass filled with colored saline for measuring the water-tightness of repaired and sealed tissue fenestrations and for assessing the pressure at which a repaired and sealed tissue fenestration leaks.

Lin, *International Forum of Allergy and Rhinology* 6(10): 1034 (2016); Lin, *International Forum of Allergy and Rhinology* 5(7):633 (2015); Chorath, *Allergy & Rhinology* 10:1 (2019); and Chen, *American Journal of Rhinology and Allergy* 33(6):757 (2019) disclose a porcine dura in vitro model system using a closed testing apparatus that utilized an infused saline solution to provide unidirectional pressure for determining mean failure pressures of repaired and sealed tissue fenestrations. The in vitro model system employs polyvinyl chloride (PVC) piping capped at one end. A small hole is drilled on the side of the end cap and configured with a 3-way stop cock to infuse saline solution and monitor chamber pressure, simulating increasing intracranial pressure (ICP). A silicone brain is positioned under a simulated cribriform plate within a cylindrical tube. A section of the cribriform plate with a 30 mm-25 mm opening is modeled according to a real computed tomography scan of the skull base (Able, Lexington, MA), imported into CAD (computer-aided design) software (3D Systems, Rockhill, SC), and printed in polycarbonate (Airwolf, Costa Mesa, CA). A second dural support disk is prepared with an identical opening and positioned flushed to the opening of the simulated cribriform plate resection. The cavity pressure was monitored with a pressure transducer (AMTEK, Inc., Ajman, UAE), and its output was transcribed directly onto an excel spreadsheet using WindaqXL (DATAQ, Akron, OH). The transducer was calibrated in mm Hg, and all measurements were converted to centimeters of water (cm H2O). Porcine dura is used because of its similar mechanical properties to human dura. Porcine dura mater and fascia lata were harvested from euthanized pigs and placed in saline and stored at 4° C. Experimentation is conducted within 5 days of retrieval to avoid degradation of the dura. Dural defects are uniformly cut to 24 mm-19 mm dimensions.

Pressure chambers are designed to be adjustable to meet the demands of various testing procedures. The body is made of a schedule 80 PVC Tee fitting that has been outfitted with two flanges and an end cap. On the left side, the end cap is drilled and tapped for a push connect tube fitting that will act as the influent port for our test fluid. This fluid flow is run through a three-way valve with one port controlled by a solenoid valve and the other by a syringe allowing for two different methods of controlling fluid flow. On the right side of the tee there is a flange upon which a membrane is fastened by a piece of acrylic. This acrylic has been designed to mount a 6.5" speaker that will allow for testing of pressure changes created by sound waves that mimic the body's natural respiratory cycle and other human functions. On the top of the tee there is another flange which will hold the test bed. The test bed consists of two pieces of acrylic that will sandwich a piece of commercially-available synthetic Dural material. On the underside of the lower acrylic plate is the pressure transmitter which will monitor the changes in pressure for testing while also controlling the solenoid valve.

FIG. 23A is a human CSF pressure waveform and FIG. 23B is an in vitro chamber pressure waveform obtained with the pressure chamber as described herein. For testing, a closure device includes a probe that is controlled and operated single handedly. This device delivers a bioabsorbable base membrane beneath an incision. Upon insertion, a pressure web is applied on the outside creating a watertight seal. Once the placement is satisfactory, the delivery probe is removed. Should the placement need adjustment it is critical that the sealant device can be adjusted or removed.

Pressure variance via an external speaker that creates waveforms similar to those created naturally by the body, including the natural rhythms of CSF flow, patient movements, coughing and sneezing. The seal is created by the overlap of the dura and the base material. Key physical forces relied on for a watertight seal are the backpressure of CSF, uniform load from the tension arms, and the coefficient of friction between the two surfaces. Back pressure of CSF varies constantly depending on the patient's body and movements. The load applied on the dura varies with the size of each device due to material properties of PLGA. The coefficient of friction helps hold the device in place. A leak that occurs due to any of these forces is overcome in testing.

Example 2

In Vivo Models for Testing Tissue Repair and Sealing Devices

This Example provides in vivo model systems that may be adapted and employed for the testing various aspects of the tissue repair and sealing devices disclosed herein. Various physical properties and other parameters of tissue repair and sealing devices as disclosed herein may be tested in in vivo model systems, including in vivo model systems that are described in the scientific, medical, and patent literature and that may be configured for testing the repair and sealing of tissue fenestrations with the devices disclosed herein.

de Almeida, *Otolaryngology Head Neck Surgery* 141(2): 184 (2009) and Seo, *Journal of Clinical Neuroscience* 58:187 (2018) describe in vivo porcine craniotomy model system that may be adapted for testing the repair of tissue fenestrations by assessing the leakage of cerebrospinal fluids (CSF). In de Almeida, pigs undergo a craniotomy to create fistula through the cribriform plate into the nasal cavity. CSF leaks may be assessed endoscopically prior to and following the repair of tissue fenestration. Inflammation and bone remodeling may be assessed via histopathological analysis.

Dafford, *Spine Journal* 15(5):1099 (2015) describes a comparison of the hydrostatic strength of dural repair techniques in a hydrostatic calf spine model system. Dural leakage is measured as a function of hydrostatic pressure and leak area. Leakage flow rate and the percent reduction of leak area is determined using analysis of variance (ANOVA).

Deng, *Neurological Research* 38(9):799 (2016); Preul, *Neurosurgery* 53(5):1189 (2003); and Zerris, *Journal of Biomedical Materials Research* 83(2):580 (2007) describe in vivo canine cranial dura and arachnoid model systems for assessing CSF leakage. Deng also reports macroscopic and microscopic observations at 30 and 90 days following dura repair. Preul reports the results of Valsalva tests at 1, 4, 7, and 56 days post-surgery and of histopathological analyses for control and treated animals.

Cosgrove, *Journal of Neurosurgery* 106:52 (2007); Osbun, *World Neurosurgery* 78(5):498 (2012); and Weinstein, Journal of Neurosurgery 112(2):219 (2010) describe in vivo craniotomy and craniectomy methodology that may be adapted for testing the repair of tissue fenestrations by assessing the leakage of CSF in humans. The neurological procedures used in Cosgrove are performed infratentorially or supratentorially using suboccipital, temporal, and frontal surgical approaches with durotomy lengths ranging from 1.0-19.0 cm. Osbun assesses complications resulting in unplanned postoperative interventions or reoperations following dural closure and compares the incidence of surgical site infections, CSF leaks, and other neurological complications in both treatment (dural repair) and control groups.

The scope of the disclosure is thus indicated by the appended claims rather than by the foregoing description, and all changes that come within meaning and range of equivalency of the claims are intended to be embraced herein.

What is claimed is:

1. A method for the use of a tissue repair and sealing device in an open (non-MIS) or minimally invasive surgical (MIS) procedure to rapidly repair a tissue fenestration and create a pressure-resistant, watertight seal, comprising:
(a) selecting a tissue repair and sealing device having a detachable graft and clasp assembly removably attached to an applicator assembly,
wherein said detachable graft and clasp assembly comprises a graft subassembly having a biodegradable graft that is fixedly attached to a deployable clasp and coupler subassembly having a deployable clasp with radial struts or spokes and a central coupler and
wherein said applicator assembly comprises an applicator shaft, a clasp retain and release member, and an actuator rod;
(b) folding the deployable clasp radial struts or spokes and inserting into the clasp retain and release member, wherein the biodegradable graft is positioned outside said clasp retain and release member;

(c) inserting the graft through a tissue fenestration and positioning the graft on an inner tissue surface;

(d) positioning the deployable clasp and coupler subassembly on an outer tissue surface;

(e) deploying the tissue repair and sealing device to controllably release the clasp struts or spokes from the clasp retain and release member to contact the outer tissue surface and secure the graft to the inner tissue surface, repairing the tissue fenestration, and create a pressure-resistant, watertight seal.

2. The method of claim 1 wherein said device is deployed by moving said clasp retain and release member via said actuator rod toward a distal end of said applicator shaft to, thereby, release said folded deployable clasp, wherein upon deploying said device the deployable clasp unfolds and contacts the outer tissue surface to secure said biodegradable graft to the inner tissue surface and, thereby, repair the tissue fenestration and creates a pressure-resistant, watertight seal.

3. The method of claim 1 wherein said deployable clasp comprises a biopolymer selected from the group consisting of a polylactide (PLA), a polyglycolide (PGA), a polylactide-co-D, L lactide (PDLLA), a polylactide-co-glycolide (PLGA), a polylactide-co-caprolactone (PLCL), a polycaprolactone (PCL), a polydioxanone (PDO), and a polylactide-co-trimethylene carbonate (PL-TMC), wherein said biopolymer exhibits shape memory and superelasticity characteristics that permit the folding of said biopolymer while retaining the capacity to rapidly unfold to a pre-folded state.

4. The method of claim 1 wherein said deployable clasp assembly comprises a biocompatible, non-ferromagnetic, passivated metal or metal alloy wire that is selected from the group consisting of pure titanium; a titanium-based alloy; a cobalt-based alloy; a platinum-based alloy; and a molybdenum, tungsten, and tantalum alloy;

wherein said biocompatible, non-ferromagnetic, passivated metal or metal alloy wire exhibits shape memory and superelasticity characteristics that permit the folding of said wire while retaining the capacity to rapidly unfold to a pre-folded state.

5. The method of claim 1 wherein said graft assembly is configured (a) to adopt a folded configuration when traversing the tissue fenestration or when retained by said clasp retain and release member and (b) to rapidly unfold to a pre-folded state.

6. The method of claim 1 wherein said biodegradable graft comprises a dural substitute selected from the group consisting of Duraform® dural graft implant, Biodesign® Dural Graft, DuraGen® Matrix, Cerafix dural graft®, PRECLUDE®, Lyoplant Onlay Graft®, Neuro-Patch Dural Graft®, SEAMDURA®, and Durepair™ Regeneration Matrix.

\* \* \* \* \*